US012686689B2

(12) United States Patent
Xie et al.

(10) Patent No.: US 12,686,689 B2
(45) Date of Patent: Jul. 21, 2026

(54) HPK1 INHIBITOR, PREPARATION METHOD THEREFOR AND USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 918 days.

(21) Appl. No.: 17/799,311

(22) PCT Filed: Apr. 19, 2021

(86) PCT No.: PCT/CN2021/088098

§ 371 (c)(1),
(2) Date: Aug. 12, 2022

(87) PCT Pub. No.: WO2021/213317

PCT Pub. Date: Oct. 28, 2021

(65) Prior Publication Data

US 2023/0130909 A1 Apr. 27, 2023

(30) Foreign Application Priority Data

Apr. 20, 2020 (CN) ........................ 202010313871.4

(51) Int. Cl.
*C07D 498/04* (2006.01)
*C07D 519/00* (2006.01)

(52) U.S. Cl.
CPC ......... *C07D 498/04* (2013.01); *C07D 519/00* (2013.01)

(58) Field of Classification Search
CPC .. C07D 498/04; C07D 519/00; C07D 401/14; C07D 471/04; C07D 487/04; C07F 9/6561
See application file for complete search history.

(56) References Cited

FOREIGN PATENT DOCUMENTS

| | | | | |
|---|---|---|---|---|
| CN | 115279760 A | | 11/2022 | |
| WO | 2016197987 A1 | | 12/2016 | |
| WO | 2018108083 A1 | | 6/2018 | |
| WO | 2019238067 A1 | | 12/2019 | |
| WO | 2021013083 A1 | | 1/2021 | |
| WO | WO-2021175270 A1 | * | 9/2021 | ........... C07D 471/00 |

* cited by examiner

*Primary Examiner* — Andrew D Kosar
*Assistant Examiner* — Jonathan D Mahlum
(74) *Attorney, Agent, or Firm* — SZDC Law PC

(57) ABSTRACT

The present invention relates to a compound of general formula (1) and a preparation method therefor and use of the compound of general formula (1) or isomers, crystalline forms, pharmaceutically acceptable salts, hydrates or solvates thereof as an HPK1 inhibitor. The compound of the present invention can be used for preparing a medicament for treating or preventing related diseases mediated by HPK1.

(1)

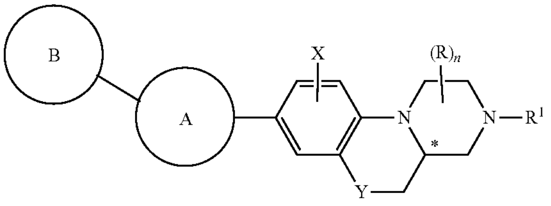

10 Claims, No Drawings

HPK1 INHIBITOR, PREPARATION METHOD THEREFOR AND USE THEREOF

The present application is the National Stage Application of PCT/CN2021/088098, filed on Apr. 19, 2021, which claims priority to Chinese Patent Application CN2020103138714 filed on Apr. 20, 2020, the content of which is incorporated herein by reference in its entirety.

TECHNICAL FIELD

The present invention belongs to the field of medicinal chemistry, and particularly relates to a novel HPK1 inhibitor compound, a preparation method therefor and use thereof in the preparation of a medicament for treating or preventing related diseases mediated by HPK1.

BACKGROUND

Hematopoietic progenitor kinase1 (HPK1) is a serine/threonine protein kinase cloned from hematopoietic progenitor cells and belongs to one of the members of the MAP4K family of mammalian Ste-20-related protein kinases, and other members include MAP4K2/GCK, MAP4K3/GLK, MAP4K4/HGK, MAP4K5/KHS and MAP4K6/MINK [Mol. Cell Biol., 1999, 19 (2): 1359-1368]. HPK1 is expressed mainly in hematopoietic immune-related cells such as hematopoietic progenitor cells, T cells, B cells, NK cells, immunodendritic cells, macrophages and mast cells[J. Biol. Chem., 2004, 279 (47): 49551-49561].

HPK1 is activated when T and B cell receptors and dendritic cells are activated, and feedback inhibits T and B cell receptor activation, dendritic cell antigen presentation and other immune responses. HPK1 interacts with many linker proteins, such as SLP-76 family, CARD11, HIS, HIP-55, GRB2 family, LAT and CRK family, to function. When T and B cell receptors are activated, HPK1 phosphorylates SLP-76 family protein, and regulates the activity of SLP-76 protein complex, thereby negatively regulating the signal transduction pathway of T cell receptor and B cell receptor. Consistent with the immunosuppressive effect of HPK1, the activity of HPK1-deleted T cells and dendritic cells is enhanced, and the killing power to tumors is stronger. Therefore, the inhibition of HPK1 enhances the immune response of tumor, and HPK1, as a regulation mechanism of T cell mediated immune response, becomes a hot spot for new immune anti-tumor development. The HPK1 inhibitor has potential application value in treating malignant solid tumor or blood cancer (such as acute myelogenous leukemia, bladder epithelial cancer, breast cancer, colon cancer, lung cancer, pancreatic cancer and melanoma) and HPK1 related immune diseases.

At present, no medicine is available on the market aiming at the HPK1 target, and in order to better meet the huge clinical requirement, the development of a novel compound for regulating the activity of HPK1 provides a new direction for treating related diseases.

SUMMARY

The present invention aims to provide a compound of general formula (1), or isomers, crystalline forms, pharmaceutically acceptable salts, hydrates or solvates thereof:

(1)

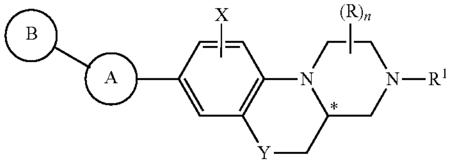

in formula (1):

"*" denotes a chiral center;

n is an integer of 0, 1, 2 or 3;

X is H, halogen, $C_{1-3}$ alkyl, $C_{1-3}$ haloalkyl or $C_{3-6}$ cycloalkyl;

Y is —O—, —NH— or —N($C_{1-3}$ alkyl)-;

when each R is linked to a different carbon atom, each R is independently H or $C_{1-3}$ alkyl; when two R are simultaneously linked to the same carbon atom, the two R may independently be H or $C_{1-3}$ alkyl or form a carbon group (C═O) with a carbon atom linked thereto;

$R^1$ is H, $C_{1-6}$ alkyl, $C_{3-6}$ cycloalkyl, heterocycloalkyl, hydroxy-substituted $C_{1-6}$ alkyl, halogen-substituted $C_{1-6}$ alkyl, $C_{1-6}$ alkoxy-substituted $C_{1-6}$ alkyl or cyano-substituted $C_{1-6}$ alkyl;

A is the following group:

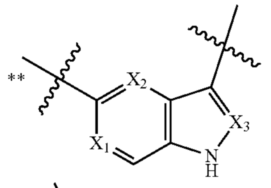

or

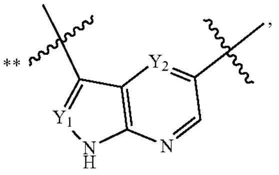

, wherein "**" denotes a position linking to a group B, $X_1$ is N, CH, CF, C—$C_1$, C-Me or C—CN, $X_2$ is N, CH, CF, C—Cl, C-Me or C—CN, $X_3$ is N or CH, $Y_1$ is N or CH, and $Y_2$ is N, CH, C-Me or C—CN; B is $C_{6-10}$ aryl or 5-10 membered heteroaryl, wherein the 5-10 membered heteroaryl consists of at least 1 carbon atom and 1-4 heteroatoms selected from the group consisting of N, O and S; wherein the N or S atom may be oxidized; wherein ring carbon atoms of the 5-10 membered heteroaryl may be optionally substituted with oxygen to form a carbonyl group (C═O); and the $C_{6-10}$ aryl and 5-10 membered heteroaryl are optionally substituted with 1-5 substituents independently selected from $R^2$;

$R^2$ is independently halogen, CN, $NO_2$, $C_{1-6}$ alkyl, $C_{2-6}$ alkenyl, $C_{2-6}$ alkynyl, $C_{1-6}$ haloalkyl, cyano-substituted $C_{1-6}$ alkyl, hydroxy-substituted $C_{1-6}$ alkyl, $C_{1-3}$ alkoxy-substituted $C_{1-6}$ alkyl, $C_{1-3}$ haloalkoxy-substituted $C_{1-6}$ alkyl, $C_{3-6}$ cycloalkyl, 4-7 membered heterocycloalkyl, 5-7 membered heteroaryl, $OR^3$, $SR^3$, $C(O)R^3$, $S(O)R^3$, $S(O)_2R^3$, $C(O)OR^3$, $OC(O)R^3$, $NR^4R^5$, $P(O)R^4R^5$, $C(O)NR^4R^5$, $OC(O)NR^4R^5$, —$C_{1-6}$ alkyl-$NR^4R^5$, —O—$C_{1-6}$ alkyl-$NR^4R^5$, —$C_{1-6}$ alkyl-$OR^3$, —O—$C_{1-6}$ alkyl-$R^3$, -hydroxy-substituted $C_{1-6}$ alkyl- $R^3$, —$NR^6C(O)R^3$, —$NR^6S(O)_2R^3$, —$NR^6CO$—$C_{1-3}$ alkyl-$R^3$ or —$NR^6CO$—$C_{1-3}$ alkyl-$NR^4R^5$;

or two adjacent $R^2$ substituents on ring B, together with atoms linked thereto, form a fused 4-7 membered heterocycloalkyl or $C_{3-7}$ cycloalkyl, wherein the fused 4-7 membered heterocycloalkyl contains at least 1 carbon atom and 1-4 heteroatoms selected from the group consisting of N, O and S; wherein the N or S atom may be oxidized; wherein ring carbon atoms of the fused 4-7 membered heterocycloalkyl may be optionally substituted with oxygen to form a carbonyl group (C═O); and the fused 4-7 membered heterocycloalkyl or the $C_{3-7}$ cycloalkyl is optionally substituted with 1-5 substituents independently selected from $R^7$;

each $R^3$ is independently H, $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, $C_{6-10}$ aryl, 5-7 membered heteroaryl, cyano-substituted $C_{1-6}$ alkyl, hydroxy-substituted $C_{1-6}$ alkyl, $C_{1-3}$ alkoxy-substituted $C_{1-6}$ alkyl or $C_{1-3}$ haloalkoxy-substituted $C_{1-6}$ alkyl;

each of $R^4$ and $R^5$ is independently H, $C_{1-6}$ alkyl, $C_{2-6}$ alkenyl, $C_{2-6}$ alkynyl, $C_{1-6}$ haloalkyl, $C_{3-6}$ cycloalkyl, cyano-substituted $C_{1-6}$ alkyl, hydroxy-substituted $C_{1-6}$ alkyl, $C_{1-3}$ alkoxy-substituted $C_{1-6}$ alkyl or $C_{1-3}$ haloalkoxy-substituted $C_{1-6}$ alkyl, $C_{6-10}$ aryl-substituted $C_{1-6}$ alkyl or 5-10 membered heteroaryl-substituted $C_{1-6}$ alkyl, or $R^4$ and $R^5$, together with an N atom, form 4-12 membered heterocycloalkyl, the 4-12 membered heterocycloalkyl optionally being substituted with 1-5 substituents independently selected from $R^7$;

each $R^6$ is H or $C_{1-3}$ alkyl;

each $R^7$ is OH, CN, $NH_2$, NHMe, $NMe_2$, $C_{1-6}$ alkyl, $C_{1-6}$ haloalkyl or $C_{1-6}$ alkoxy.

In another preferred embodiment, in general formula (1), X is H, F, Cl, Me, Et, $CF_3$, isopropyl or cyclopropyl.

In another preferred embodiment, in general formula (1), Y is —O—, —NH—, —N(Me)- or —N(Et)—.

In another preferred embodiment, in general formula (1), R is H or Me.

In another preferred embodiment, in general formula (1), $R^1$ is H, Me, Et,

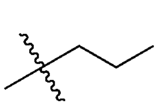 , 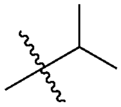 , 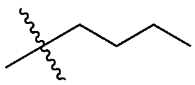 ,
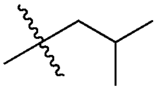 , 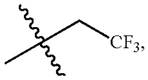 , 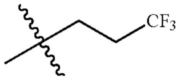 ,
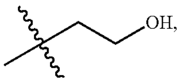 , 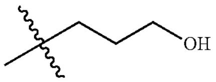 ,
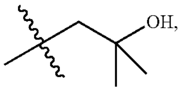 , 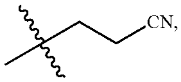 ,
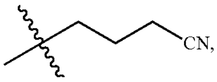 , 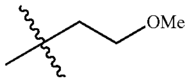 ,
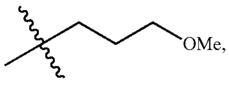 , 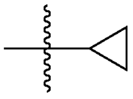 ,
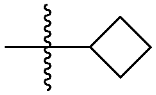 , 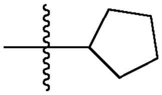 , -continued

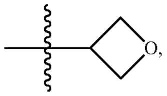 , 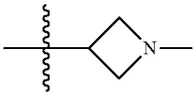 ,
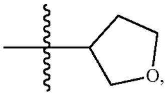 , 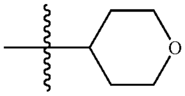 or
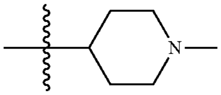 .

In another preferred embodiment, in general formula (1), A is the following group:

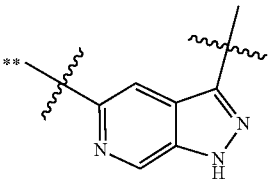 ,
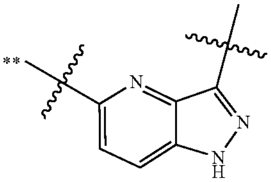 ,
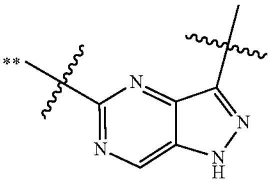 ,
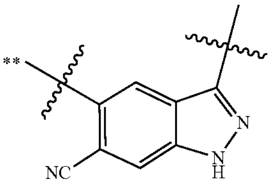 ,
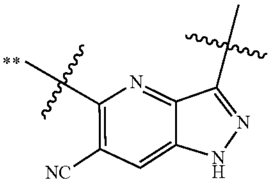 ,
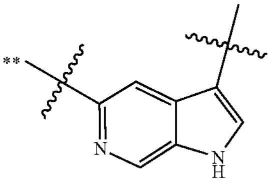 ,
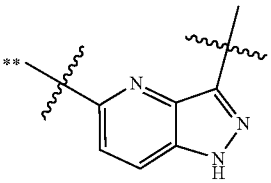 , -continued
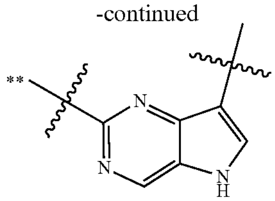
,
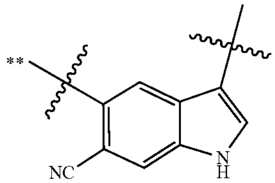
,
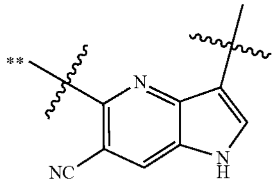
,
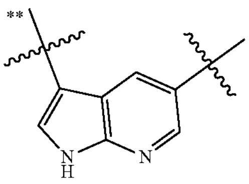
,
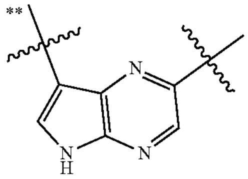
,
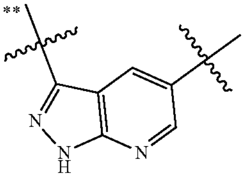
or
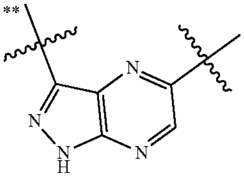
,
wherein "**" denotes a position linking to a group B.
In another preferred embodiment, in general formula (1), B is
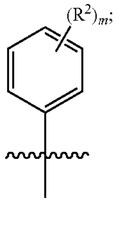
$R^2$ is independently H, $CH_3$, F, Cl, $OCH_3$, $CF_3$, CN, $CONH_2$,
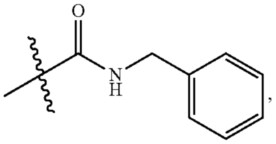
-continued
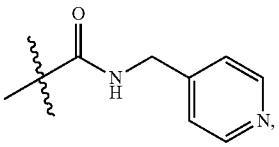
$NHSO_2CH_3$, $NHCOCH_3$, $PO(CH_3)_2$, $SO_2CH_3$, $SO_2NH_2$, $SO_2NHCH_3$, $CH_2NHCH_3$, $CH_2NHCH_2CH_3$,
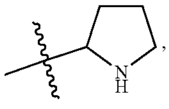
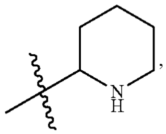
$CH(CH_3)NHCH_3$, $CH_2CN$, $CH_2OCH_3$,
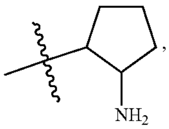
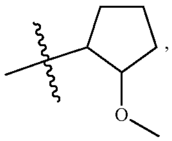
$NHCOCH_2N(CH_3)_2$,
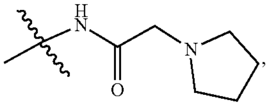
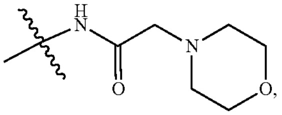
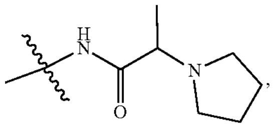
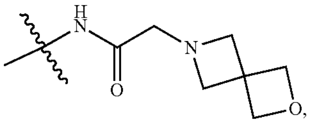
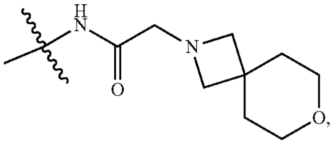
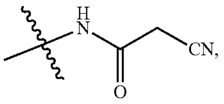
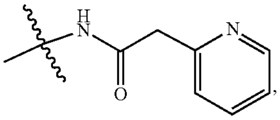

-continued
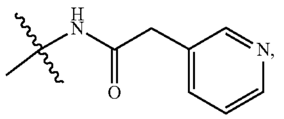
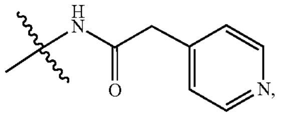
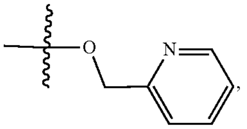
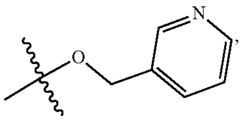
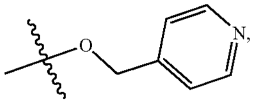
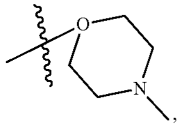
$OCON(CH_3)_2$,
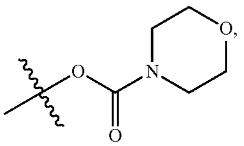 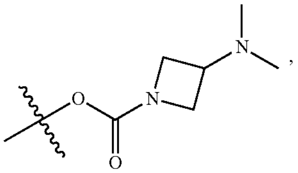
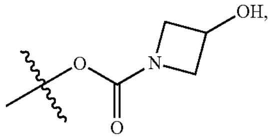
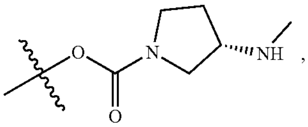
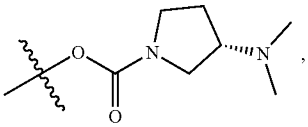
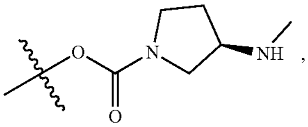
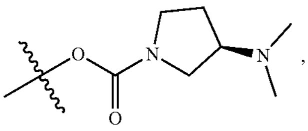
-continued
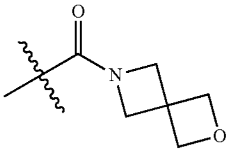, 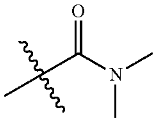,
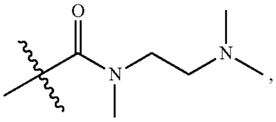
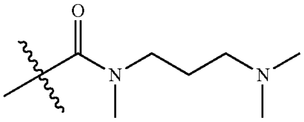
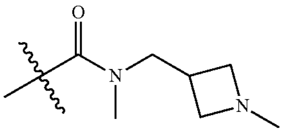, 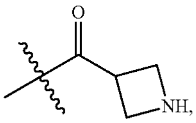
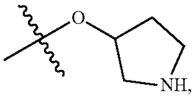 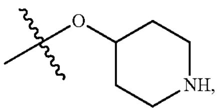
$OCH_2CH_2CH_2NH_2$, $OCH_2CH_2CH_2N(CH_3)_2$,
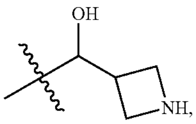 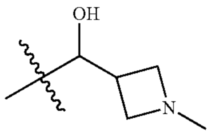,
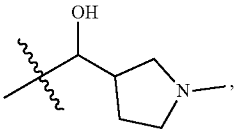, 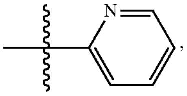
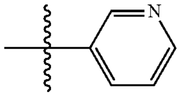 or 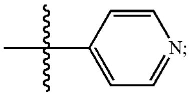
m is an integer of 0, 1, 2 or 3.
In another preferred embodiment, in general formula (1), B is
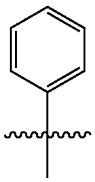, 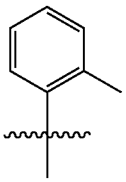, 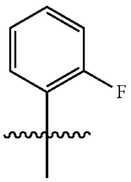,
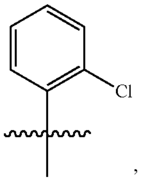, 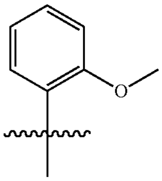, 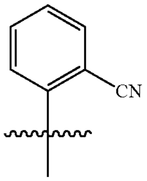, -continued
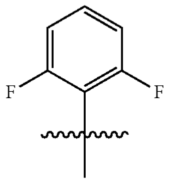,
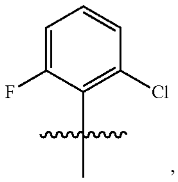,
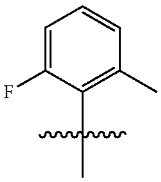,
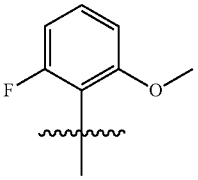,
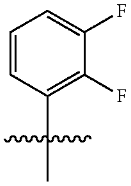,
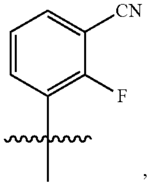,
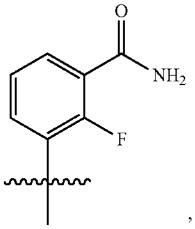,
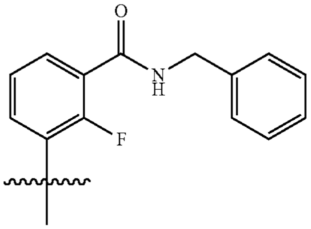,
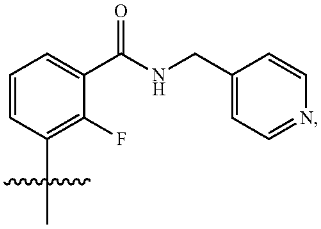
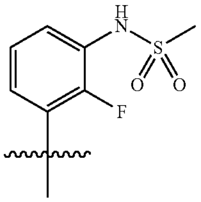,
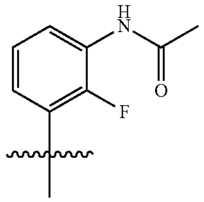,
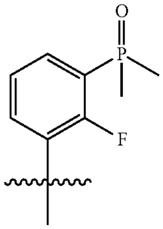,
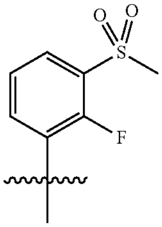,
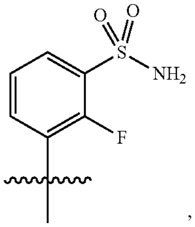,
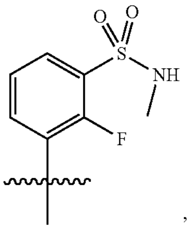,
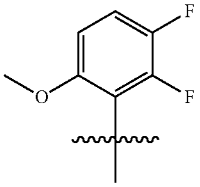,
-continued
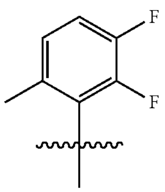,
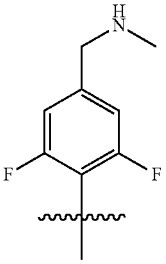,
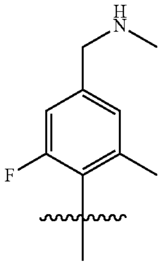,
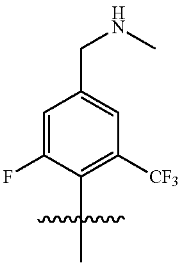,
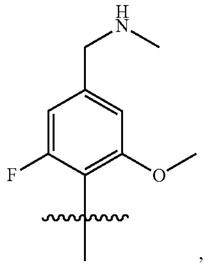,
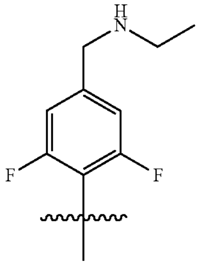,
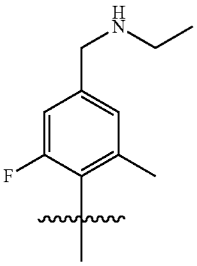,
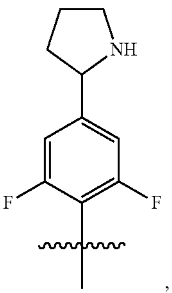,
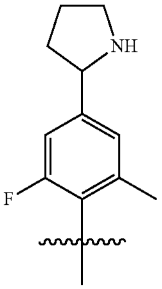,
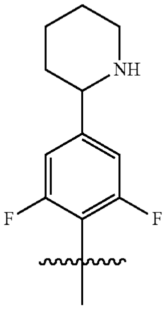,
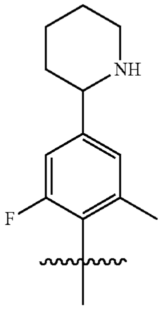,
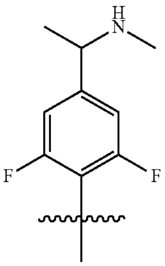,
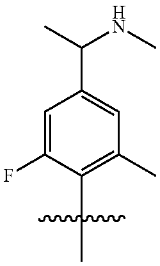,
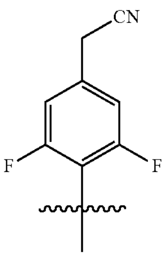, -continued
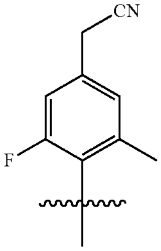,
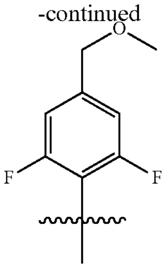,
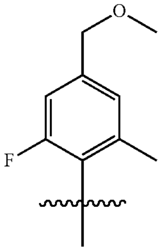,
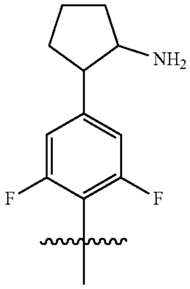,
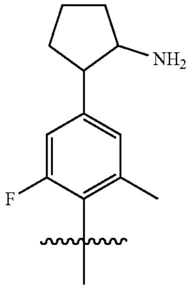,
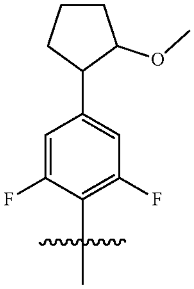,
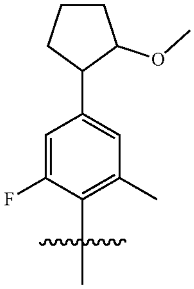,
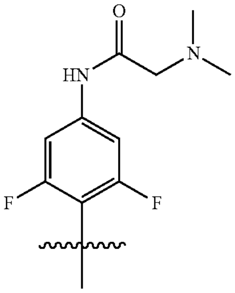,
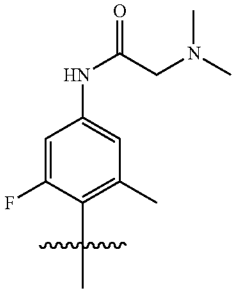,
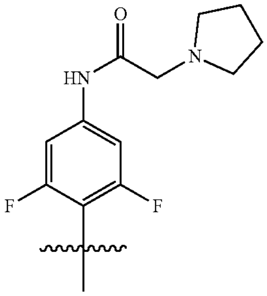,
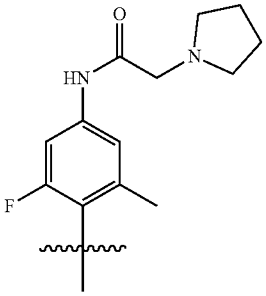,
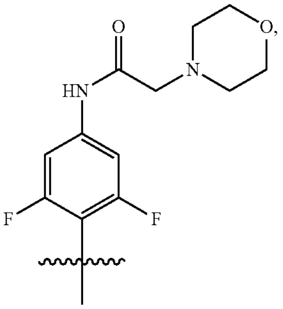
-continued
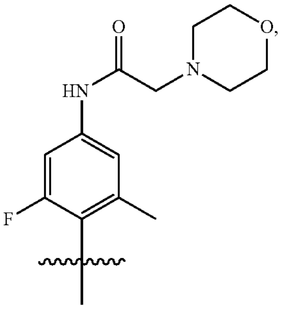
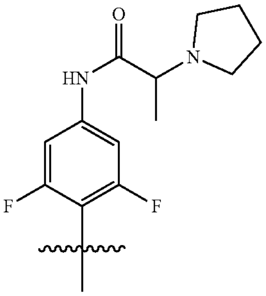,
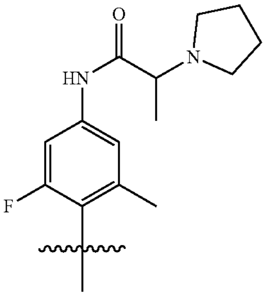,
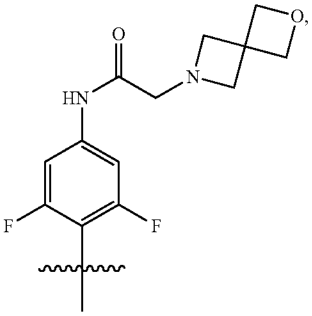
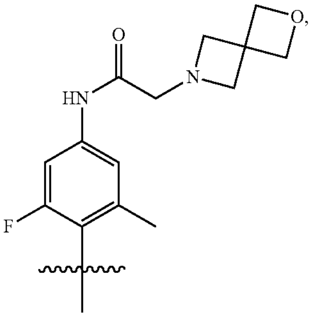
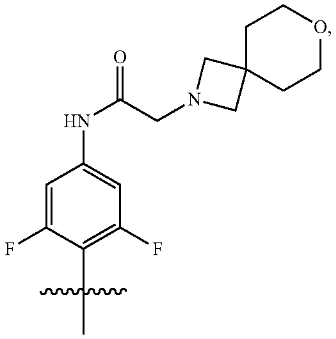

-continued
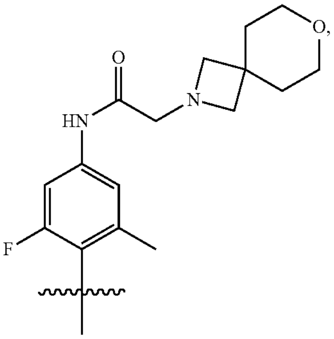
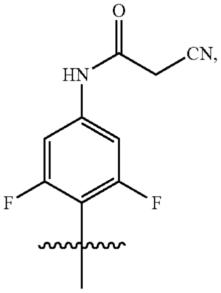
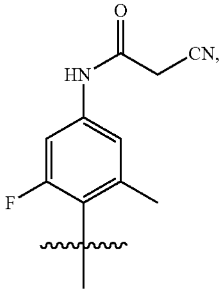
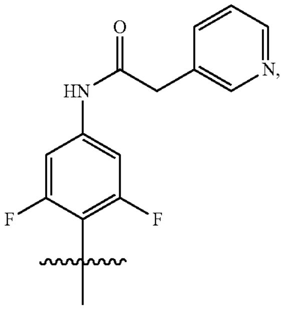
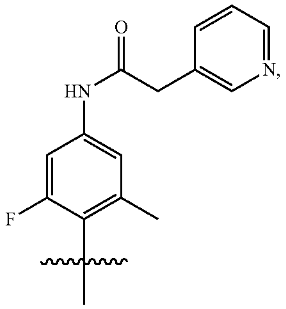
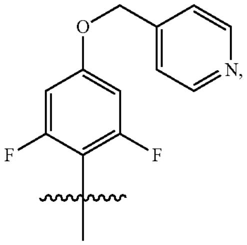
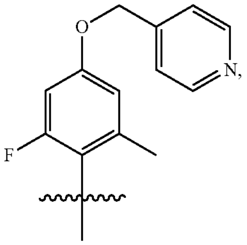
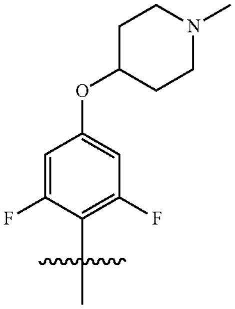
,
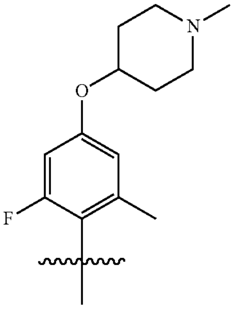
,
-continued
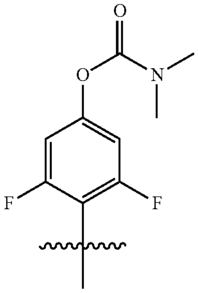
,
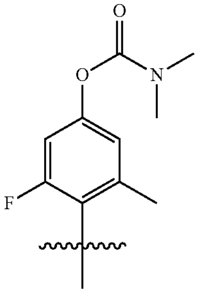
,
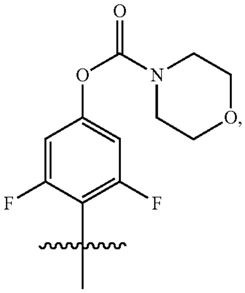
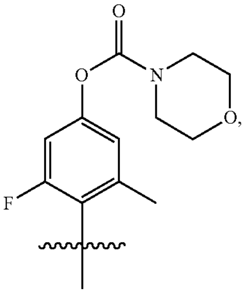
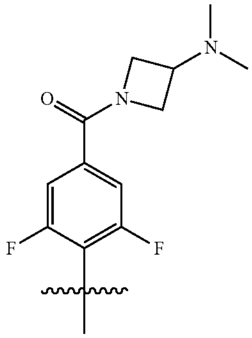
,
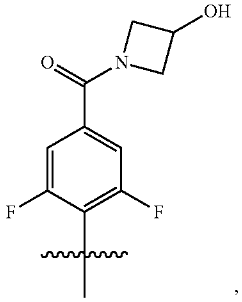
,
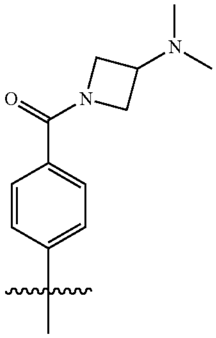
,
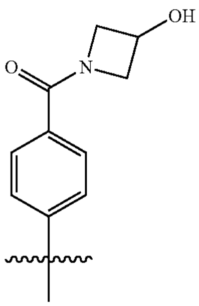
,
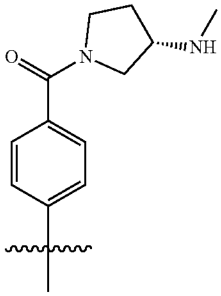
,
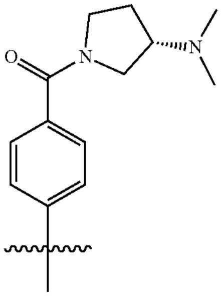
, -continued
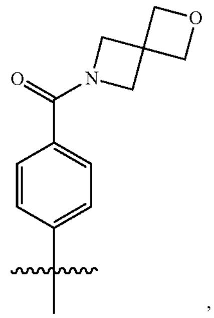
,
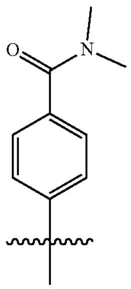
,
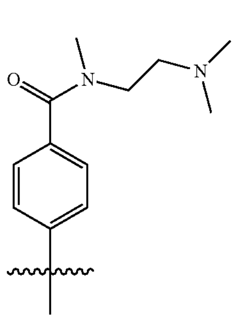
,
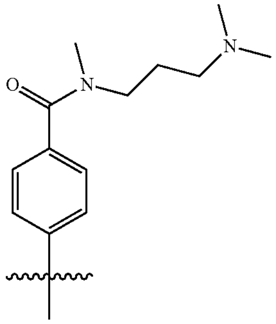
,
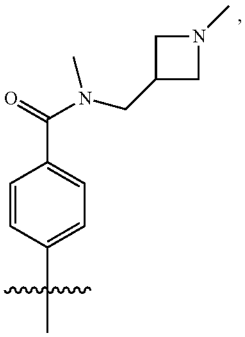
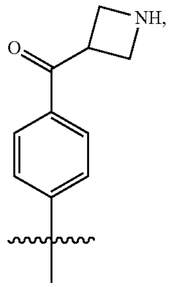
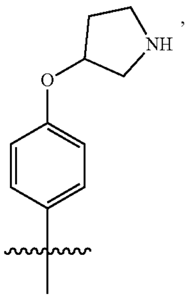
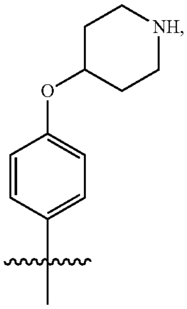
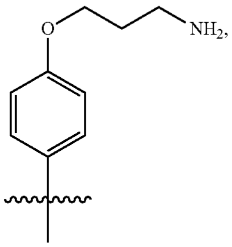
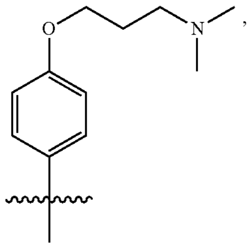
-continued
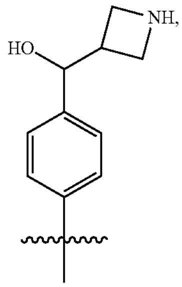
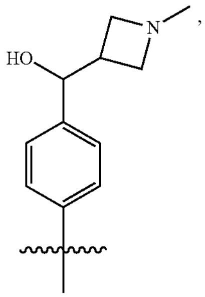
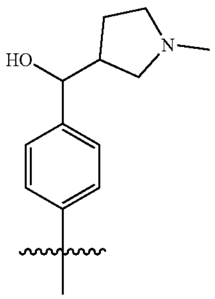
or
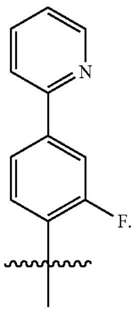
In another preferred embodiment, in general formula (1), B is
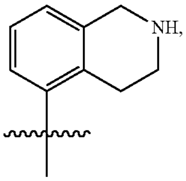
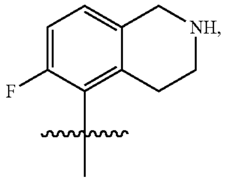
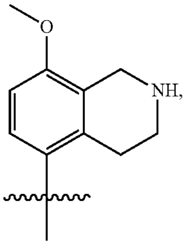
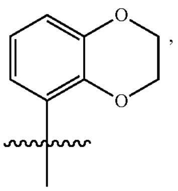
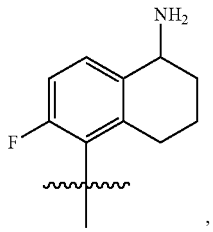
,
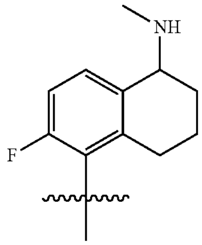
,
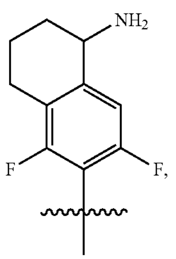
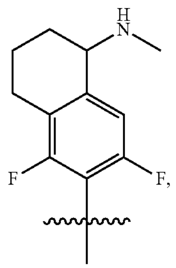

-continued
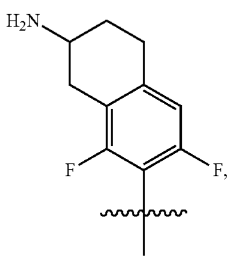
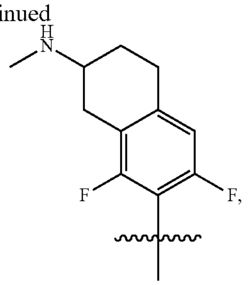
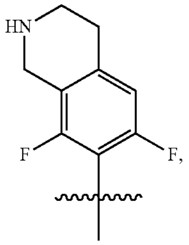
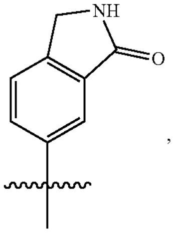
,
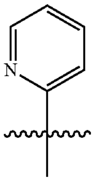
,
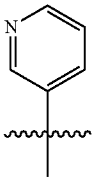
,
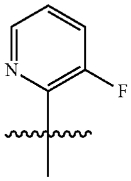
,
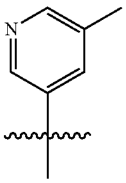
,
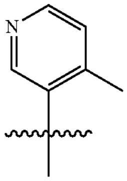
,
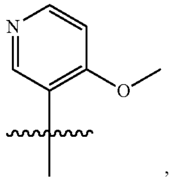
,
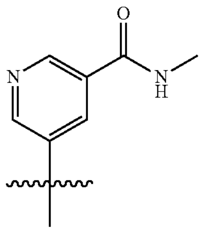
,
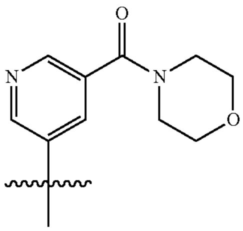
,
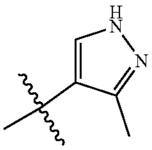
,
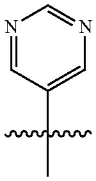
,
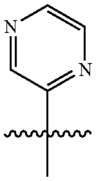
,
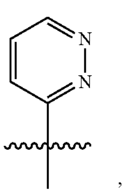
,
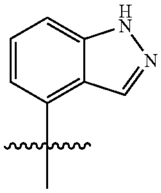
,
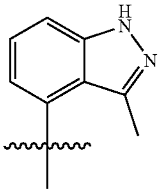
,
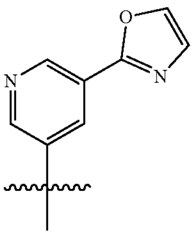
,
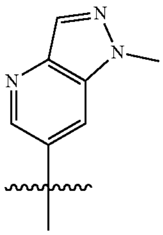
,
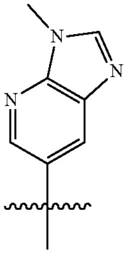
,
-continued
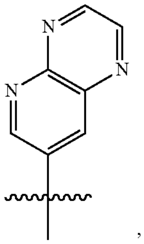
,
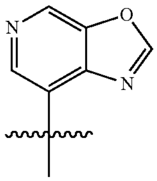
,
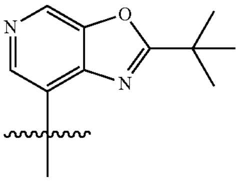
,
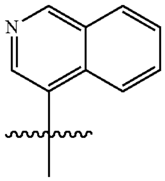
,
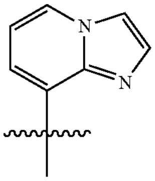
,
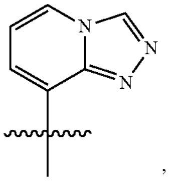
,
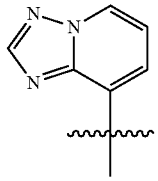
,
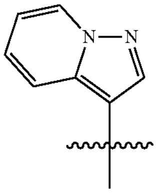
,
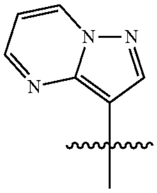
,
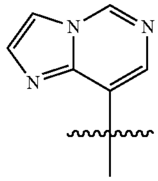
,
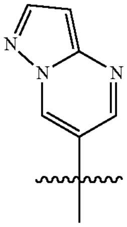
,
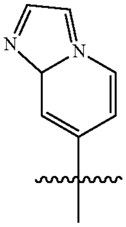
,
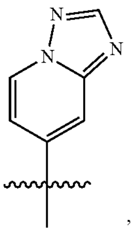
,
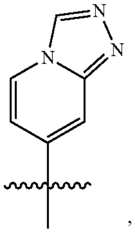
,
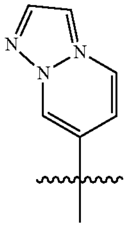
or
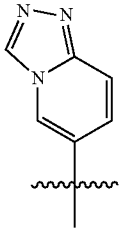
.

In various embodiments, representative compounds of the present invention have one of the following structures:
1
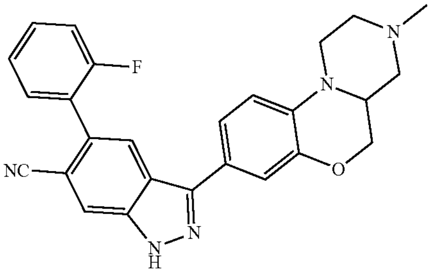
2
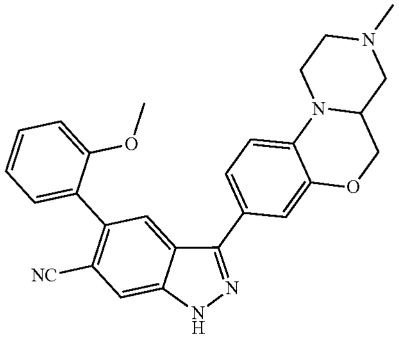
3
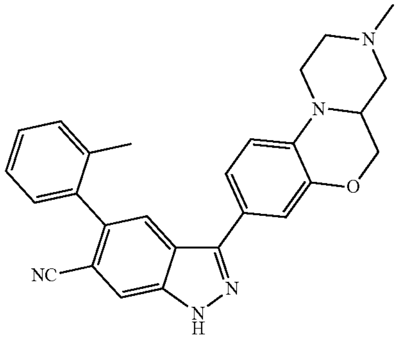
4
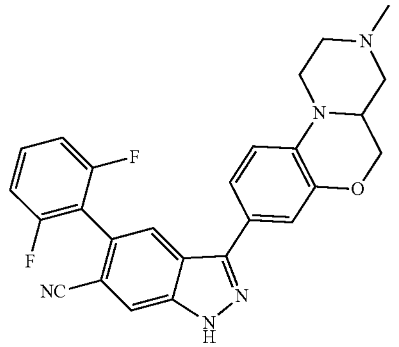
-continued
5
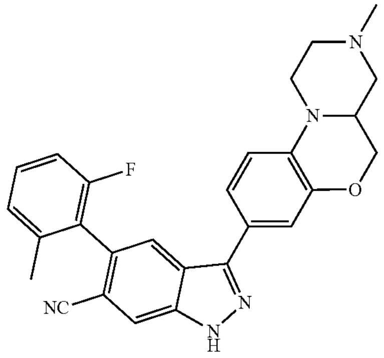
6
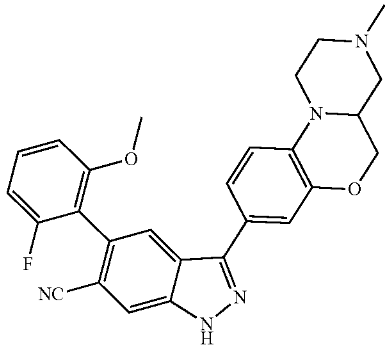
7
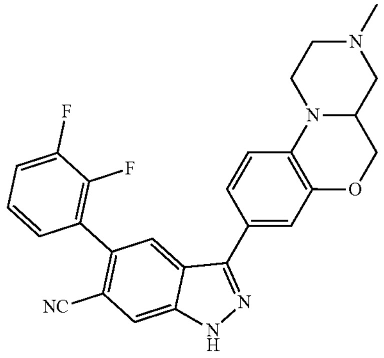
8
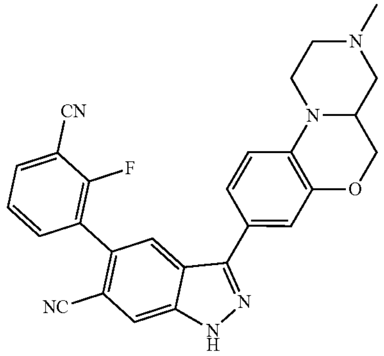

9
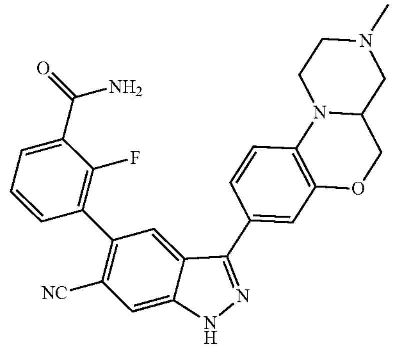
10
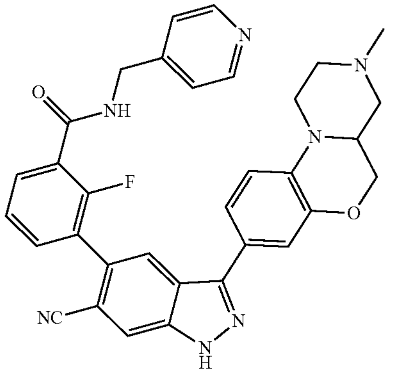
11
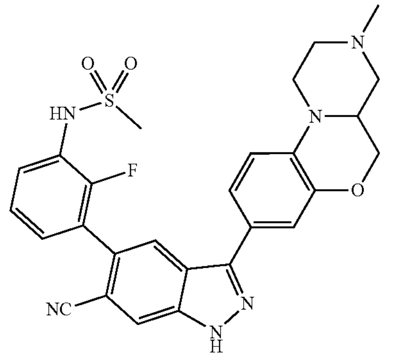
12
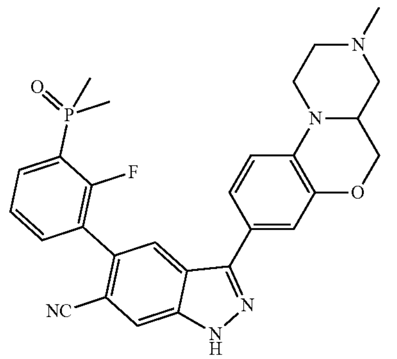
13
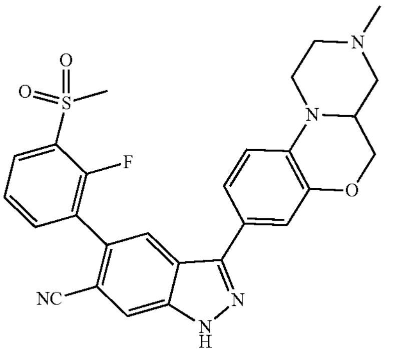
14
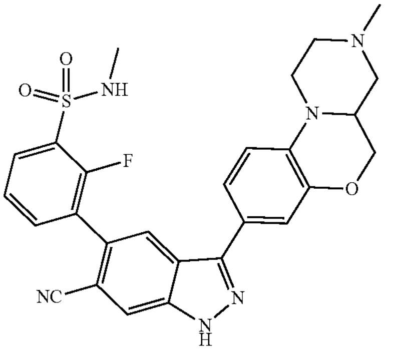
15
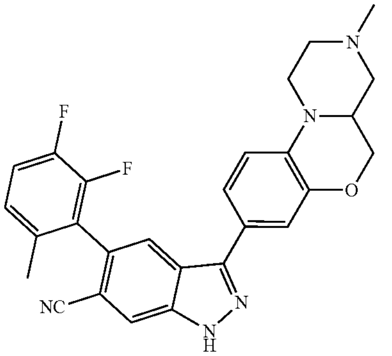
16
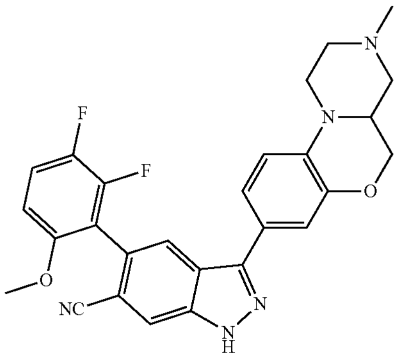

-continued
17
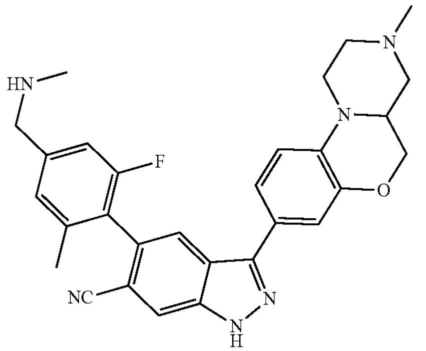
18
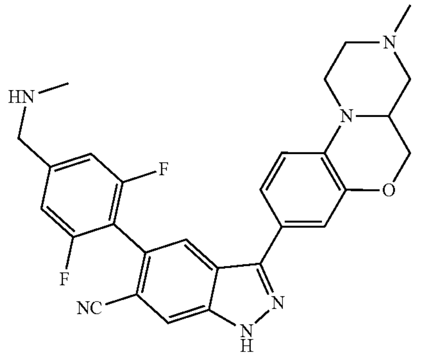
19
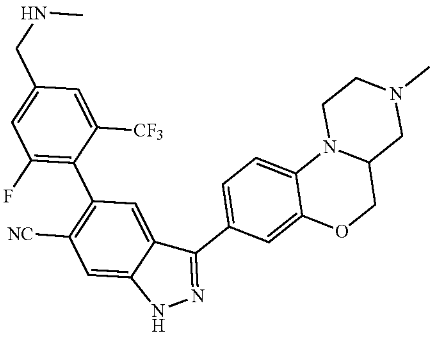
20
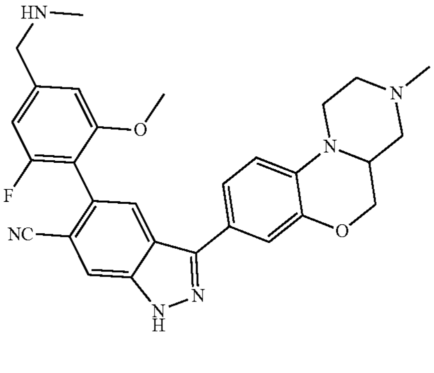
-continued
21
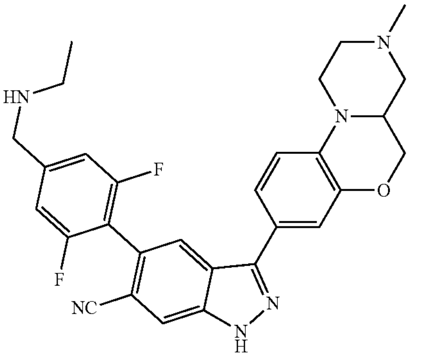
22
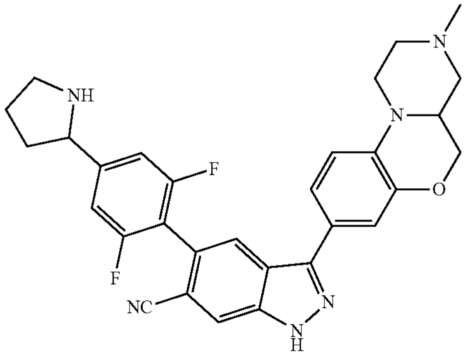
23
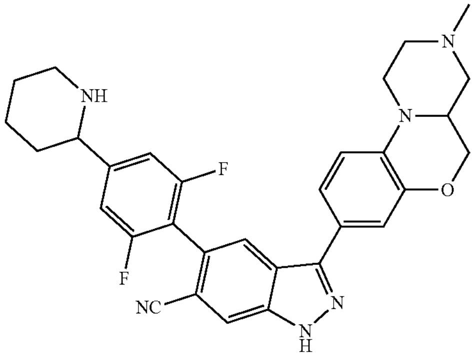
24
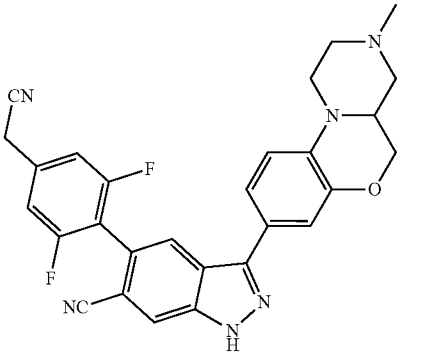

-continued
25
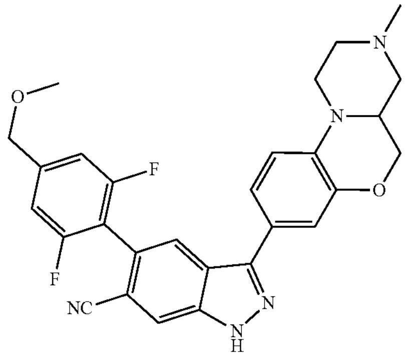
26
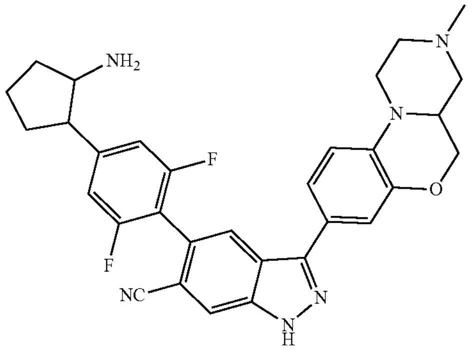
27
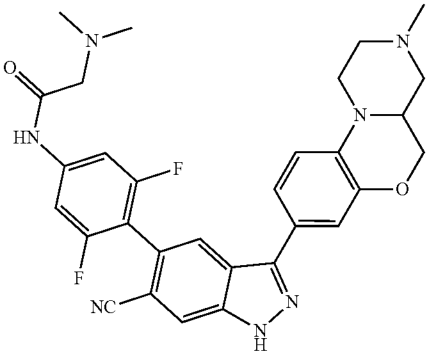
28
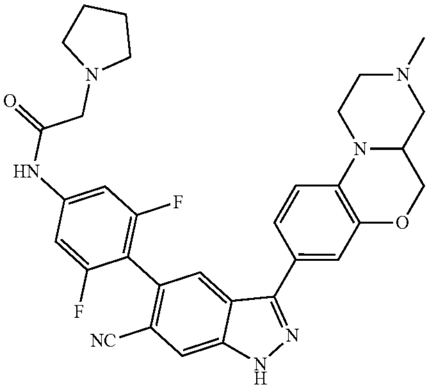
-continued
29
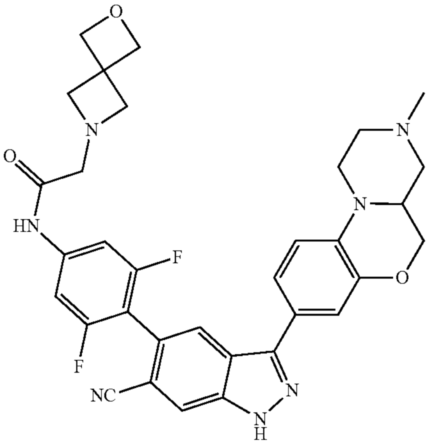
30
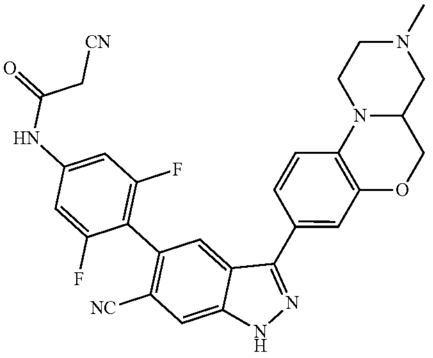
31
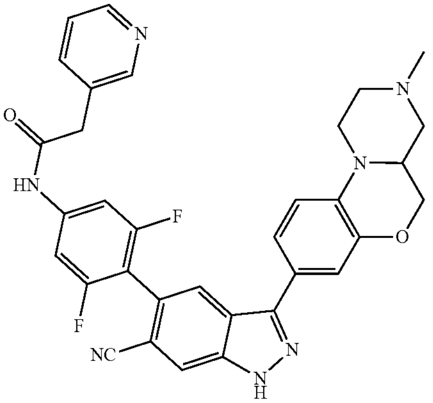
32
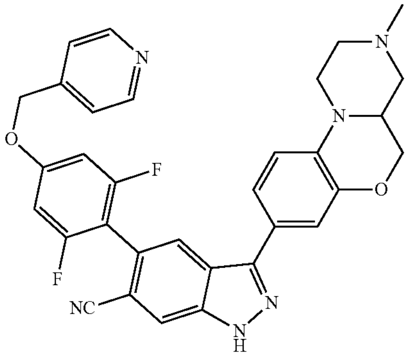

-continued
33
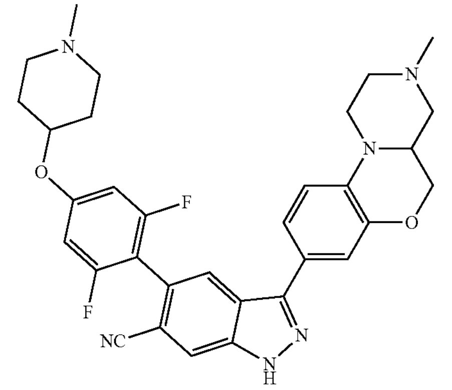
34
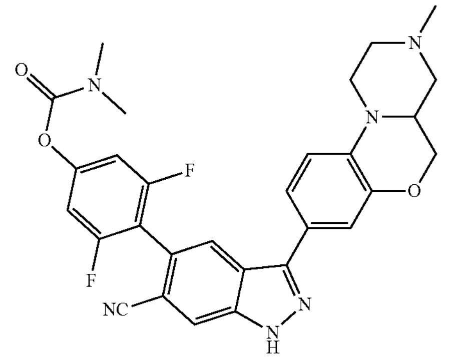
35
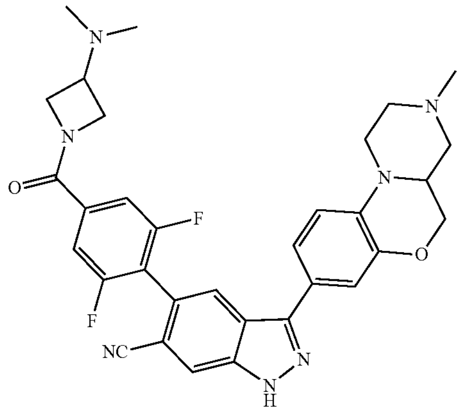
36
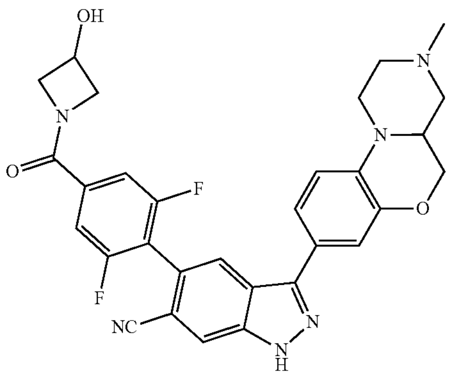
-continued
37
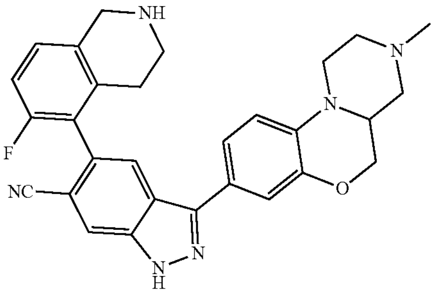
38
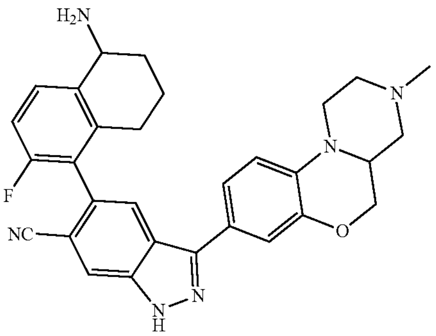
39
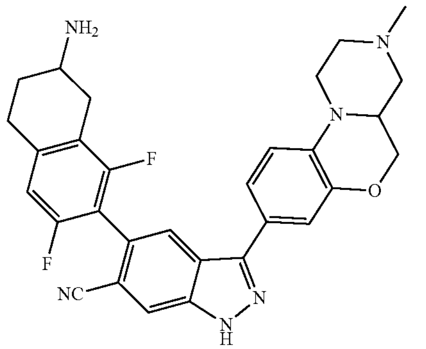
40
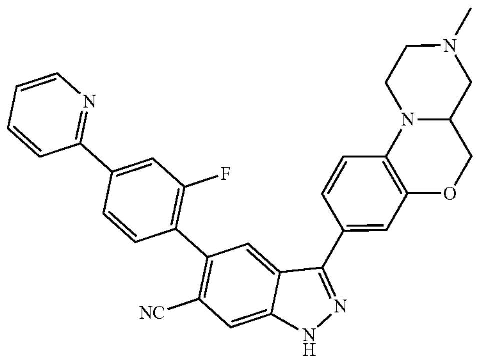

-continued
41
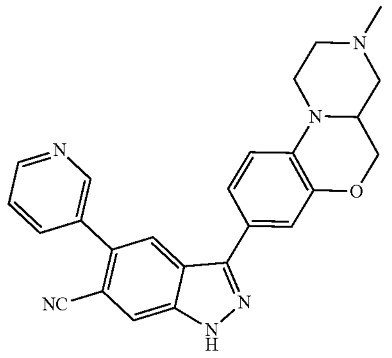
42
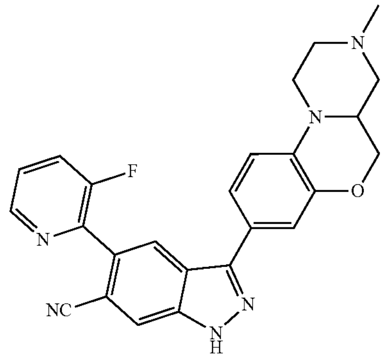
43
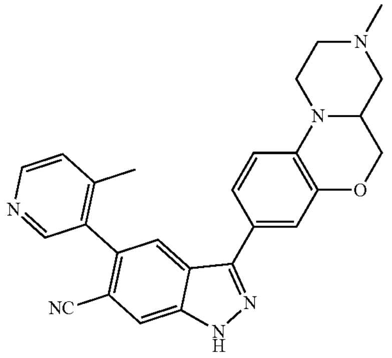
44
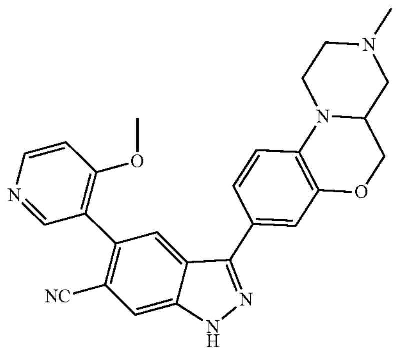
-continued
45
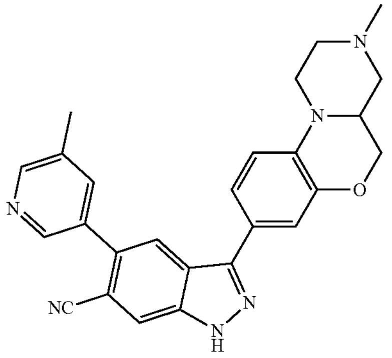
46
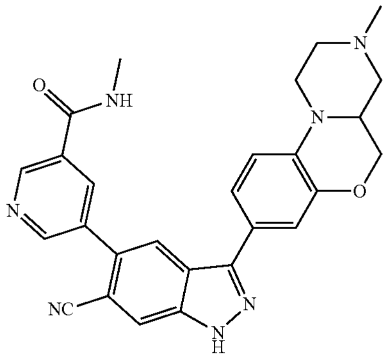
47
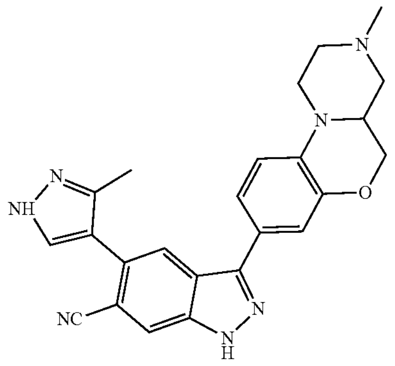
48
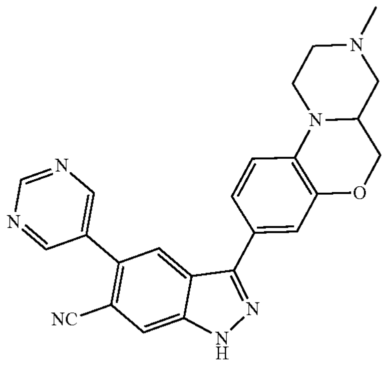

-continued
49
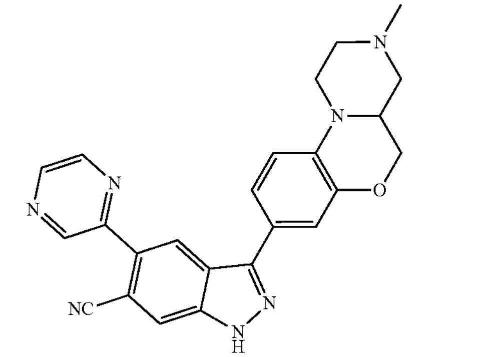
50
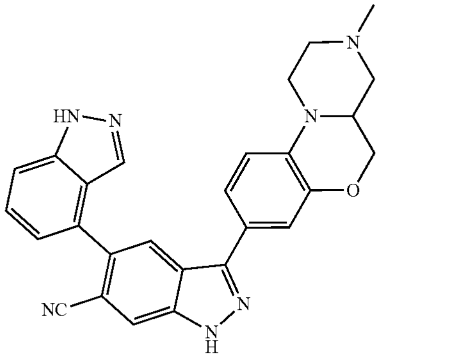
51
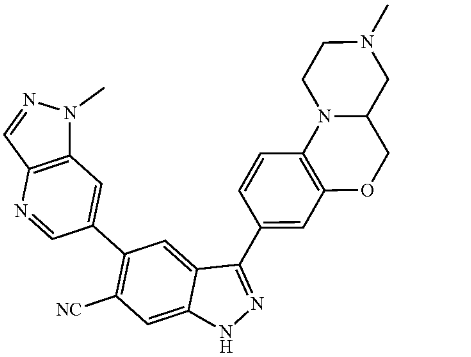
52
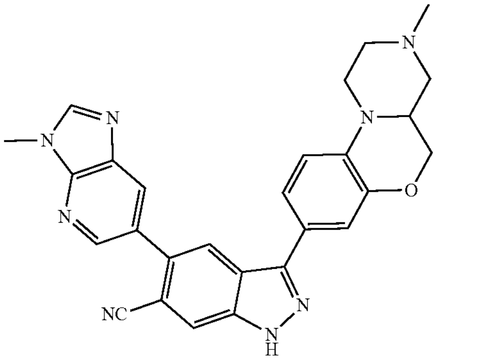
-continued
53
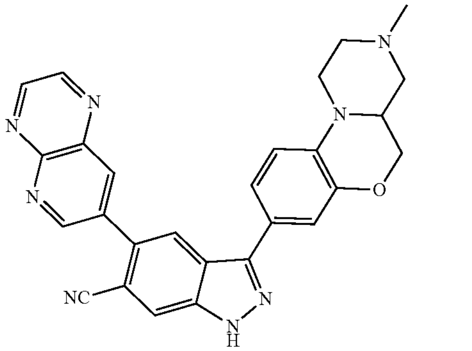
54
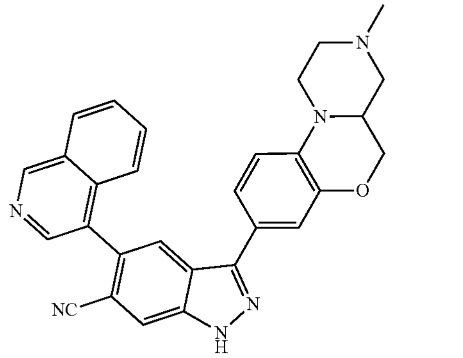
55
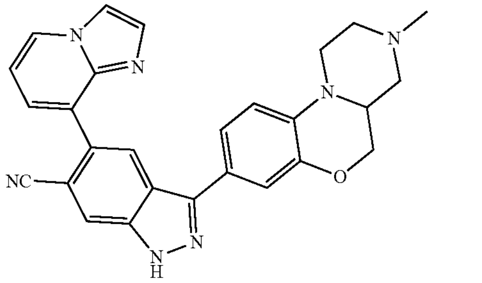
56
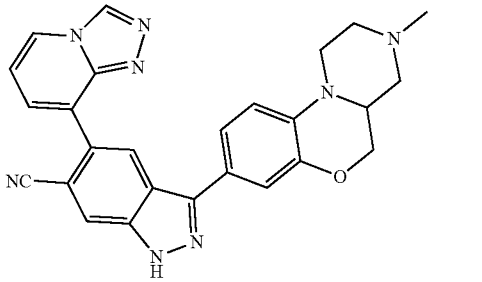
57
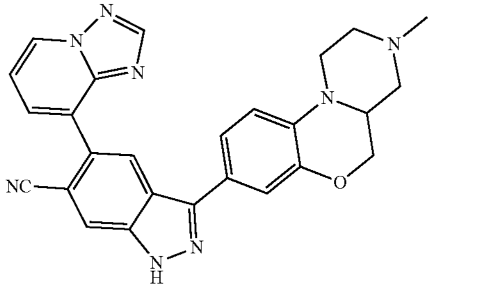

-continued
58
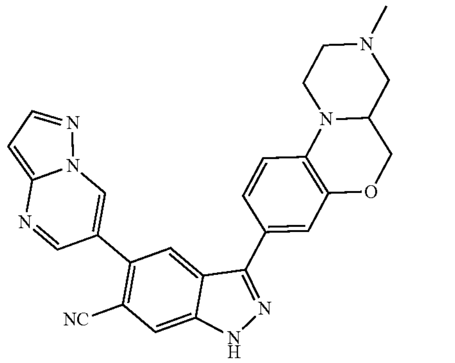
59
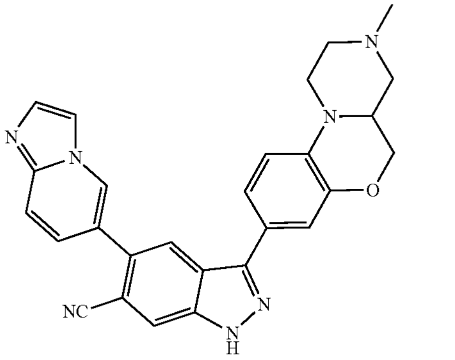
60
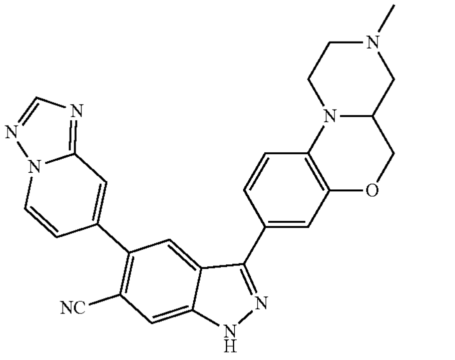
61
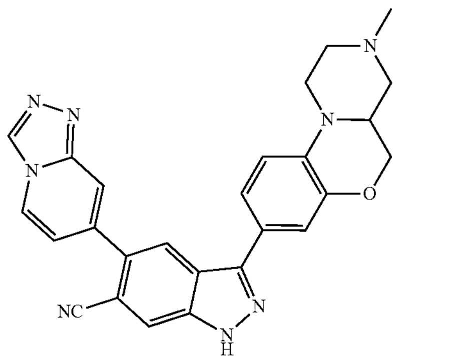
-continued
62
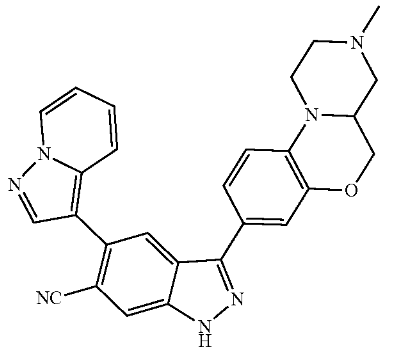
63
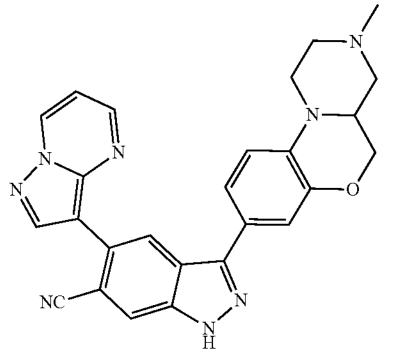
64
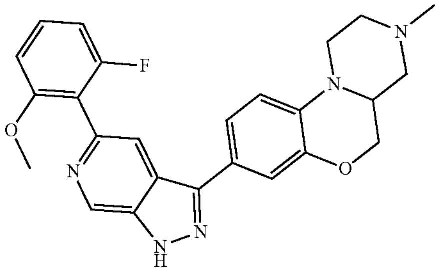
65
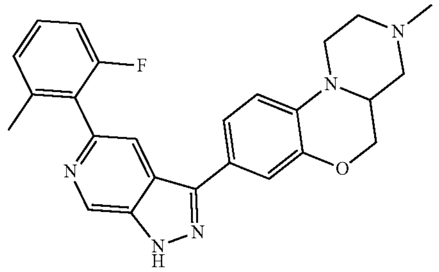
66
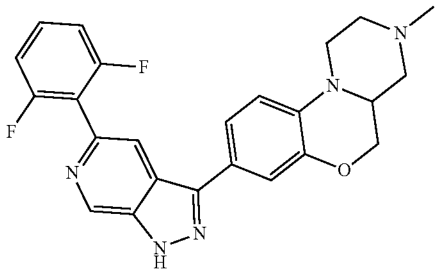

-continued
67
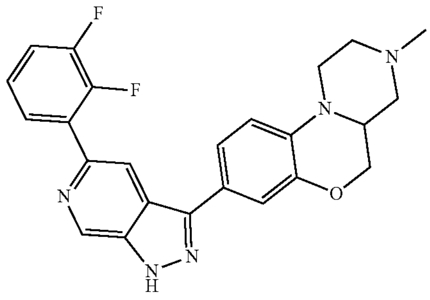
68
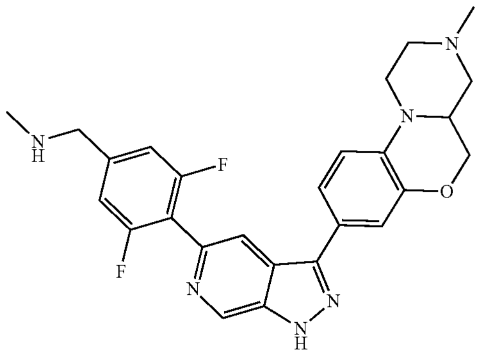
69
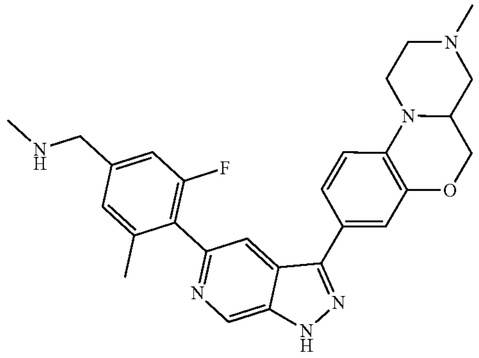
70
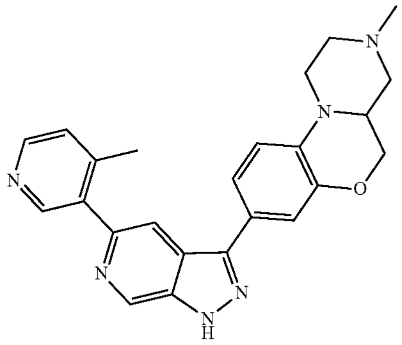
-continued
71
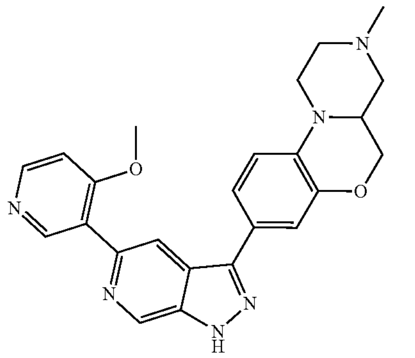
72
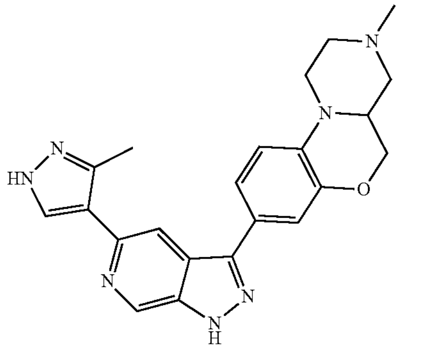
73
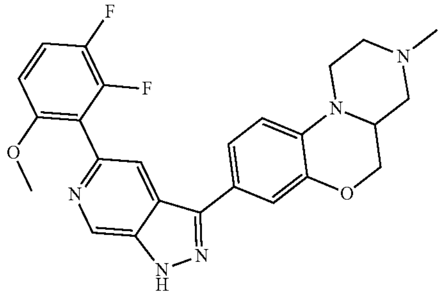
74
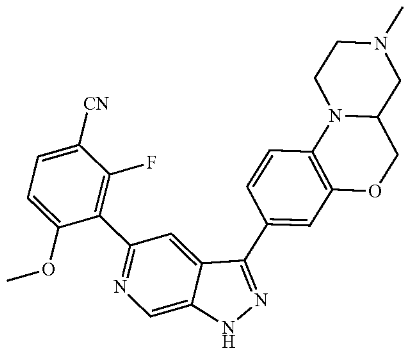

-continued
75
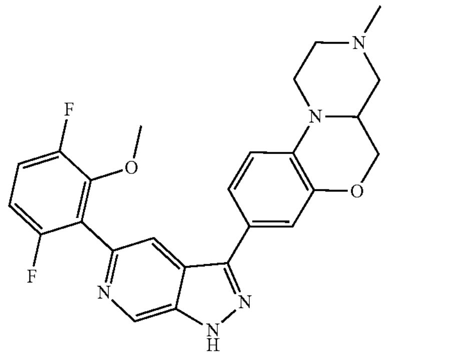
76
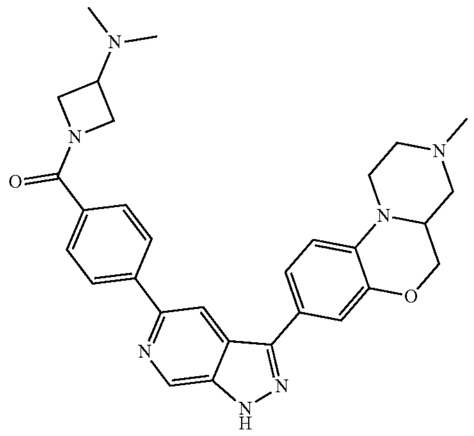
77
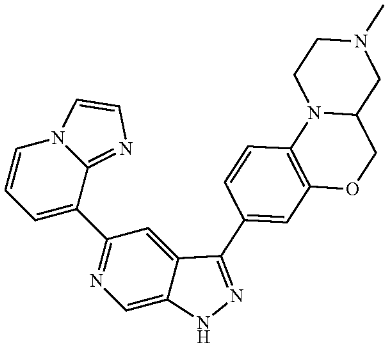
78
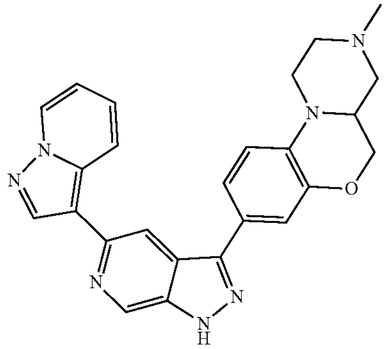
-continued
79
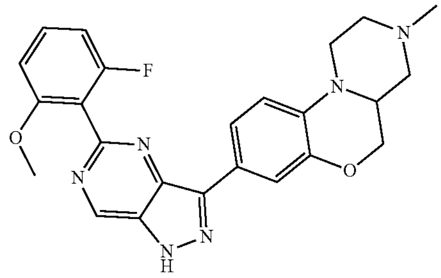
80
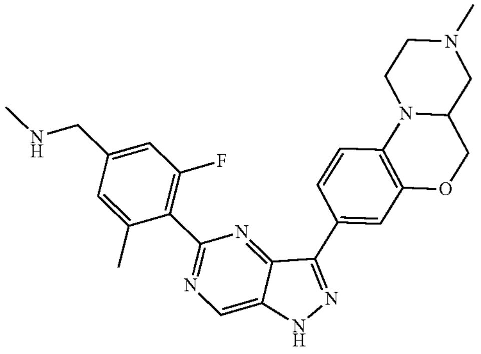
81
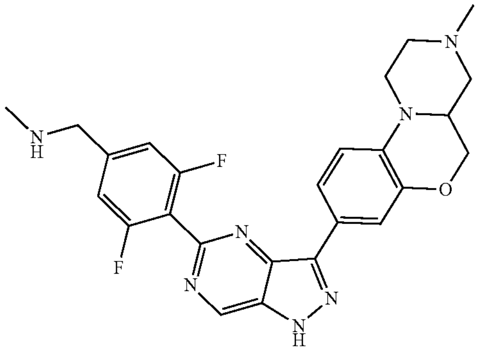
82
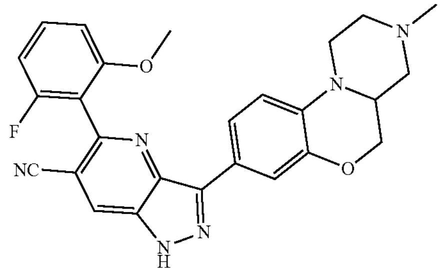
83
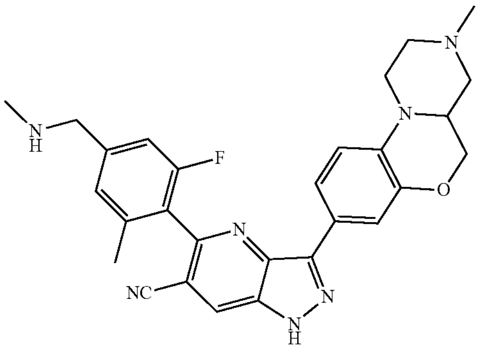

-continued
84
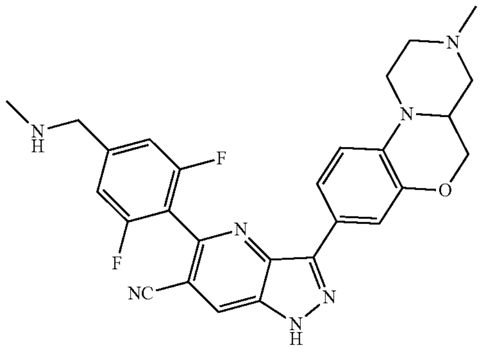
85
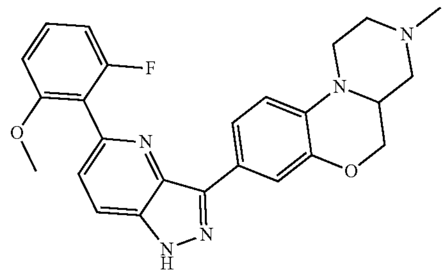
86
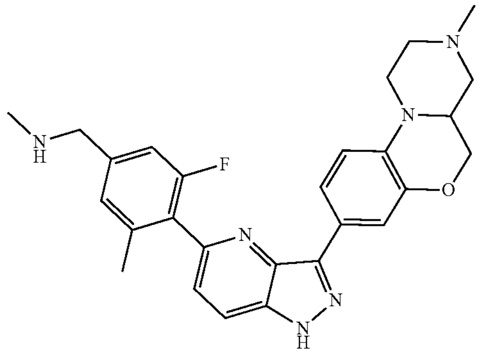
87
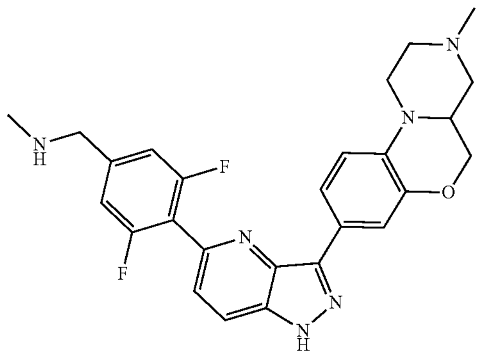
-continued
88
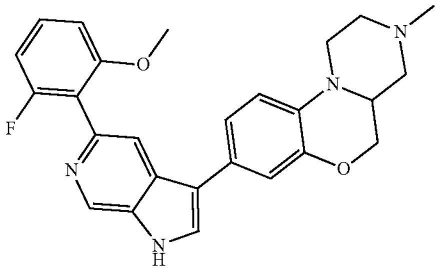
89
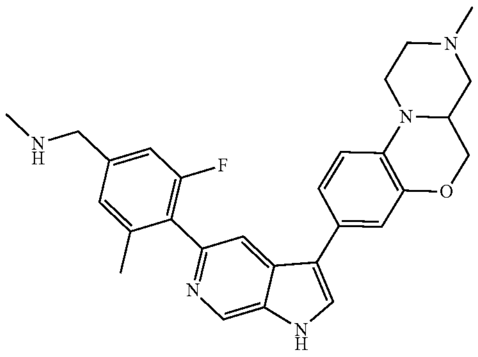
90
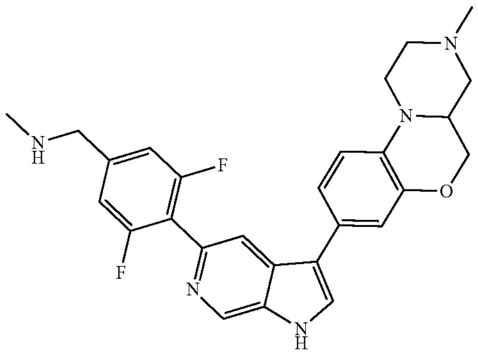
91
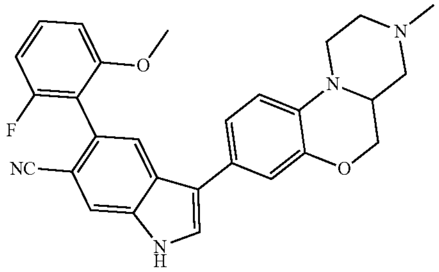

-continued
92
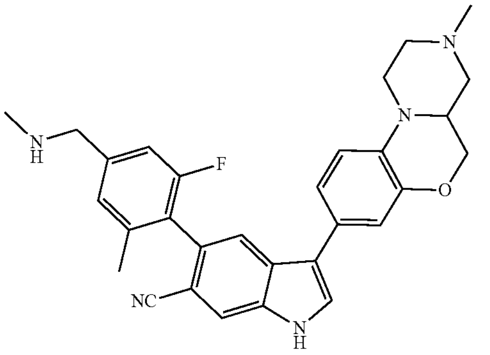
93
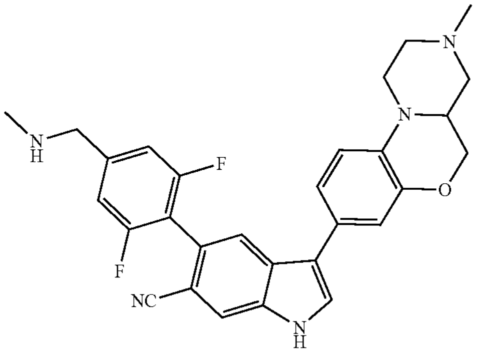
94
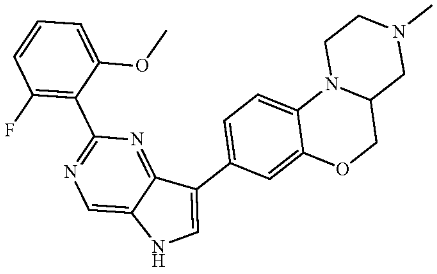
95
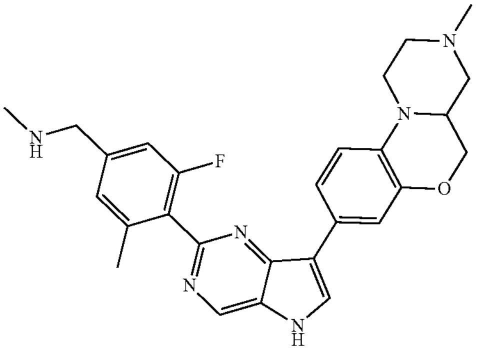
-continued
96
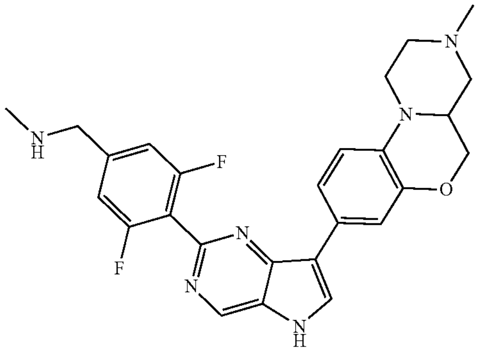
97
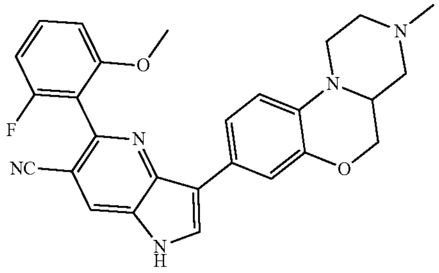
98
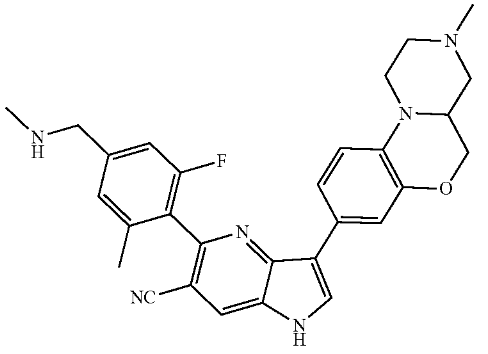
99
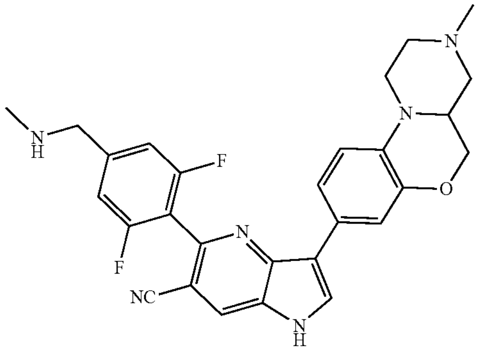

-continued
100
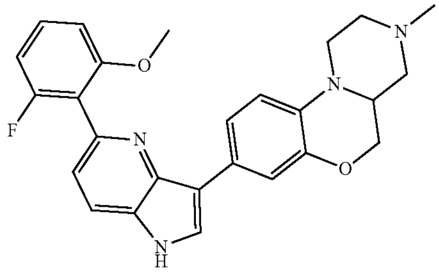
101
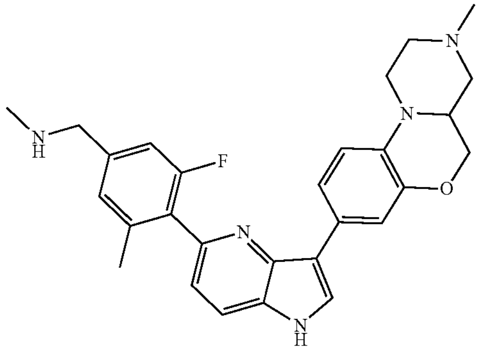
102
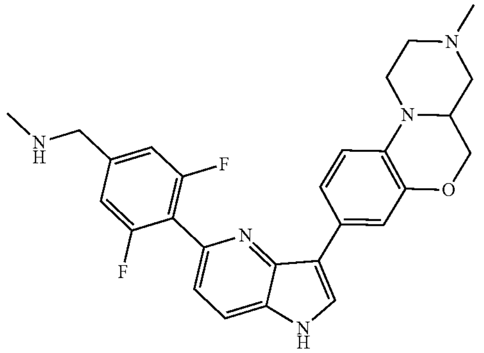
103
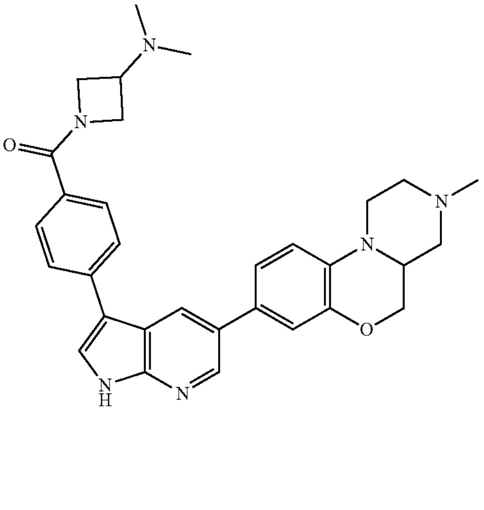
-continued
104
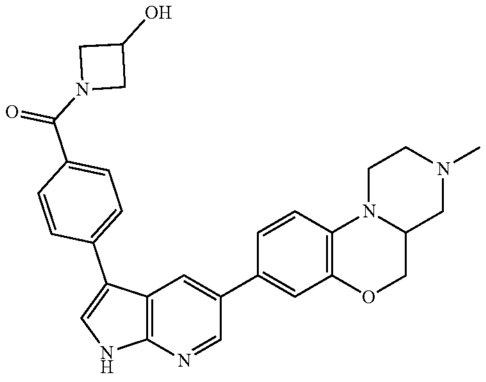
105
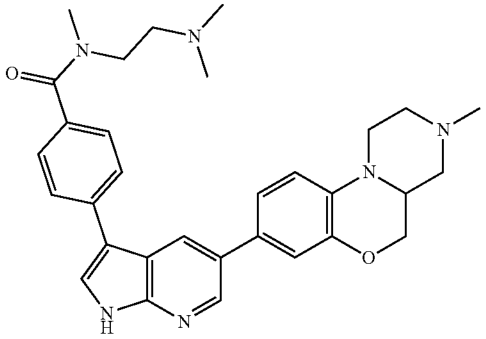
106
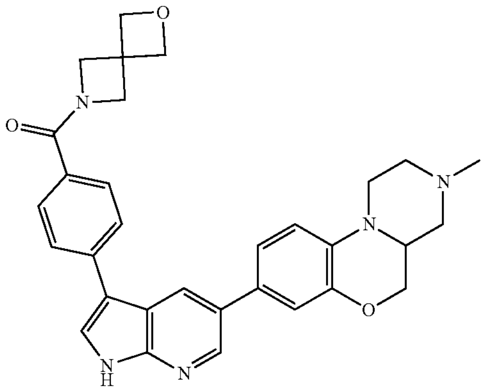
107
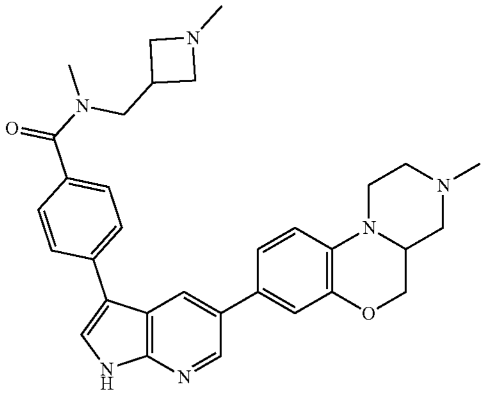

-continued
108
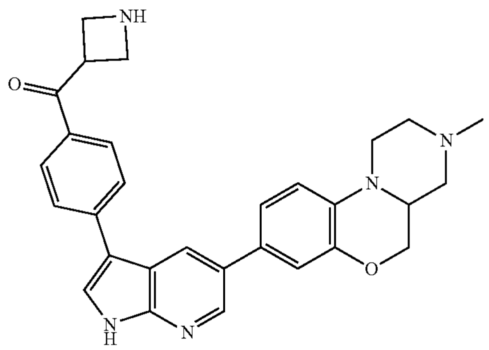
109
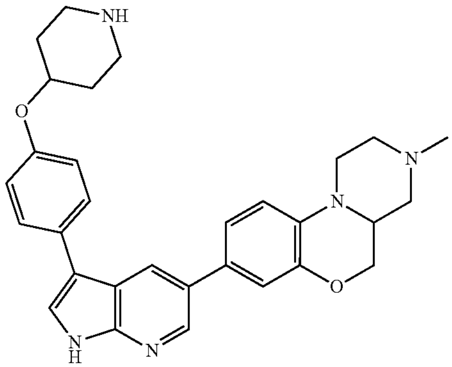
110
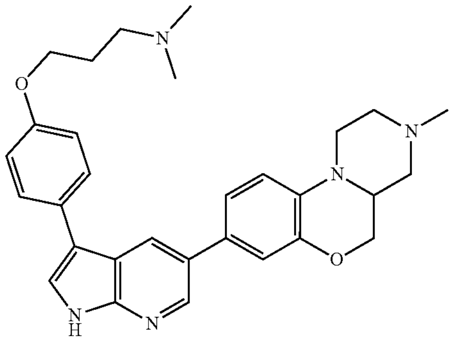
111
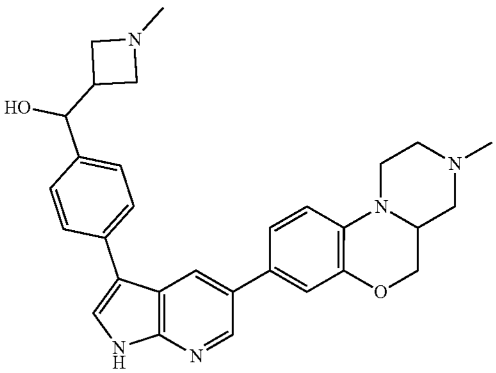
-continued
112
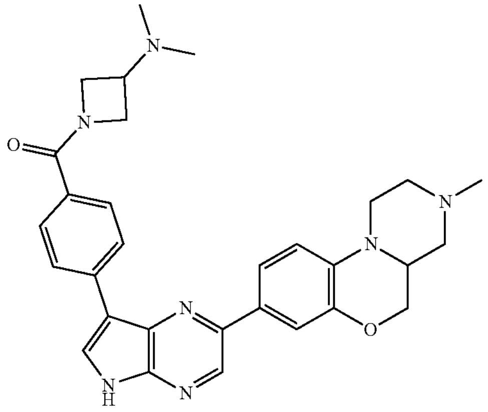
113
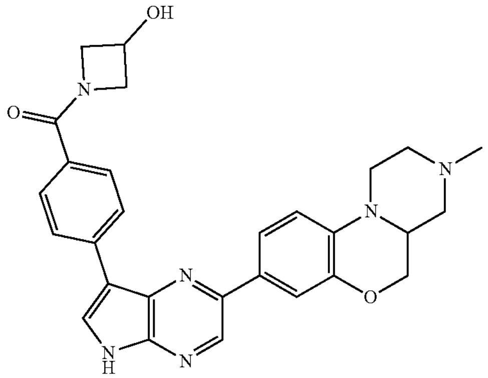
114
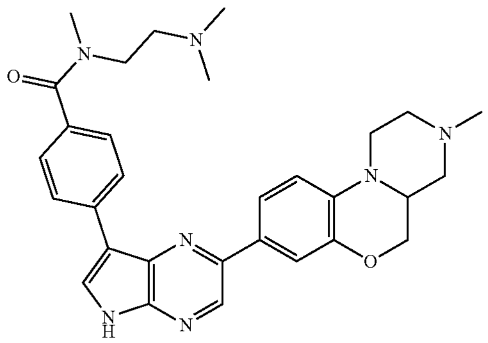
115
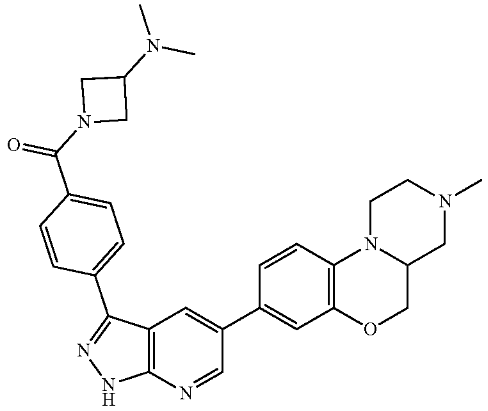

-continued
116
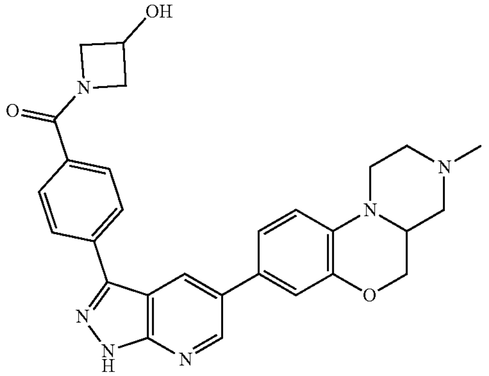
117
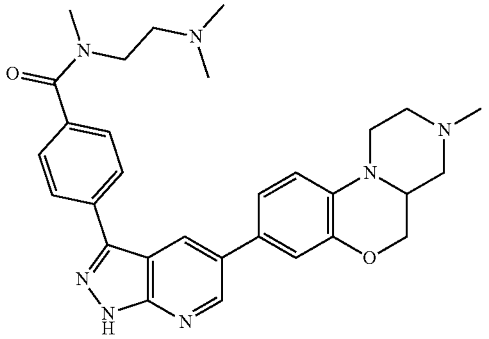
118
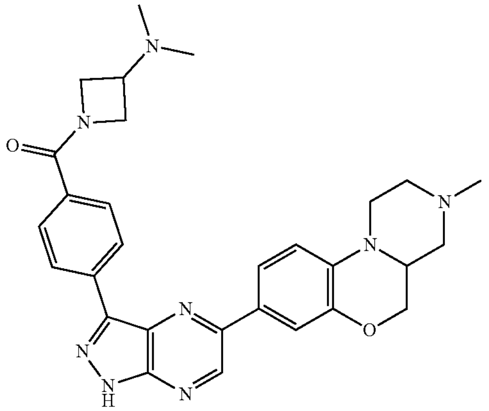
119
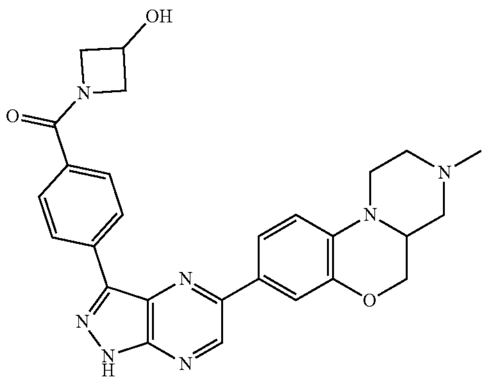
-continued
120
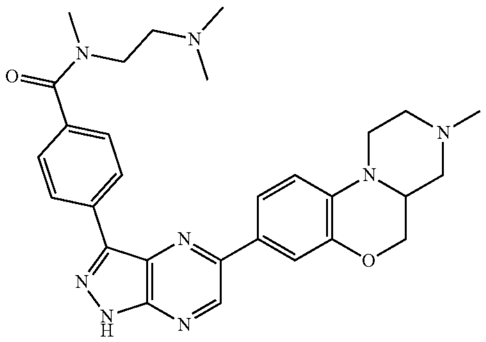
121
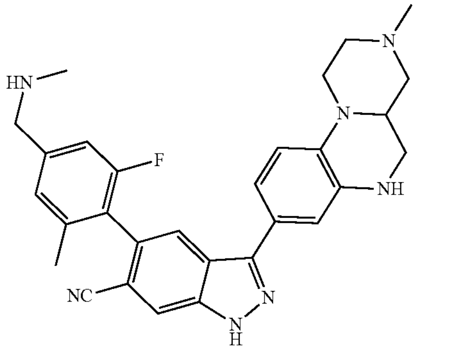
122
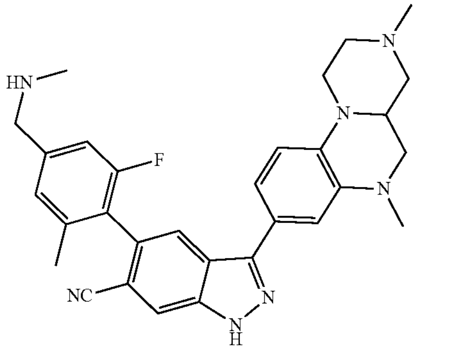
123
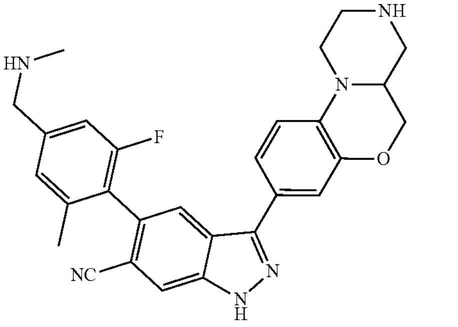

-continued

124

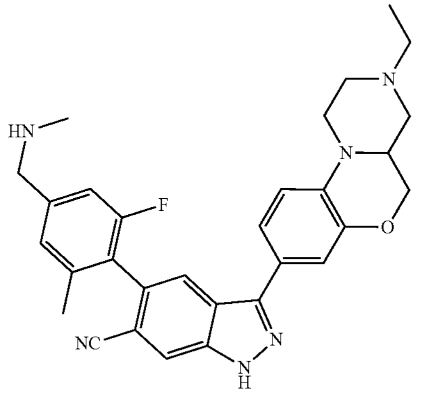

125

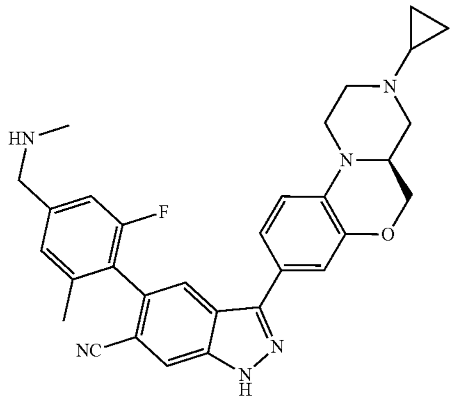

126

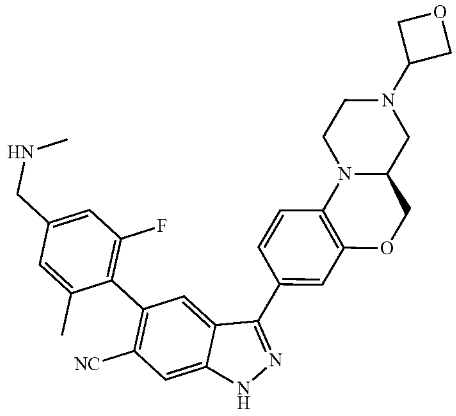

-continued

127

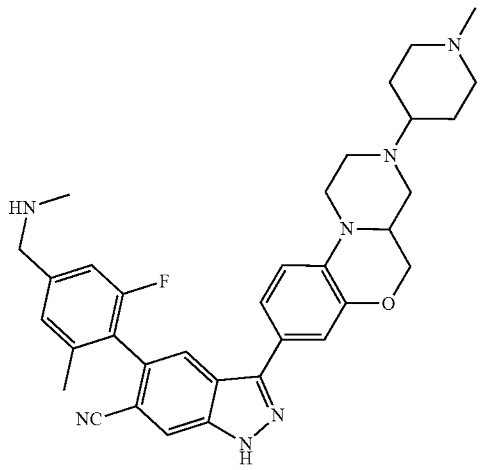

128

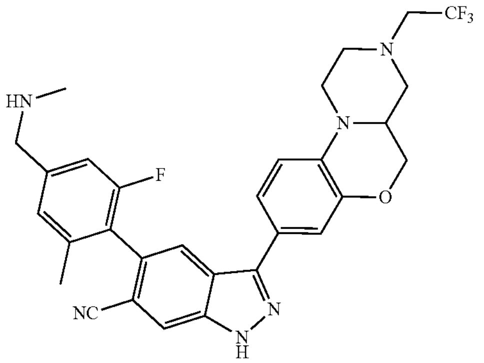

and

129

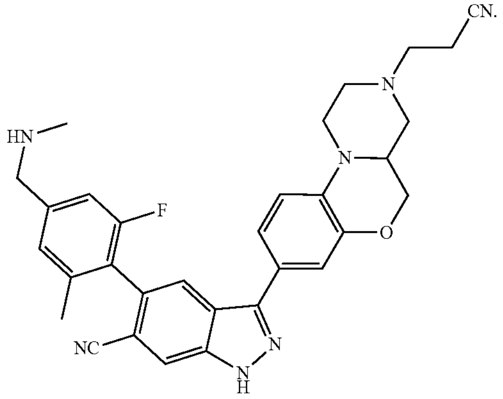

Another objective of the present invention is to provide a pharmaceutical composition comprising a pharmaceutically acceptable excipient or carrier, and the compound of general formula (1), or the isomers, the crystalline forms, the pharmaceutically acceptable salts, the hydrates or the solvates thereof disclosed herein as an active ingredient.

Still another objective of the present invention is to provide use of the above-mentioned compound, or the isomers, the crystalline forms, the pharmaceutically acceptable salts, the hydrates or the solvates thereof disclosed herein or the above-mentioned pharmaceutical composition disclosed herein in the preparation of a medicament for treating or preventing related diseases mediated by HPK1.

An objective of the present invention is to provide a method for treating an HPK1-mediated disease, which comprises administering to a subject the compound of general formula (1), or the isomers, the crystalline forms, the pharmaceutically acceptable salts, the hydrates or the solvates thereof disclosed herein or the above-mentioned pharmaceutical composition disclosed herein. The HPK1-mediated disease may be a cancer, and the cancer may be a hematological cancer or a solid tumor.

It should be understood that both the above general description and the following detailed description of the present invention are exemplary and explanatory, and are intended to provide further explanation of the present invention claimed.

Synthesis of the Compounds

Methods for preparing the compounds of general formulas (1) of the present invention are hereafter described in detail, but these specific methods do not limit the present invention in any way.

The compounds of general formulas (1) described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, Advanced Organic Chemistry, $4^{th}$ Ed., (Wiley 1992); Carey and Sundberg, Advanced Organic Chemistry, $4^{th}$ Ed., Vols. A and B (Plenum 2000, 2001), and Green and Wuts, Protective Groups in Organic Synthesis, $3^{rd}$ Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas (1), which are prepared using general reaction scheme 1 below:

General reaction scheme 1

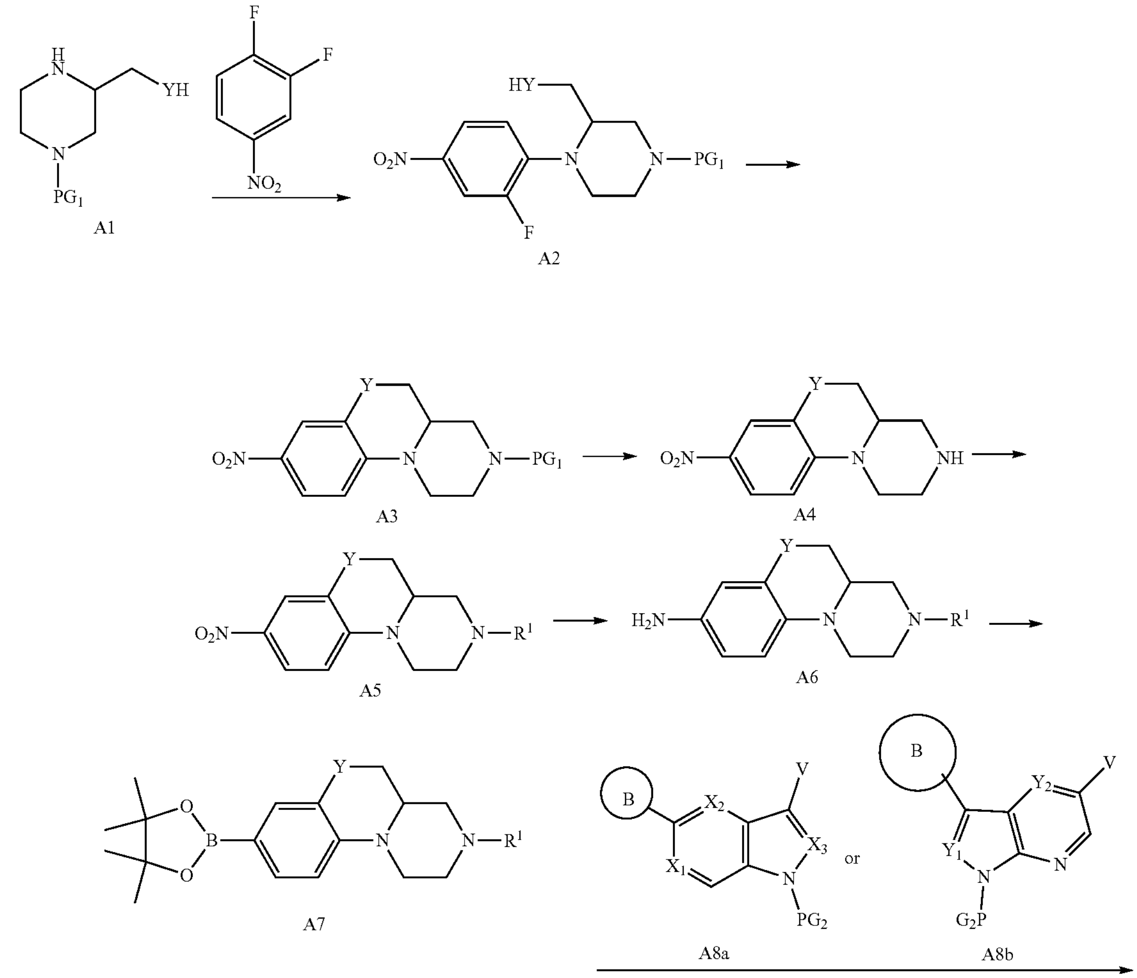

A1 A2

A3 A4

A5 A6

A7 A8a or A8b

-continued

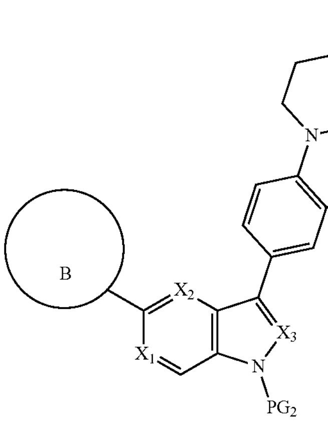

A9a or

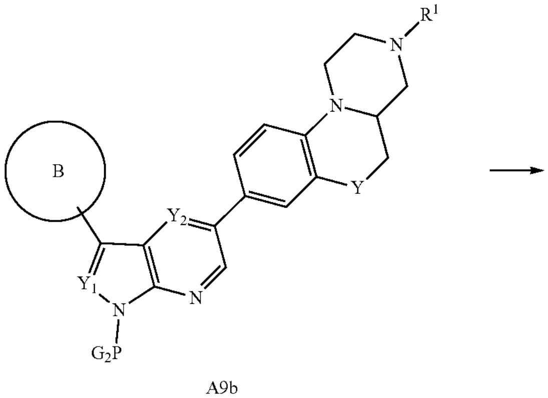

A9b

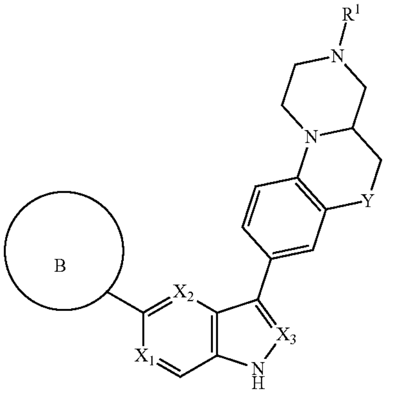

A810a or

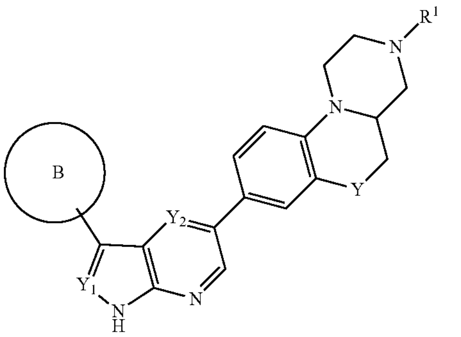

A10b

Embodiments of a compound of general formula (1) may be prepared according to general reaction scheme 1, wherein Y, $X_1$, $X_2$, $X_3$, $Y_1$, $Y_2$, $R^1$ and group B are as defined above, PG1 and PG2 denote protecting groups, and V denotes chlorine, bromine, iodine, OTf or the like. As shown in general reaction scheme 1, compound A1 and compound 3,4-difluoronitrobenzene react under a basic condition to obtain compound A2, compound A2 is cyclized under a strongly basic condition to obtain compound A3, compound A3 removes protecting group PG1 to obtain compound A4, compound A4 further reacts to obtain compound A5, compound A5 is subjected to nitro reduction to obtain compound A6, compound A6 is subjected to diazotization and bis (pinacolato)diboron reaction to obtain compound A7, compound A7 and compound A8a (or A8b) are subjected to coupling reaction to obtain compound A9a (or A9b), and compound A9a (or A9b) further removes protecting group PG2 to obtain target compound A10a (or A10b).

Further Forms of Compounds

"Pharmaceutically acceptable" herein refers to a substance, such as a carrier or diluent, which will not cause a compound to lose its biological activity or properties. It is relatively non-toxic; for example, when an individual is given a substance, it will not cause unwanted biological effects or interact with any component contained therein in a deleterious manner. The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by reacting the compounds of general formulas (1) with acids, e.g. inorganic acids such as hydrochloric acid, hydrobromic acid, hydrofluoric acid, sulfuric acid, phosphoric acid and nitric acid, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid and p-toluenesulfonic acid, and acidic amino acids such as aspartic acid and glutamic acid. It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compounds of general formulas (1) are conveniently prepared or formed according to the methods described herein. For example, the hydrates of the compounds of general formulas (1) are conveniently prepared by recrystallization from a mixed solvent of water/organic solvent, wherein the organic solvent used includes, but is not limited to, tetrahydrofuran, acetone, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compounds of general formulas (1) are prepared into different forms, including but not limited to amorphous, pulverized and nanoparticle forms. In addition, the compound of general formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compounds of general formulas (1) have axial chiralities and/or chiral centers and thus occur in the form of a racemate, racemic mixture, single enantiomer, diastereomeric compound and single diastereomer. Each of these axial chiralities will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain unnatural proportions of atomic isotopes at one or more of the atoms that constitute such the compound. For example, the compound may be labeled with radioactive isotopes, such as tritium ($^3H$), iodine-125 ($^{125}I$) and C-14 ($^{14}C$). For another example, deuterium can be used to substitute a hydrogen atom to form a deuterated compound, the bond formed by deuterium and carbon is stronger than that formed by common hydrogen and carbon, and compared with an undeuterated medicament, the deuterated medicament generally has the advantages of reducing toxic and side effects, increasing medicament stability, enhancing curative effect, prolonging in vivo half-life period of the medicament and the like. All isotopic variations of the compound of the present invention, whether radioactive or not, are intended to be encompassed within the scope of the present invention.

Terminology

Unless otherwise stated, the terms used in the present application, including those in the specification and claims, are defined as follows. It must be noted that in the specification and the appended claims, the singular forms "a" and "an" include plural meanings unless the context clearly indicates otherwise. Unless otherwise stated, conventional methods of mass spectrometry, nuclear magnetic resonance spectroscopy, HPLC, protein chemistry, biochemistry, recombinant DNA technology and pharmacology are used. In the present application, "or" or "and" is used to mean "and/or" unless otherwise stated.

Unless otherwise specified, "alkyl" refers to a saturated aliphatic hydrocarbon group, including linear and branched groups containing 1 to 6 carbon atoms. Lower alkyl containing 1 to 4 carbon atoms, such as methyl, ethyl, propyl, 2-propyl, n-butyl, isobutyl or tert-butyl, is preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH$, $^iPr$, $^nPr$, $^iBu$, $^nBu$ and $^tBu$.

Unless otherwise specified, "cycloalkyl" refers to a 3- to 6-membered all-carbon monocyclic aliphatic hydrocarbon group, wherein one or more of the rings may contain one or more double bonds, but none of them has a fully conjugated π-electron system. For example, cyclopropyl, cyclobutyl, cyclopentyl, cyclohexane, and cyclohexadiene.

Unless otherwise specified, "alkoxy" refers to an alkyl group that bonds to the rest of the molecule through an ether oxygen atom. Representative alkoxy groups are ones having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}PrO$, $^{n-}PrO$, $^{i-}BuO$, $^{n-}BuO$ and $^{t-}BuO$.

Unless otherwise specified, "heteroaryl" refers to an aromatic group containing one or more heteroatoms (O, S or N) and it is monocyclic or polycyclic; for example, a monocyclic heteroaryl ring fuses with one or more carbocyclic aromatic groups or other monocyclic heterocyclyl groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, tetrazolyl, furyl, thienyl, isoxazolyl, thiazolyl, oxazolyl, isothiazolyl, pyrrolyl, indolyl, benzimidazolyl, benzofuryl, benzothiazolyl, benzothienyl, benzoxazolyl, benzopyridyl, and pyrrolopyrimidinyl.

Unless otherwise specified, "heterocycloalkyl" refers to a saturated or partially unsaturated ring system group containing one or more heteroatoms (O, S or N), wherein the nitrogen and sulfur atoms are optionally oxidized, and the nitrogen atom is optionally quaternized as a ring atom. Unless otherwise stated, the "heterocycloalkyl" ring system may be a monocyclic, bicyclic, spiro or polycyclic ring system. "Heterocycloalkyl" may link to the rest of the molecule through one or more ring carbons or heteroatoms. Examples of "heterocycloalkyl" include, but are not limited to, pyrrolidine, piperidine, N-methylpiperidine, tetrahydroimidazole, pyrazolidine, butyrolactam, valerolactam, imidazolidinone, hydantoin, dioxolane, phthalimide, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, 2-azaspiro[3.3]heptane, etc.

Unless otherwise specified, "halogen" (or halo) refers to fluorine, chlorine, bromine, or iodine. The term "halo" (or "halogenated") before a group name indicates that the group is partially or fully halogenated, that is, substituted in any combination by F, Cl, Br or I, preferably by F or Cl.

Specific Pharmaceutical and Medical Terminology

The term "acceptable", as used herein, means that a formula component or an active ingredient does not unduly adversely affect a general therapeutic target's health.

The terms "treatment," "treatment course," or "therapy", as used herein, include alleviating, inhibiting, or ameliorating a symptom or condition of a disease; inhibiting the development of complications; ameliorating or preventing underlying metabolic syndrome; inhibiting the development of the disease or symptom, e.g., controlling the progression of the disease or condition; alleviating the disease or symptom; causing the disease or symptom to subside; alleviating a complication caused by the disease or symptom, or preventing or treating a sign caused by the disease or symptom. As used herein, a compound or pharmaceutical composition, when administered, can ameliorate a disease, symptom, or condition, particularly meaning ameliorating the severity, delaying the onset, slowing the progression, or reducing the duration of the disease. Fixed or temporary administration, or continuous or intermittent administration, may be attributed to or associated with the administration.

The "active ingredient" refers to compounds of general formulas (1) through (3), and pharmaceutically acceptable inorganic or organic salts of the compounds of general formulas (1) through (3). The compounds of the present invention may contain one or more asymmetric centers (axial chirality) and thus occur in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), is capable of inducing a desired pharmacological and/or physiological response by local and/or systemic action.

The term "administered, administering or administration" refers herein to the direct administration of the compound or composition, or the administration of a prodrug, derivative, analog or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range ±10%, 5%, 1%, or 0.5%. Alternatively, the term "about" indicates that the actual value falls within the acceptable standard error of a mean, as considered by those skilled in the art. All ranges, quantities, values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be construed as the significant digits indicated or the numerical value obtained using conventional rounding rules.

Unless otherwise defined in the specification, the scientific and technical terms used herein have the same meaning as commonly understood by those skilled in the art. Furthermore, the singular nouns used in the specification encompass their plural forms, unless contradicted by context; the plural nouns used also encompass their singular forms.

Therapeutic Use

The present invention provides a method for using the compound or pharmaceutical composition of the present invention to treat diseases, including but not limited to conditions involving G12C K-Ras, G12C H-Ras and/or G12C N-Ras mutations (e.g., cancer).

In some embodiments, a method for treating cancer is provided, the method comprising administering to an individual in need thereof an effective amount of a pharmaceutical composition of any of the aforementioned compounds of structural general formulas (1) through (3) protected. In some embodiments, the cancer is mediated by K-Ras, H-Ras and/or G12C N-Ras mutations. In other embodiments, the cancer is lung cancer, pancreatic cancer, colon cancer, MYH-associated polyposis, or colorectal cancer.

Route of Administration

The compound and the pharmaceutically acceptable salt thereof of the present invention can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, etc. When the compound of the present invention is administered, it may be administered orally, rectally, parenterally (intravenously, intramuscularly or subcutaneously) or topically. Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers. Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances.

Besides such inert diluents, the composition may also include adjuvants, such as wetting agents, emulsifiers, suspending agents, sweeteners, flavoring agents, and perfuming agents. Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds.

When the pharmaceutical composition is used, a safe and effective amount of the compound of the present invention is administered to a mammal (such as a human) to be treated, wherein the administration dose is a pharmaceutically effective administration dose. For a human weighing 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, 1H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio. The present invention adopts the following abbreviations: MeCN denotes acetonitrile; DCM denotes dichloromethane; DIPEA denotes diisopropylethylamine; dioxane denotes 1,4-dioxane; DMF denotes dimethylformamide; EA denotes ethyl acetate; h denotes hour; 12 denotes iodine; KOH denotes potassium hydroxide; $K_3PO_4$ denotes potassium phosphate; min denotes minute; MS denotes mass spectrum; $NaBH_3CN$ denotes sodium cyanoborohydride; NaH denotes sodium hydride; $NaHCO_3$ denotes sodium bicarbonate; $Na_2SO_4$ denotes sodium sulfate; NMR denotes nuclear magnetic resonance; Pd(dppf)$Cl_2$ denotes 1,1'-bis(diphenylphosphino)ferrocene]dichloropalladium; PE denotes petroleum ether; Sphos-Pd-G3 denotes methanesulfonic acid (2-dicyclohexylphosphino-2',6'-dimethoxy-1,1'-biphenyl)(2'-amino-1,1'-biphenyl-2-yl)palladium (II); TFA ($CF_3COOH$) denotes trifluoroacetic acid; TLC denotes thin layer chromatography.

DETAILED DESCRIPTION

Example 1 Synthesis of 5-(2-fluorophenyl)-3-(3-methyl-1,2,3,4,4a,5-hexahydrobenzo[b]pyrazino[1,2-d][1,4]oxazin-8-yl)-1H-indazole-6-carbonitrile (Compound 1)

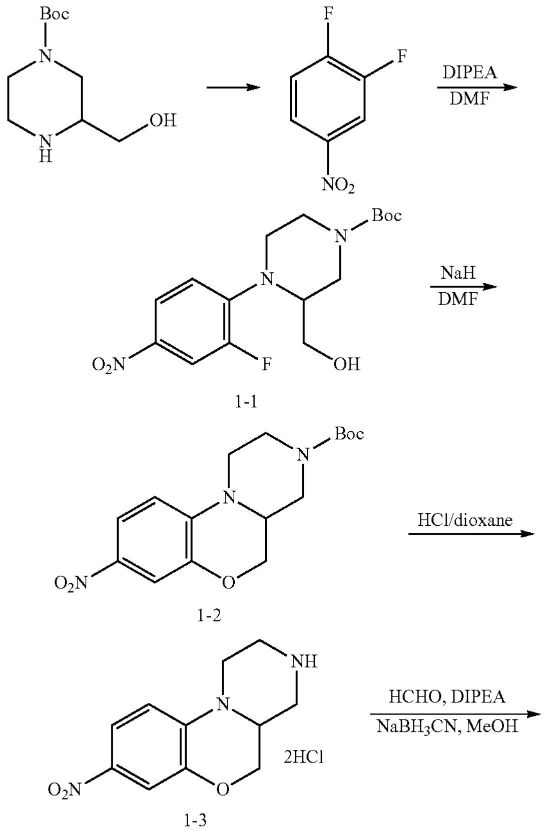

-continued

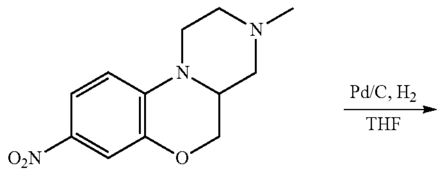

1-4

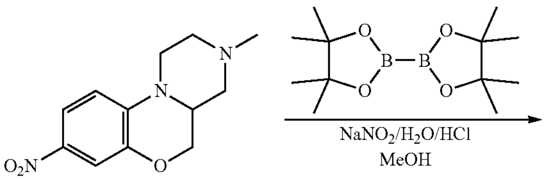

1-5

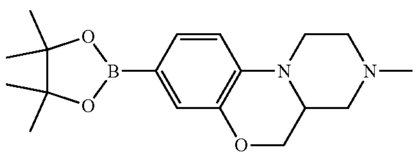

1-6

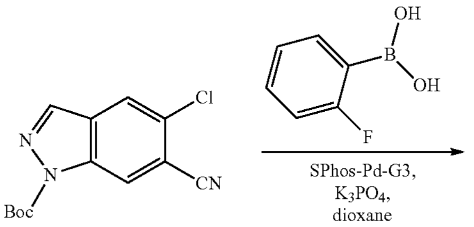

1-7

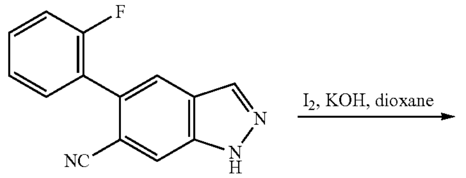

1-8

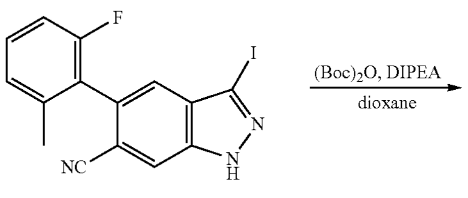

1-9

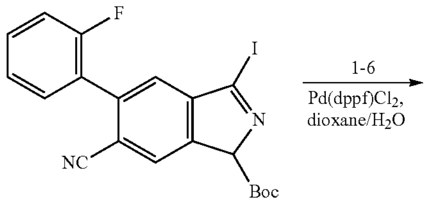

1-10

-continued

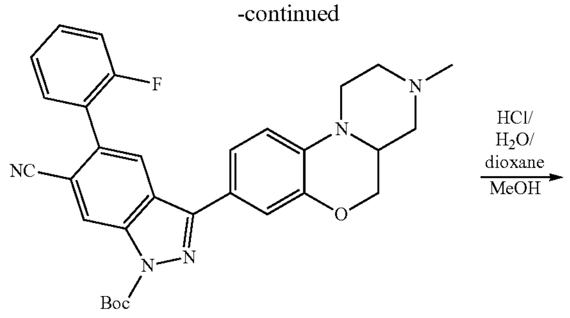

1-11

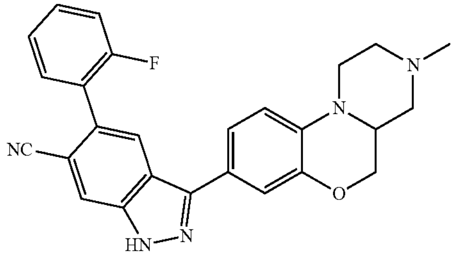

1

Step 1: Synthesis of Compound 1-1

Tert-butyl 3-hydroxymethylpiperazine-1-carboxylate (1.0 g, 4.63 mmol) and 1,2-difluoro-4-nitrobenzene (809 mg, 5.1 mmol) were dissolved in DMF (20 mL), DIPEA (1.8 g, 13.89 mmol) was added, and the reaction solution was heated to 120° C. and reacted overnight; after the completion of the reaction as detected by LC-MS, the reaction solution was added into water (100 mL) and extracted with EA (50 mL×3), the organic phases were combined, washed with water (50 mL), dried over anhydrous $Na_2SO_4$ and concentrated, and the resulting residue was purified by column chromatography (PE/EA=10/1 to 5/1) to obtain Compound 1-1 (1.0 g, yield 61%) in the form of a yellow solid, ESI-MS m/z: 356.1 $[M+H]^+$.

Step 2: Synthesis of Compound 1-2

Compound 1-1 (3.6 g, 10 mmol) was dissolved in DMF (30 mL), NaH (440 mg, 11 mmol) was added under ice-bath cooling, and the reaction solution was heated to 80° C. and reacted overnight; after the completion of the reaction as detected by LC-MS, the reaction solution was cooled, poured into ice water (100 mL) and extracted with EA (50 mL×2), the organic phases were combined, washed with water (150 mL×2) and saturated brine (50 mL) and concentrated, and the resulting residue was purified by column chromatography (PE/EA=20/1 to 10/1) to obtain Compound 1-2 (2.1 g, yield 62%) in the form of a yellow solid, ESI-MS m/z: 336.1 $[M+H]^+$.

Step 3: Synthesis of Compound 1-3

Compound 1-2 (2.0 g, 6.0 mmol) was dissolved in EA (40 mL), HCl/dioxane (4.0 M, 10 mL) was added, and the reaction solution was stirred at room temperature for 3 h; after the completion of the reaction as detected by LC-MS, the reaction solution was directly concentrated to obtain Compound 1-3 (2.0 g, yield 100%) in the form of a yellow solid, ESI-MS m/z: 236.1 $[M+H]^+$. The obtained initial product was directly used in the next step without purification.

Step 4: Synthesis of Compound 1-4

The crude product 1-3 obtained from the previous step was dissolved in MeCN (20 mL), aqueous formaldehyde (35%-40%, 0.5 mL) and HOAc (360 mg, 6.0 mmol) were added, and the reaction solution was stirred at room temperature for 1 h, added with $NaBH_3CN$ (0.76 g, 12 mmol) and reacted at room temperature overnight; after the completion of the reaction as detected by LC-MS, the reaction solution was concentrated, and the resulting residue was dissolved in EA (50 mL), washed with aqueous $NaHCO_3$ (50 mL), concentrated, and purified by column chromatography (DCM/MeOH=100/1 to 20/1) to obtain Compound 1-4 (1.0 g, yield 66%) in the form of a yellow solid, ESI-MS m/z: 250.1 $[M+H]^+$.

Step 5: Synthesis of Compound 1-5

Compound 1-4 (1.0 g, 4.0 mmol) was dissolved in MeOH (50 mL), Pd/C (10%, 200 mg) was added, and the reaction solution was purged with hydrogen and reacted at room temperature overnight; after the completion of the reaction as detected by LC-MS, the reaction solution was filtered and concentrated to obtain Compound 1-5 (800 mg, yield 91%) in the form of a pale yellow solid, ESI-MS m/z: 220.1 $[M+H]^+$. The obtained initial product was directly used in the next step without purification.

Step 6: Synthesis of Compound 1-6

Compound 1-5 (440 mg, 2 mmol) was dissolved in MeOH (4 mL), aqueous hydrochloric acid (3.0 M, 2 mL) and $NaNO_2$ (138 mg, 2 mmol) aqueous solution (1 mL) were added under an ice bath, and the reaction solution was stirred for 30 min under the ice bath, added with bis(pinacolato) diboron (1.52 g, 6 mmol) and stirred for 1 h; after the completion of the reaction as detected by LC-MS, the reaction solution was added with aqueous $NaHCO_3$ to quench the reaction and extracted with DCM (50 mL×2), the organic phase was dried over anhydrous $Na_2SO_4$ and concentrated, and the resulting residue was purified by column chromatography (DCM/MeOH=50/1 to 20/1) to obtain Compound 1-6 (500 mg, yield 75%) in the form of a pale yellow gum, ESI-MS m/z: 331.1$[M+H]^+$.

Step 7: Synthesis of Compound 1-8

Tert-butyl 5-chloro-6-cyano-1H-indazole-1-carboxylate (2.78 g, 10 mmol) and 2-fluorobenzeneboronic acid (1.40 g, 10 mmol) were dissolved in 1,4-dioxane/$H_2O$ (v/v=5/1, 30 mL), $K_3PO_4$ (4.24 g, 20 mmol) and Pd XPhos G3 (423 mg, 0.05 mmol) were added, and the reaction solution was heated to 90° C. in argon atmosphere for 5 h; after the completion of the reaction as detected by LC-MS, the reaction solution was cooled, diluted with EA (50 mL) and washed with water (50 mL×2), the organic phase was concentrated, and the resulting residue was purified by column chromatography (PE/EA=20/1 to 5/1) to obtain Compound 1-8 (0.83 g, yield 35%) in the form of a pale yellow solid, ESI-MS m/z: 238.1 $[M+H]^+$.

Step 8: Synthesis of Compound 1-9

Compound 1-8 (474 mg, 2 mmol) was dissolved in DMF (10 mL), KOH (280 mg, 5 mmol) and 12 (760 mg, 3 mmol) were added, and the reaction solution was stirred at room temperature for 2 h; after the completion of the reaction as detected by LC-MS, the reaction solution was cooled to room temperature, added with 1 N hydrochloric acid to adjust pH to about 7, and then added with EA/$H_2O$ (50 mL/50 mL), followed by liquid separation, the aqueous phase was extracted with EA (50 mL×2), the organic phases were combined and concentrated under reduced pressure, and the resulting residue was purified by column chromatography (PE/EA=10/1 to 2/1) to obtain Compound 1-9 (425 mg, yield 56%) in the form of a pale yellow solid, ESI-MS m/z: 378.2 $[M+H]^+$.

Step 9: Synthesis of Compound 1-10

Compound 1-9 (377 mg, 1.0 mmol) was dissolved in DCM (20 mL), TEA (202 mg, 2.0 mmol) was added, $(Boc)_2O$ (262 mg, 1.2 mmol) was finally added, and the reaction solution was stirred at room temperature for 3 h; after the completion of the reaction as detected by LC-MS, the reaction solution was added with EA/$H_2O$ (50 mL/50 mL), followed by liquid separation, the organic phase was concentrated, and the resulting residue was purified by column chromatography (PE/EA=20/1 to 10/1) to obtain Compound 1-10 (402 mg, yield 87%) in the form of a pale yellow solid, ESI-MS m/z: 464.3 $[M+H]^+$.

Step 10: Synthesis of Compound 1-11

Compound 1-10 (232 mg, 0.5 mmol) and Compound 1-6 (198 mg, 0.6 mmol) were dissolved in 1,4-dioxane/$H_2O$ (v/v=5/1, 10 mL), $K_3PO_4$ (212 mg, 1.0 mmol) and $Pd(dppf)_2C_1$ (73 mg, 0.1 mmol) were added, and the reaction solution was heated at 90° C. in argon atmosphere for 5 h; after the completion of the reaction as detected by LC-MS, the reaction solution was cooled, diluted with EA (50 mL) and washed with water (20 mL×1), the organic phase was concentrated, and the resulting residue was purified by column chromatography (DCM/MeOH=50/1 to 20/1) to obtain Compound 1-11 (168 mg, yield 62%) in the form of a pale yellow solid, ESI-MS m/z: 540.2 $[M+H]^+$.

Step 11: Synthesis of Compound 1

Compound 1-11 (162 mg, 0.3 mmol) was dissolved in HCl/dioxane (4.0 N, 2 mL), and the reaction solution was reacted at room temperature for 3 h; after the completion of the reaction as detected by LC-MS, the reaction solution was concentrated directly, the resulting residue was dissolved in DCM (50 mL), added with aqueous $NaHCO_3$ to give a basic pH, followed by layer separation, the organic phase was dried over anhydrous $Na_2SO_4$ and concentrated, and the resulting residue was purified by column chromatography (DCM/MeOH=50/1 to 20/1) to obtain Compound 1 (96 mg, yield 73%) in the form of a pale yellow solid.

$^1H$ NMR (400 MHz, DMSO-$d_6$) δ: 8.36 (s, 1H), 8.21 (s, 1H), 7.78-7.70 (m, 2H), 7.52 (d, J=8.8 Hz, 1H), 7.42-7.32 (m, 2H), 7.23 (dd, J=10.0, 5.3 Hz, 1H), 6.98 (d, J=8.7 Hz, 1H), 4.29-4.16 (m, 1H), 3.91 (t, J=9.7 Hz, 1H), 3.66-3.72 (m, 1H), 3.09 (s, 1H), 2.85 (d, J=10.3 Hz, 1H), 2.79 (d, J=10.9 Hz, 1H), 2.71-2.62 (m, 1H), 2.19 (s, 3H), 2.13-2.00 (m, 1H), 1.72 (t, J=10.7 Hz, 1H), ESI-MS m/z: 440.2 $[M+H]^+$.

Tert-butyl (S)-3-hydroxymethylpiperazine-1-carboxylate or tert-butyl (R)-3-hydroxymethylpiperazine-1-carboxylate was taken as a starting material, and the synthesis of Compound 1 can obtain two optical isomers 1-a and 1-b of Compound 1:

1-a

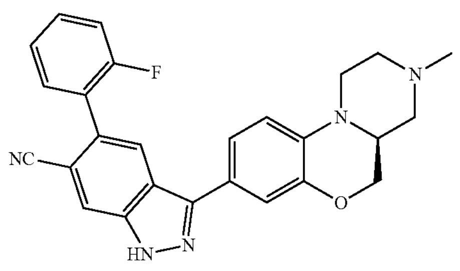

-continued
1-b
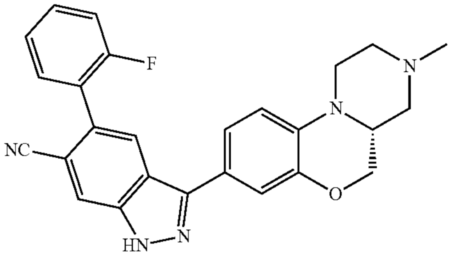
Examples 2-129: Synthesis of Compounds 2-129
The target compounds 2-129 were obtained according to a similar synthesis method as in Example 1 using different starting materials.
TABLE 1
| Compound | Structure of compound | $[M + H]^+$ |
| --- | --- | --- |
| 2 | 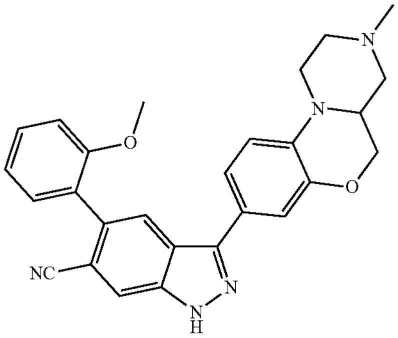 [SMILES: COc1ccccc1-c1cc2c(-c3ccc4c(c3)OCC3CN(C)CCN43)n[nH]c2cc1C#N] | 452.2 |
| 3 | 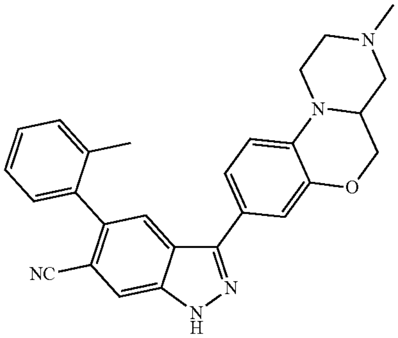 [SMILES: Cc1ccccc1-c1cc2c(-c3ccc4c(c3)OCC3CN(C)CCN43)n[nH]c2cc1C#N] | 436.2 |
| 4 | 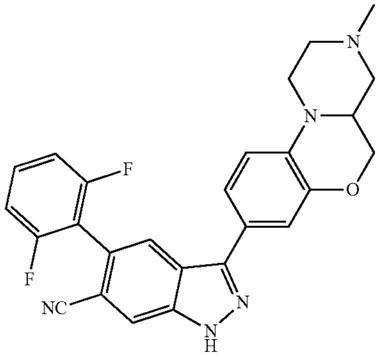 | 458.2 |

TABLE 1-continued
| Compound | Structure of compound | [M + H]$^+$ |
|---|---|---|
| 5 | 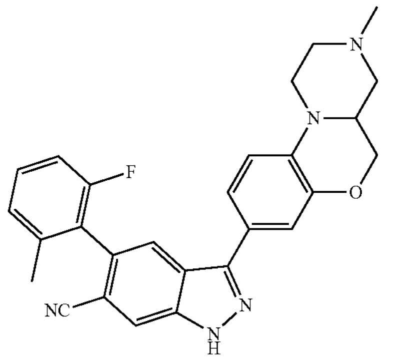 [SMILES: Cc1cccc(F)c1-c1cc2c(-c3ccc4c(c3)OCC3CN(C)CCN43)n[nH]c2cc1C#N] | 454.2 |
| 6 | 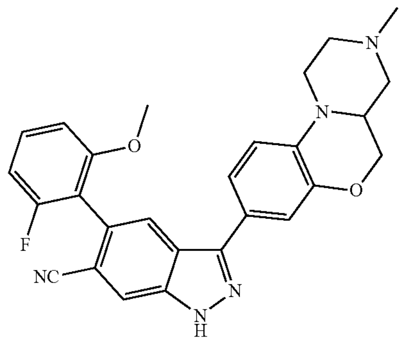 [SMILES: COc1cccc(F)c1-c1cc2c(-c3ccc4c(c3)OCC3CN(C)CCN43)n[nH]c2cc1C#N] | 470.2 |
| 7 | 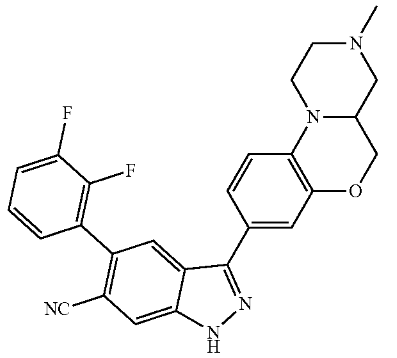 [SMILES: CN1CCN2c3ccc(-c4n[nH]c5cc(C#N)c(-c6cccc(F)c6F)cc45)cc3OCC2C1] | 458.2 |
| 8 | 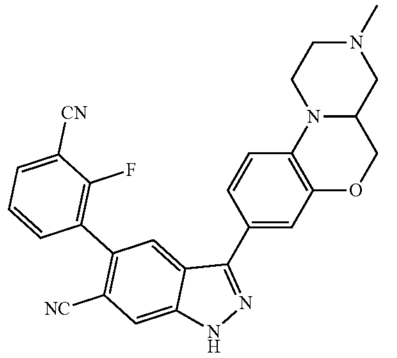 [SMILES: CN1CCN2c3ccc(-c4n[nH]c5cc(C#N)c(-c6cccc(C#N)c6F)cc45)cc3OCC2C1] | 465.2 |

TABLE 1-continued
| Compound | Structure of compound | [M + H]+ |
|---|---|---|
| 9 | 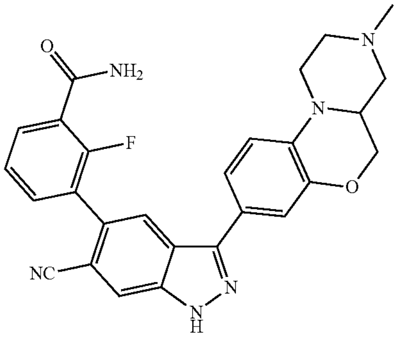 [SMILES: CN1CCN2c3ccc(-c4n[nH]c5cc(C#N)c(-c6cccc(C(N)=O)c6F)cc45)cc3OCC2C1] | 483.2 |
| 10 | 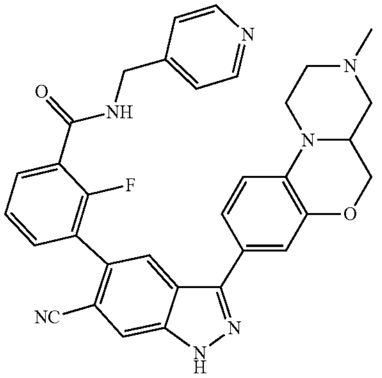 [SMILES: CN1CCN2c3ccc(-c4n[nH]c5cc(C#N)c(-c6cccc(C(=O)NCc7ccncc7)c6F)cc45)cc3OCC2C1] | 574.2 |
| 11 | 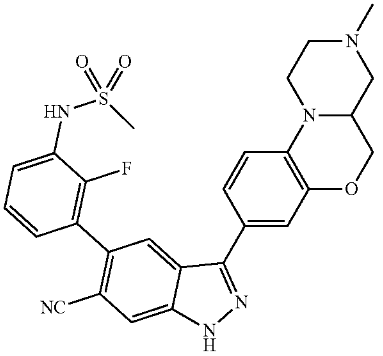 [SMILES: CN1CCN2c3ccc(-c4n[nH]c5cc(C#N)c(-c6cccc(NS(C)(=O)=O)c6F)cc45)cc3OCC2C1] | 533.2 |
| 12 | 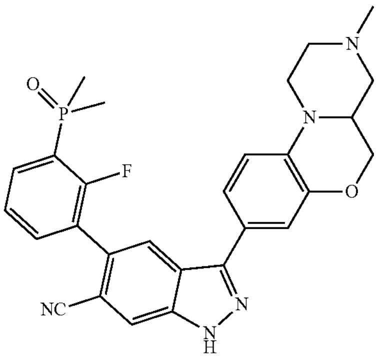 [SMILES: CN1CCN2c3ccc(-c4n[nH]c5cc(C#N)c(-c6cccc(P(C)(C)=O)c6F)cc45)cc3OCC2C1] | 516.2 |

TABLE 1-continued
| Compound | Structure of compound | [M + H]$^+$ |
|---|---|---|
| 13 | 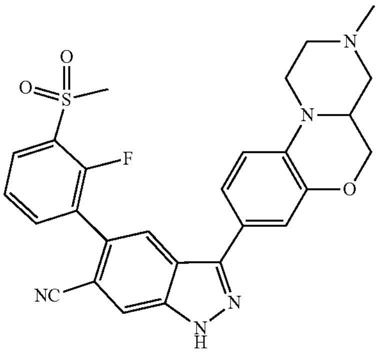 [SMILES: CN1CCN2c3ccc(-c4n[nH]c5cc(C#N)c(-c6cccc(S(C)(=O)=O)c6F)cc45)cc3OCC2C1] | 518.2 |
| 14 | 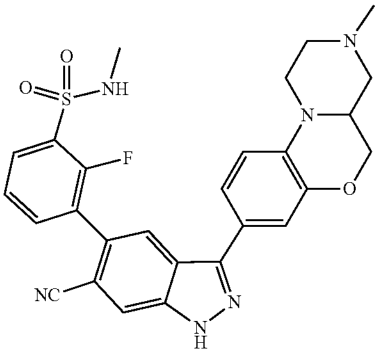 [SMILES: CNS(=O)(=O)c1cccc(-c2cc3c(-c4ccc5c(c4)OCC4CN(C)CCN54)n[nH]c3cc2C#N)c1F] | 533.2 |
| 15 | 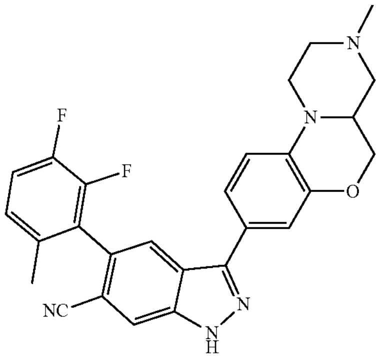 [SMILES: Cc1ccc(F)c(F)c1-c1cc2c(-c3ccc4c(c3)OCC3CN(C)CCN43)n[nH]c2cc1C#N] | 472.2 |
| 16 | 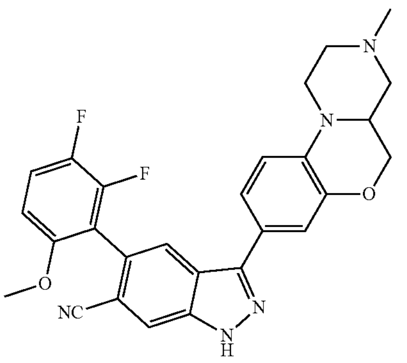 | 488.2 |

TABLE 1-continued
| Compound | Structure of compound | [M + H]+ |
|---|---|---|
| 17 | 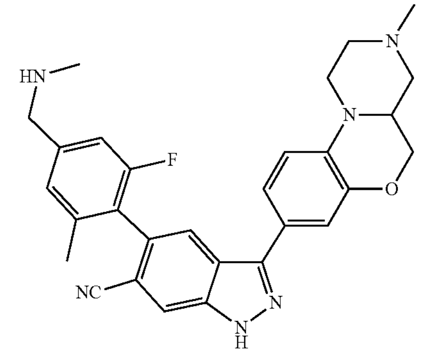 [SMILES: CNCc1cc(C)c(-c2cc3c(-c4ccc5c(c4)OCC4CN(C)CCN54)n[nH]c3cc2C#N)c(F)c1] | 497.2 |
| 18 | 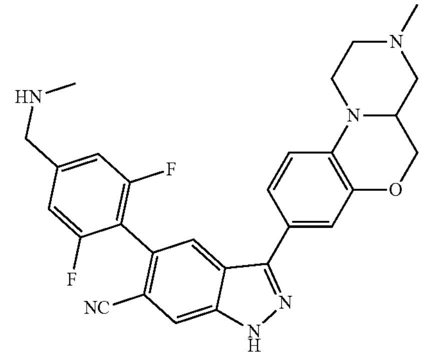 [SMILES: CNCc1cc(F)c(-c2cc3c(-c4ccc5c(c4)OCC4CN(C)CCN54)n[nH]c3cc2C#N)c(F)c1] | 501.2 |
| 19 | 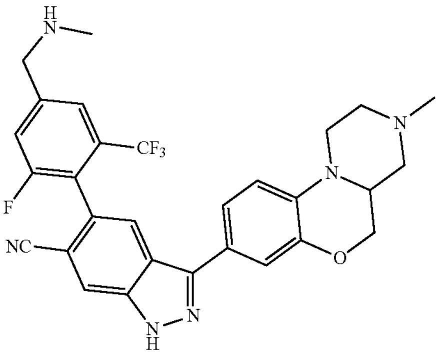 [SMILES: CNCc1cc(F)c(-c2cc3c(-c4ccc5c(c4)OCC4CN(C)CCN54)n[nH]c3cc2C#N)c(C(F)(F)F)c1] | 551.2 |
| 20 | 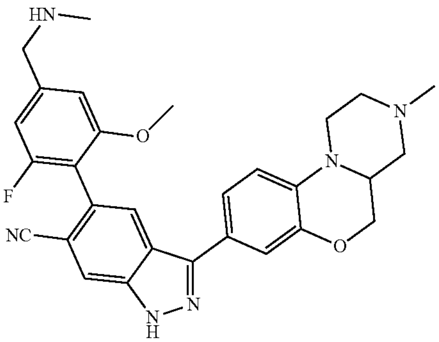 [SMILES: CNCc1cc(F)c(-c2cc3c(-c4ccc5c(c4)OCC4CN(C)CCN54)n[nH]c3cc2C#N)c(OC)c1] | 513.2 |

TABLE 1-continued
| Compound | Structure of compound | [M + H]$^+$ |
|---|---|---|
| 21 | 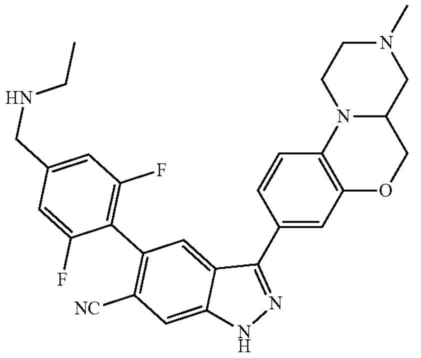 [SMILES: CCNCc1cc(F)c(-c2cc3c(-c4ccc5c(c4)OCC4CN(C)CCN54)n[nH]c3cc2C#N)c(F)c1] | 515.2 |
| 22 | 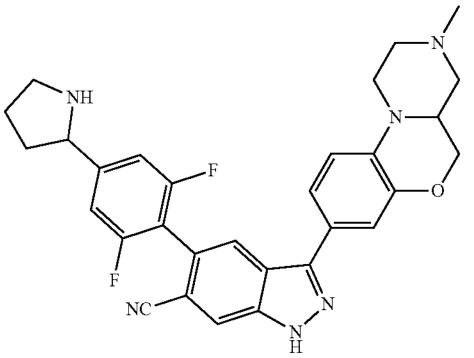 [SMILES: CN1CCN2c3ccc(-c4n[nH]c5cc(C#N)c(-c6c(F)cc(C7CCCN7)cc6F)cc45)cc3OCC2C1] | 517.2 |
| 23 | 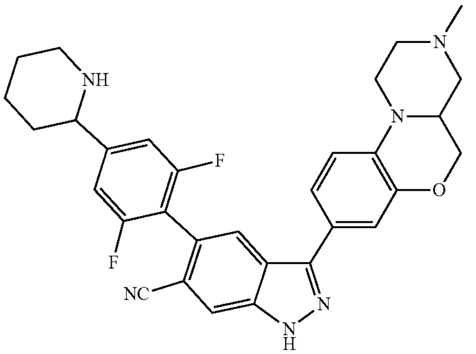 [SMILES: CN1CCN2c3ccc(-c4n[nH]c5cc(C#N)c(-c6c(F)cc(C7CCCCN7)cc6F)cc45)cc3OCC2C1] | 541.2 |
| 24 | 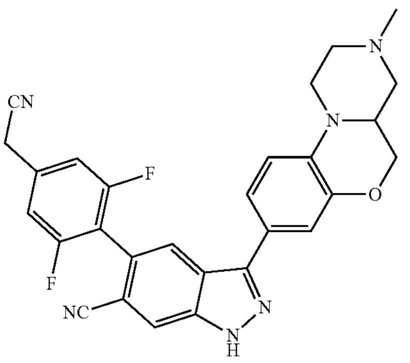 [SMILES: CN1CCN2c3ccc(-c4n[nH]c5cc(C#N)c(-c6c(F)cc(CC#N)cc6F)cc45)cc3OCC2C1] | 497.2 |

TABLE 1-continued
| Compound | Structure of compound | [M + H]+ |
|---|---|---|
| 25 | 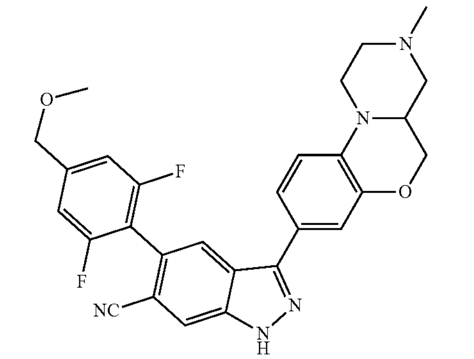 [SMILES: COCc1cc(F)c(-c2cc3c(-c4ccc5c(c4)OCC4CN(C)CCN54)n[nH]c3cc2C#N)c(F)c1] | 502.2 |
| 26 | 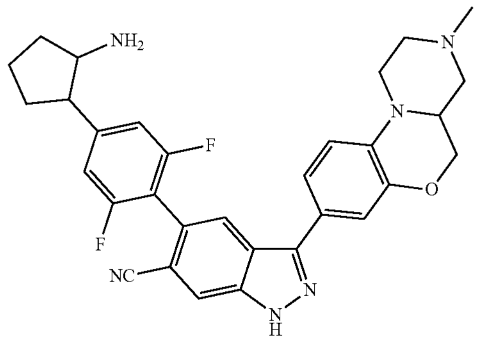 [SMILES: CN1CCN2c3ccc(-c4n[nH]c5cc(C#N)c(-c6c(F)cc(C7CCCC7N)cc6F)cc45)cc3OCC2C1] | 541.2 |
| 27 | 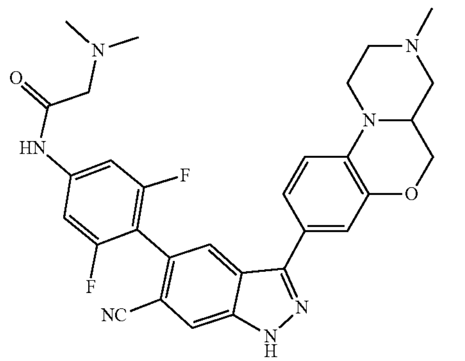 [SMILES: CN(C)CC(=O)Nc1cc(F)c(-c2cc3c(-c4ccc5c(c4)OCC4CN(C)CCN54)n[nH]c3cc2C#N)c(F)c1] | 558.2 |
| 28 | 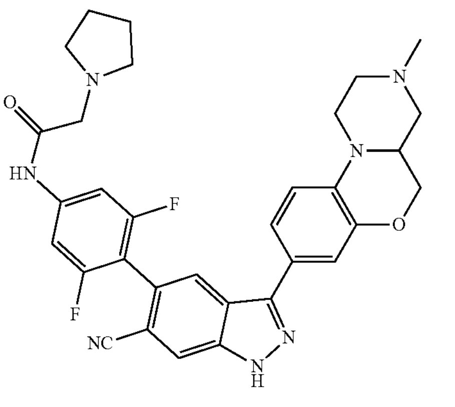 [SMILES: CN1CCN2c3ccc(-c4n[nH]c5cc(C#N)c(-c6c(F)cc(NC(=O)CN7CCCC7)cc6F)cc45)cc3OCC2C1] | 584.3 |

TABLE 1-continued
| Compound | Structure of compound | [M + H]+ |
| --- | --- | --- |
| 29 | 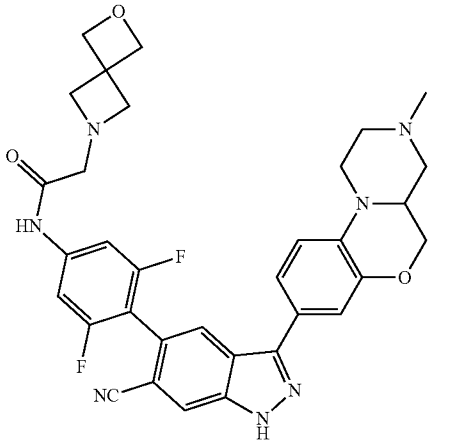 [SMILES: CN1CCN2c3ccc(-c4n[nH]c5cc(C#N)c(-c6c(F)cc(NC(=O)CN7CC8(COC8)C7)cc6F)cc45)cc3OCC2C1] | 612.3 |
| 30 | 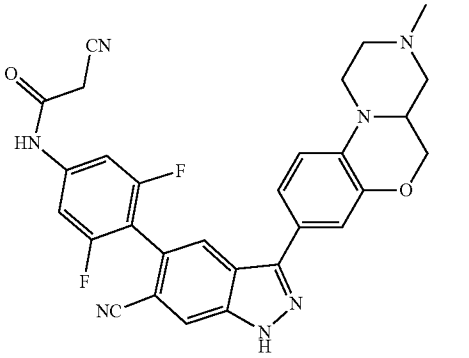 [SMILES: CN1CCN2c3ccc(-c4n[nH]c5cc(C#N)c(-c6c(F)cc(NC(=O)CC#N)cc6F)cc45)cc3OCC2C1] | 540.2 |
| 31 | 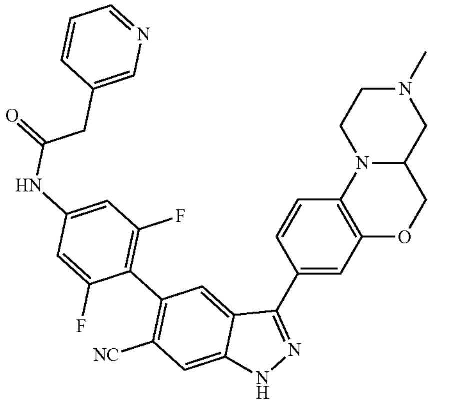 [SMILES: CN1CCN2c3ccc(-c4n[nH]c5cc(C#N)c(-c6c(F)cc(NC(=O)Cc7cccnc7)cc6F)cc45)cc3OCC2C1] | 592.2 |
| 32 | 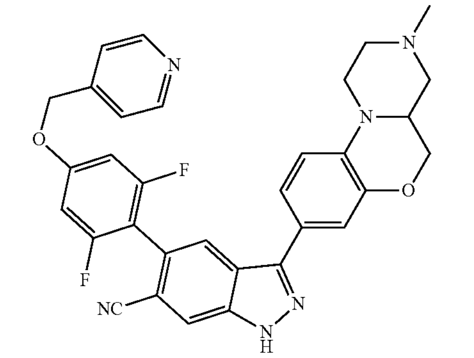 [SMILES: CN1CCN2c3ccc(-c4n[nH]c5cc(C#N)c(-c6c(F)cc(OCc7ccncc7)cc6F)cc45)cc3OCC2C1] | 565.2 |

TABLE 1-continued
| Compound | Structure of compound | [M + H]+ |
|---|---|---|
| 33 | 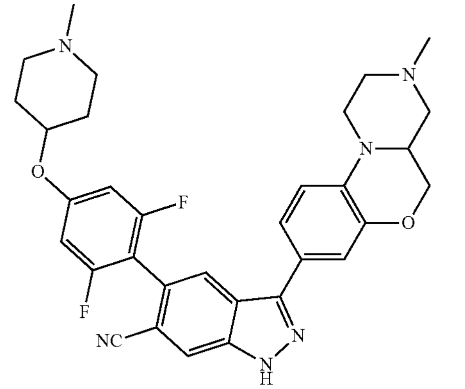 [SMILES: CN1CCC(Oc2cc(F)c(-c3cc4c(-c5ccc6c(c5)OCC5CN(C)CCN65)n[nH]c4cc3C#N)c(F)c2)CC1] | 571.3 |
| 34 | 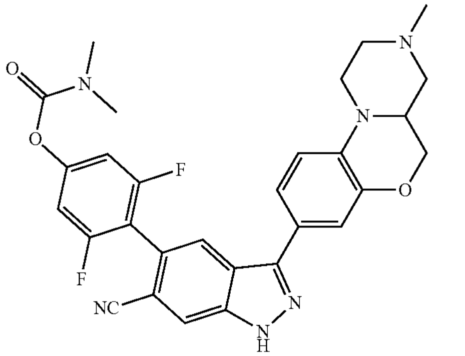 [SMILES: CN1CCN2c3ccc(-c4n[nH]c5cc(C#N)c(-c6c(F)cc(OC(=O)N(C)C)cc6F)cc45)cc3OCC2C1] | 545.2 |
| 35 | 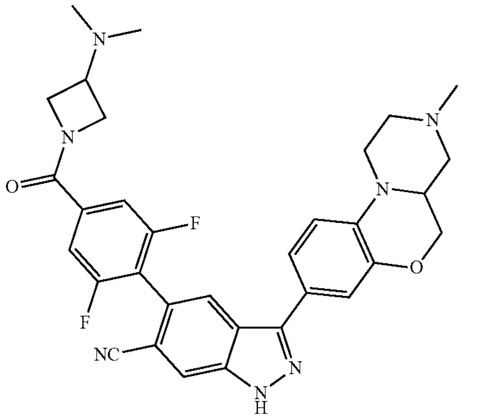 [SMILES: CN1CCN2c3ccc(-c4n[nH]c5cc(C#N)c(-c6c(F)cc(C(=O)N7CC(N(C)C)C7)cc6F)cc45)cc3OCC2C1] | 584.3 |
| 36 | 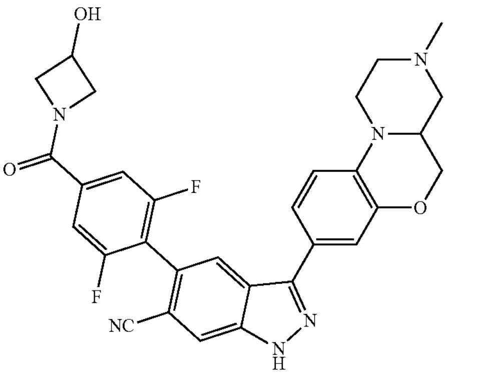 [SMILES: CN1CCN2c3ccc(-c4n[nH]c5cc(C#N)c(-c6c(F)cc(C(=O)N7CC(O)C7)cc6F)cc45)cc3OCC2C1] | 557.2 |

TABLE 1-continued
| Compound | Structure of compound | [M + H]+ |
|---|---|---|
| 37 | 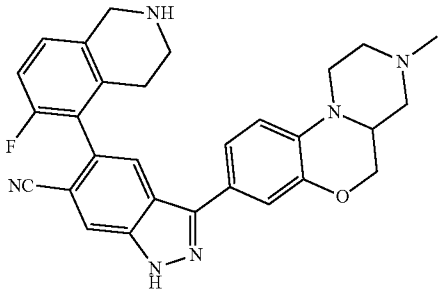 [SMILES: CN1CCN2c3ccc(-c4n[nH]c5cc(C#N)c(-c6c(F)ccc7c6CCNC7)cc45)cc3OCC2C1] | 495.2 |
| 38 | 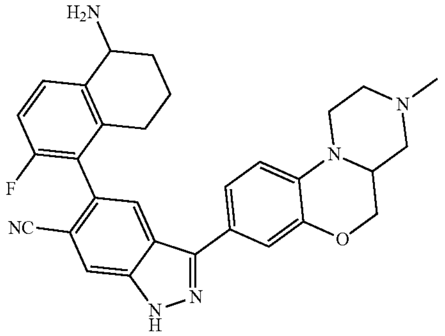 [SMILES: CN1CCN2c3ccc(-c4n[nH]c5cc(C#N)c(-c6c(F)ccc7c6CCCC7N)cc45)cc3OCC2C1] | 509.2 |
| 39 | 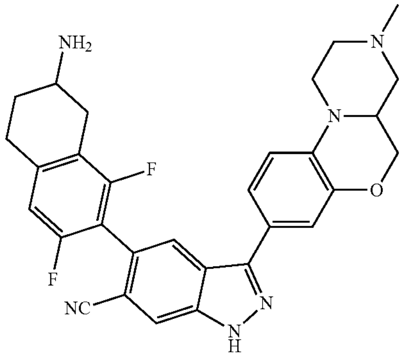 [SMILES: CN1CCN2c3ccc(-c4n[nH]c5cc(C#N)c(-c6c(F)cc7c(c6F)CC(N)CC7)cc45)cc3OCC2C1] | 526.2 |
| 40 | 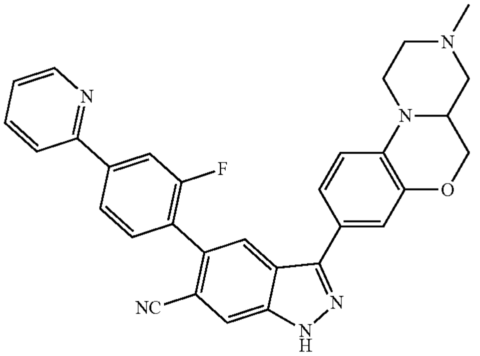 [SMILES: CN1CCN2c3ccc(-c4n[nH]c5cc(C#N)c(-c6ccc(-c7ccccn7)cc6F)cc45)cc3OCC2C1] | 517.2 |

TABLE 1-continued
| Compound | Structure of compound | [M + H]+ |
| --- | --- | --- |
| 41 | 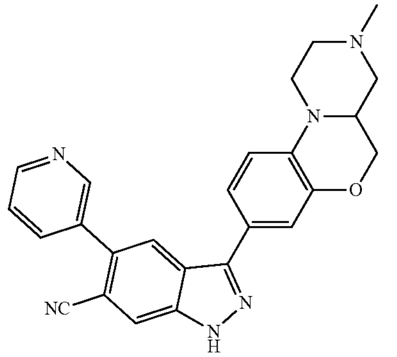 [SMILES: CN1CCN2c3ccc(-c4n[nH]c5cc(C#N)c(-c6cccnc6)cc45)cc3OCC2C1] | 423.2 |
| 42 | 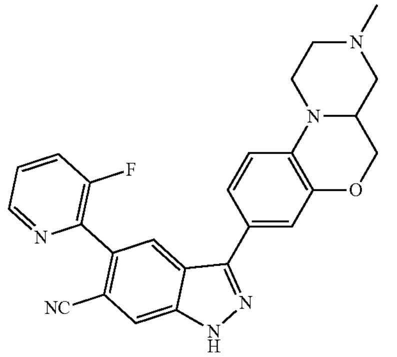 [SMILES: CN1CCN2c3ccc(-c4n[nH]c5cc(C#N)c(-c6ncccc6F)cc45)cc3OCC2C1] | 441.2 |
| 43 | 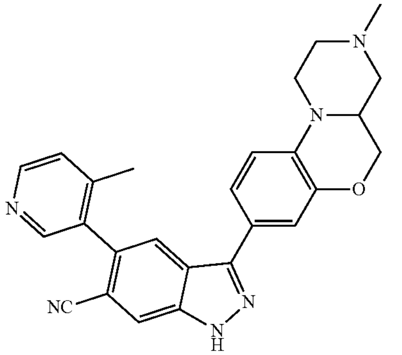 [SMILES: Cc1ccncc1-c1cc2c(-c3ccc4c(c3)OCC3CN(C)CCN43)n[nH]c2cc1C#N] | 437.2 |
| 44 | 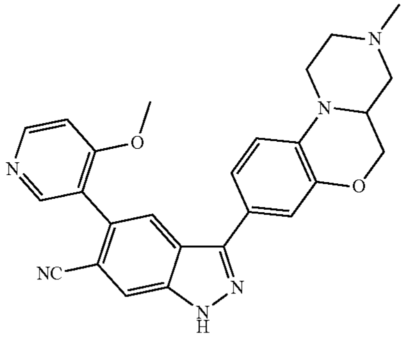 [SMILES: COc1ccncc1-c1cc2c(-c3ccc4c(c3)OCC3CN(C)CCN43)n[nH]c2cc1C#N] | 453.2 |

TABLE 1-continued
| Compound | Structure of compound | [M + H]$^+$ |
| --- | --- | --- |
| 45 | 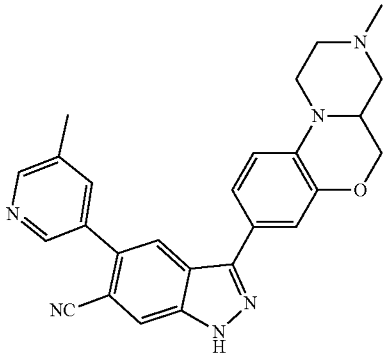 [SMILES: Cc1cncc(-c2cc3c(-c4ccc5c(c4)OCC4CN(C)CCN54)n[nH]c3cc2C#N)c1] | 437.2 |
| 46 | 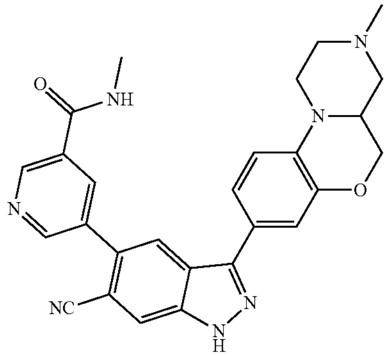 [SMILES: CNC(=O)c1cncc(-c2cc3c(-c4ccc5c(c4)OCC4CN(C)CCN54)n[nH]c3cc2C#N)c1] | 480.2 |
| 47 | 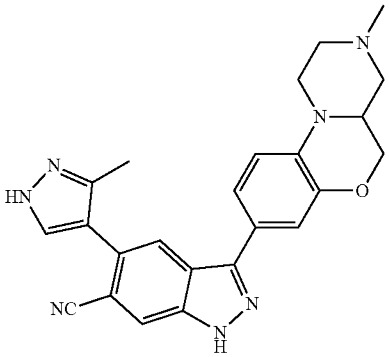 [SMILES: Cc1n[nH]cc1-c1cc2c(-c3ccc4c(c3)OCC3CN(C)CCN43)n[nH]c2cc1C#N] | 426.2 |
| 48 | 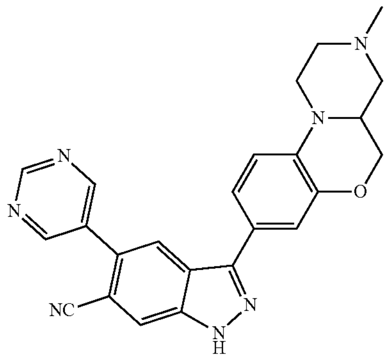 [SMILES: CN1CCN2c3ccc(-c4n[nH]c5cc(C#N)c(-c6cncnc6)cc45)cc3OCC2C1] | 424.2 |

TABLE 1-continued
| Compound | Structure of compound | [M + H]+ |
|---|---|---|
| 49 | 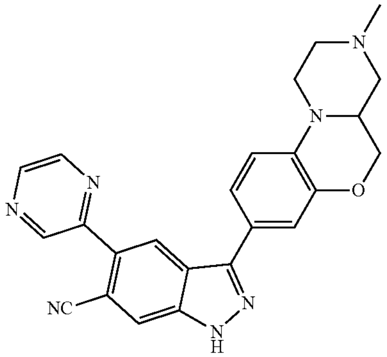 [SMILES: CN1CCN2c3ccc(-c4n[nH]c5cc(C#N)c(-c6cnccn6)cc45)cc3OCC2C1] | 424.2 |
| 50 | 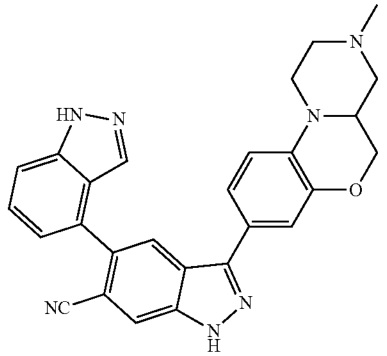 [SMILES: CN1CCN2c3ccc(-c4n[nH]c5cc(C#N)c(-c6cccc7[nH]ncc67)cc45)cc3OCC2C1] | 462.2 |
| 51 | 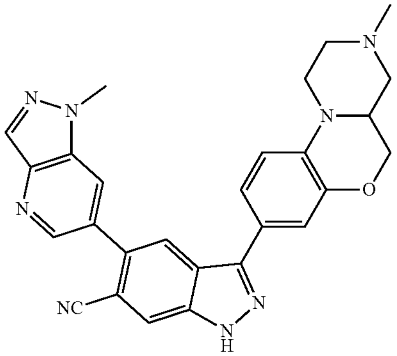 [SMILES: CN1CCN2c3ccc(-c4n[nH]c5cc(C#N)c(-c6cnc7cnn(C)c7c6)cc45)cc3OCC2C1] | 477.2 |
| 52 | 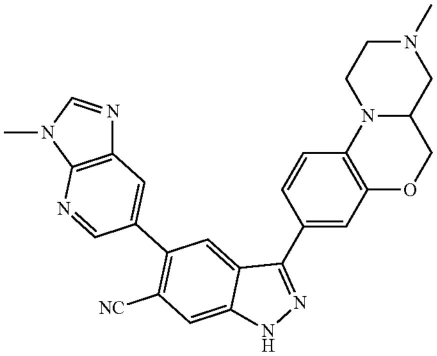 [SMILES: CN1CCN2c3ccc(-c4n[nH]c5cc(C#N)c(-c6cnc7c(c6)ncn7C)cc45)cc3OCC2C1] | 477.2 |

TABLE 1-continued
| Compound | Structure of compound | [M + H]$^+$ |
|---|---|---|
| 53 | 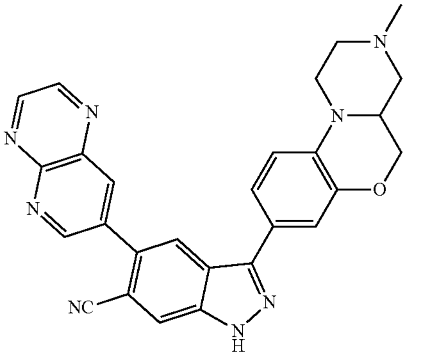 [SMILES: CN1CCN2c3ccc(-c4n[nH]c5cc(C#N)c(-c6cnc7nccnc7c6)cc45)cc3OCC2C1] | 475.2 |
| 54 | 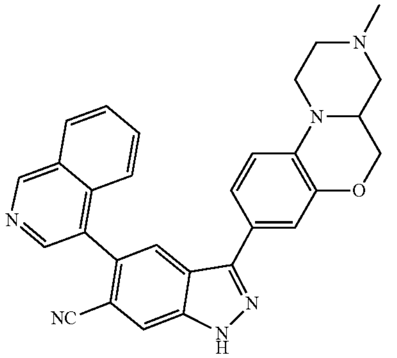 [SMILES: CN1CCN2c3ccc(-c4n[nH]c5cc(C#N)c(-c6cncc7ccccc67)cc45)cc3OCC2C1] | 473.2 |
| 55 | 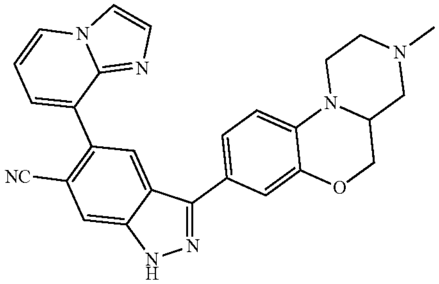 [SMILES: CN1CCN2c3ccc(-c4n[nH]c5cc(C#N)c(-c6cccn7cnnc67)cc45)cc3OCC2C1] | 462.2 |
| 56 | 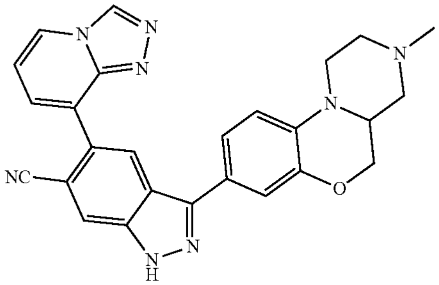 | 463.2 |
| 57 | 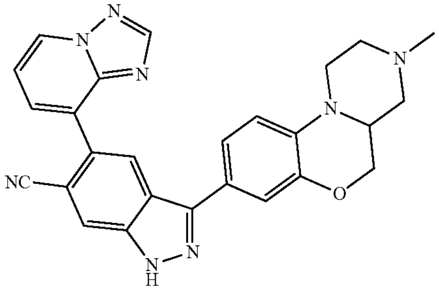 [SMILES: CN1CCN2c3ccc(-c4n[nH]c5cc(C#N)c(-c6cccn7ncnc67)cc45)cc3OCC2C1] | 463.2 |

TABLE 1-continued
| Compound | Structure of compound | [M + H]$^+$ |
| --- | --- | --- |
| 58 | 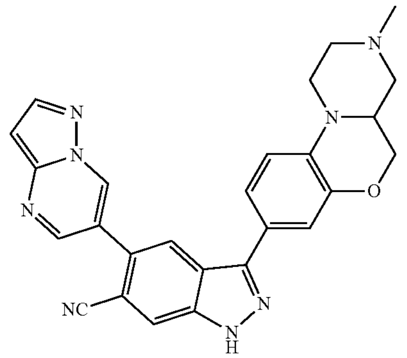 [SMILES: CN1CCN2c3ccc(-c4n[nH]c5cc(C#N)c(-c6cnc7ccnn7c6)cc45)cc3OCC2C1] | 463.2 |
| 59 | 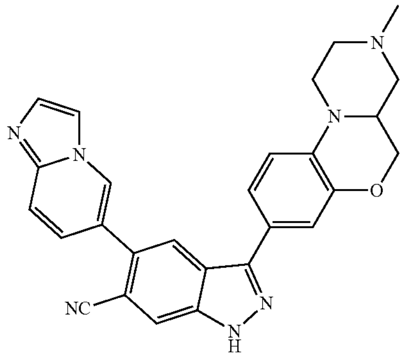 [SMILES: CN1CCN2c3ccc(-c4n[nH]c5cc(C#N)c(-c6ccc7nccn7c6)cc45)cc3OCC2C1] | 462.2 |
| 60 | 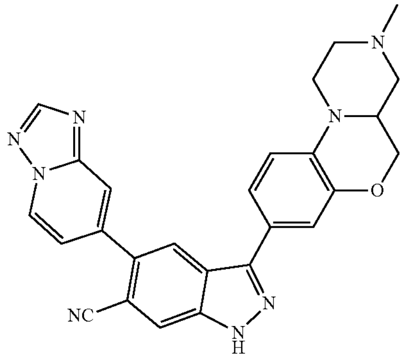 [SMILES: CN1CCN2c3ccc(-c4n[nH]c5cc(C#N)c(-c6ccn7ncnc7c6)cc45)cc3OCC2C1] | 463.2 |
| 61 | 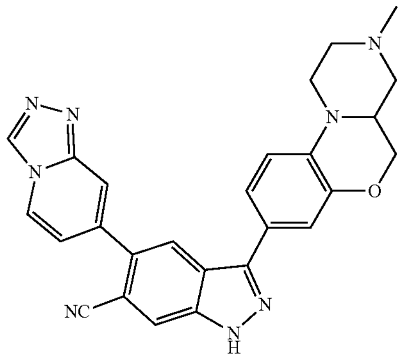 [SMILES: CN1CCN2c3ccc(-c4n[nH]c5cc(C#N)c(-c6ccn7cnnc7c6)cc45)cc3OCC2C1] | 463.2 |

TABLE 1-continued
| Compound | Structure of compound | [M + H]+ |
| --- | --- | --- |
| 62 | 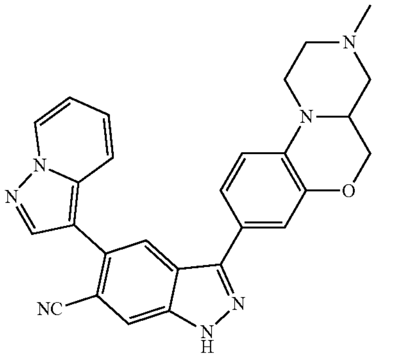 [SMILES: CN1CCN2c3ccc(-c4n[nH]c5cc(C#N)c(-c6cnn7ccccc67)cc45)cc3OCC2C1] | 462.2 |
| 63 | 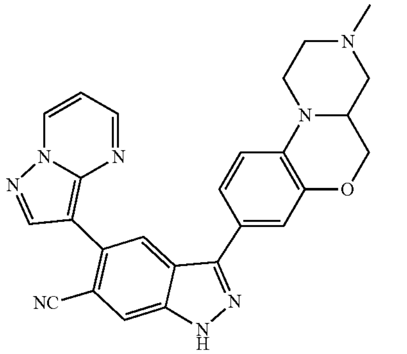 [SMILES: CN1CCN2c3ccc(-c4n[nH]c5cc(C#N)c(-c6cnn7cccnc67)cc45)cc3OCC2C1] | 463.2 |
| 64 | 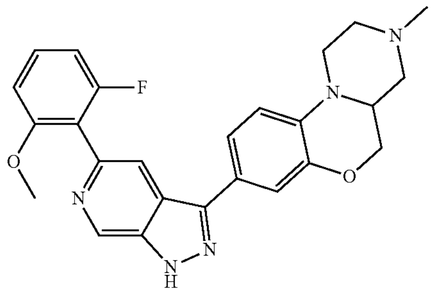 [SMILES: COc1cccc(F)c1-c1cc2c(-c3ccc4c(c3)OCC3CN(C)CCN43)n[nH]c2cn1] | 446.2 |
| 65 | 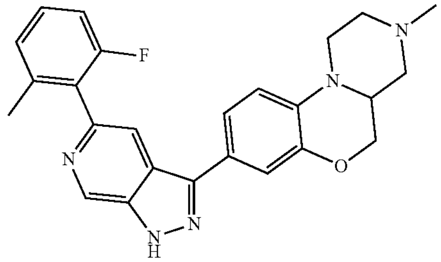 | 430.2 |
| 66 | 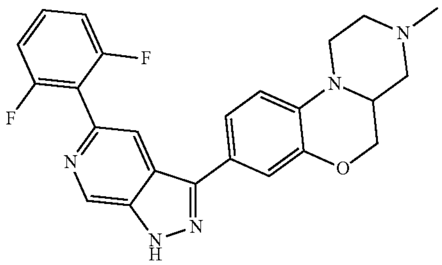 [SMILES: CN1CCN2c3ccc(-c4n[nH]c5cnc(-c6c(F)cccc6F)cc45)cc3OCC2C1] | 434.2 |

TABLE 1-continued
| Compound | Structure of compound | [M + H]+ |
|---|---|---|
| 67 | 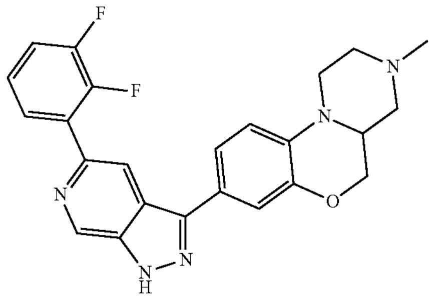 [SMILES: CN1CCN2c3ccc(-c4n[nH]c5cnc(-c6cccc(F)c6F)cc45)cc3OCC2C1] | 434.2 |
| 68 | 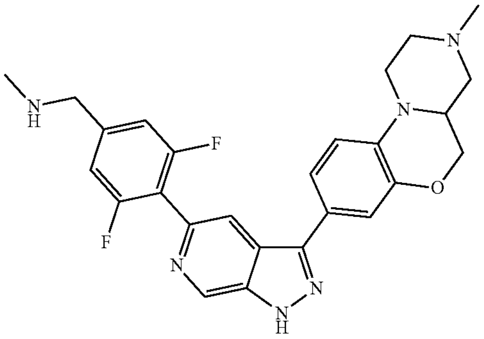 | 477.4 |
| 69 | 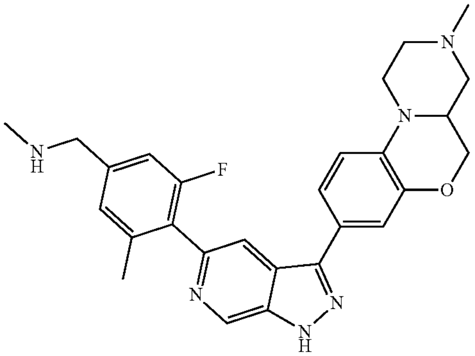 | 473.3 |
| 70 | 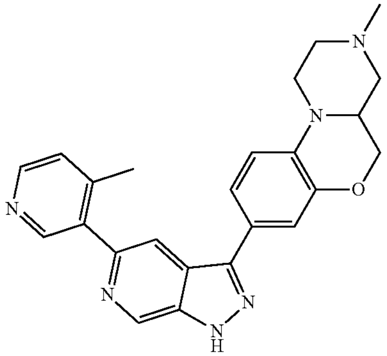 [SMILES: Cc1ccncc1-c1cc2c(-c3ccc4c(c3)OCC3CN(C)CCN43)n[nH]c2cn1] | 413.2 |

TABLE 1-continued
| Compound | Structure of compound | [M + H]+ |
|---|---|---|
| 71 | 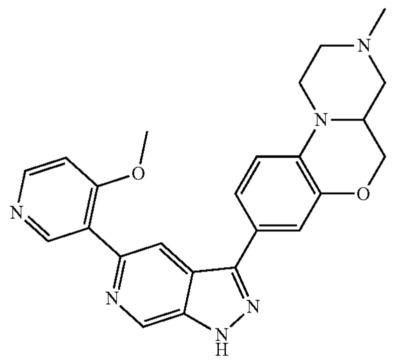 [SMILES: COc1ccncc1-c1cc2c(-c3ccc4c(c3)OCC3CN(C)CCN43)n[nH]c2cn1] | 429.2 |
| 72 | 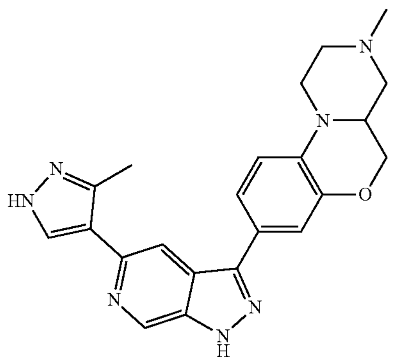 [SMILES: Cc1n[nH]cc1-c1cc2c(-c3ccc4c(c3)OCC3CN(C)CCN43)n[nH]c2cn1] | 402.2 |
| 73 | 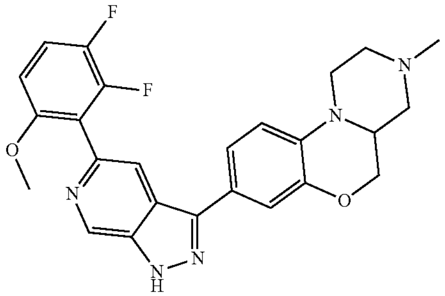 [SMILES: COc1ccc(F)c(F)c1-c1cc2c(-c3ccc4c(c3)OCC3CN(C)CCN43)n[nH]c2cn1] | 464.2 |
| 74 | 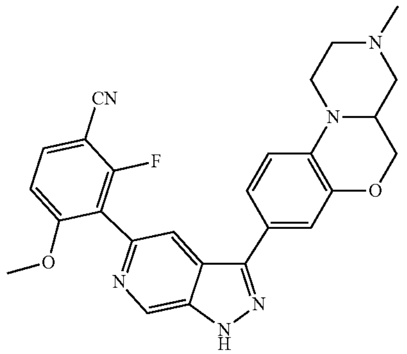 | 470.2 |

TABLE 1-continued
| Compound | Structure of compound | [M + H]+ |
| --- | --- | --- |
| 75 | 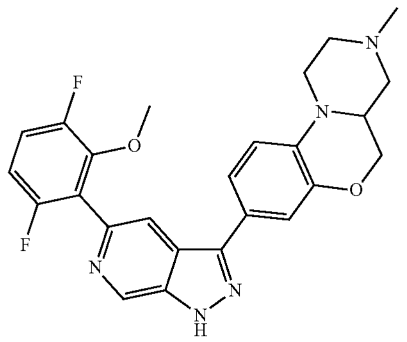 [SMILES: COc1c(F)ccc(F)c1-c1cc2c(-c3ccc4c(c3)OCC3CN(C)CCN43)n[nH]c2cn1] | 464.2 |
| 76 | 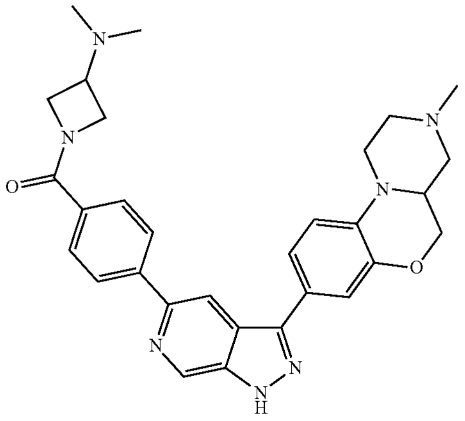 [SMILES: CN1CCN2c3ccc(-c4n[nH]c5cnc(-c6ccc(C(=O)N7CC(N(C)C)C7)cc6)cc45)cc3OCC2C1] | 524.3 |
| 77 | 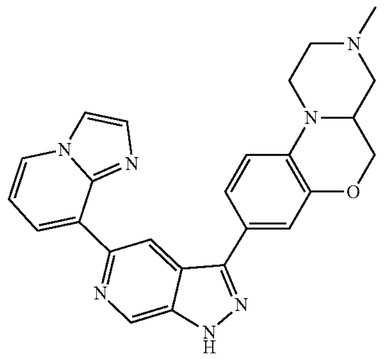 [SMILES: CN1CCN2c3ccc(-c4n[nH]c5cnc(-c6cccn7ccnc67)cc45)cc3OCC2C1] | 438.2 |
| 78 | 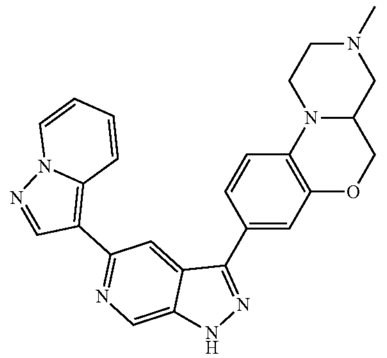 [SMILES: CN1CCN2c3ccc(-c4n[nH]c5cnc(-c6cnn7ccccc67)cc45)cc3OCC2C1] | 438.2 |

TABLE 1-continued
| Compound | Structure of compound | [M + H]+ |
| --- | --- | --- |
| 79 | 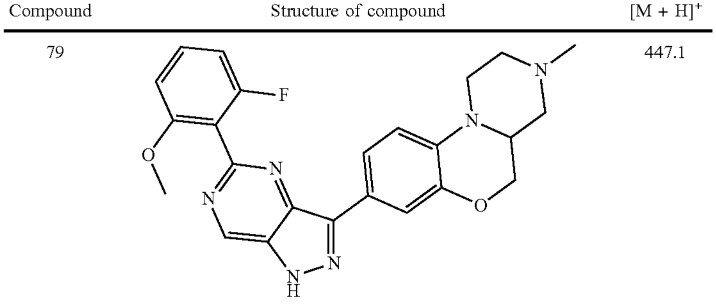 | 447.1 |
| 80 | 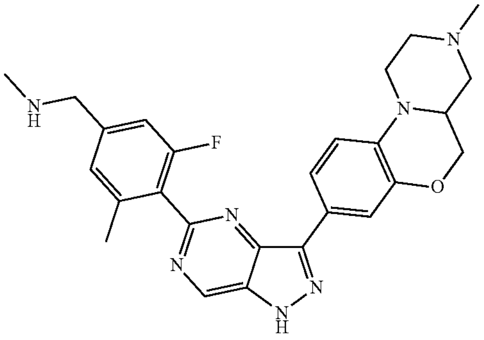 | 474.2 |
| 81 | 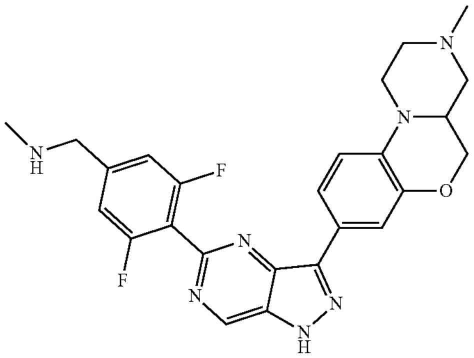 | 478.2 |
| 82 | 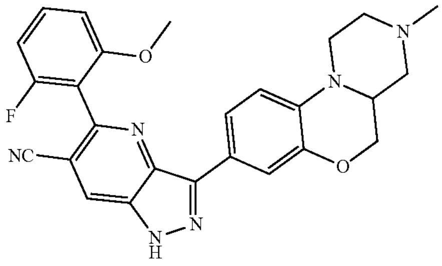 | 471.2 |
| 83 | 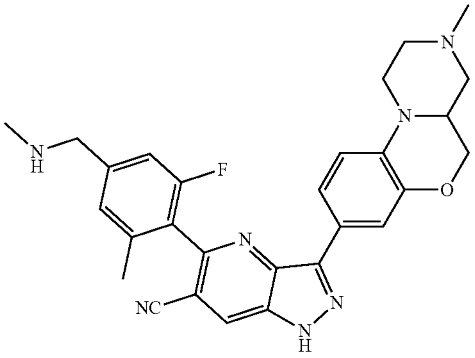 | 498.2 |

TABLE 1-continued
| Compound | Structure of compound | [M + H]+ |
| --- | --- | --- |
| 84 | 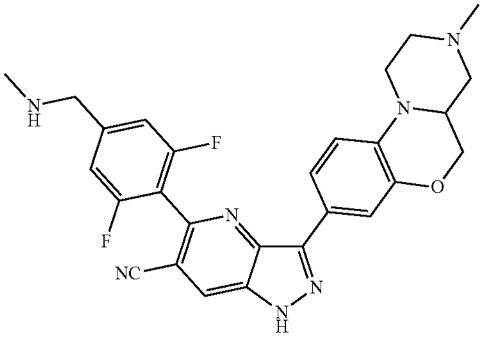 | 502.2 |
| 85 | 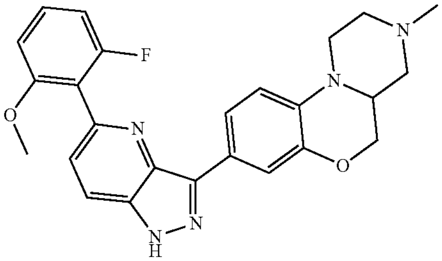 [SMILES: COc1cccc(F)c1-c1ccc2[nH]nc(-c3ccc4c(c3)OCC3CN(C)CCN43)c2n1] | 446.2 |
| 86 | 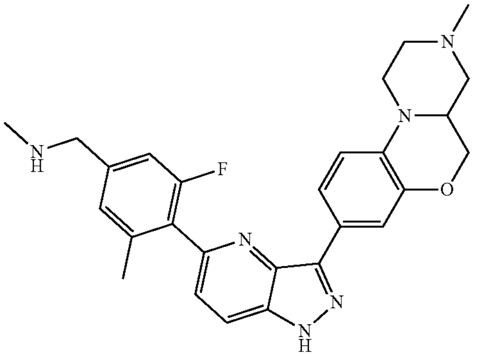 [SMILES: CNCc1cc(C)c(-c2ccc3[nH]nc(-c4ccc5c(c4)OCC4CN(C)CCN54)c3n2)c(F)c1] | 473.2 |
| 87 | 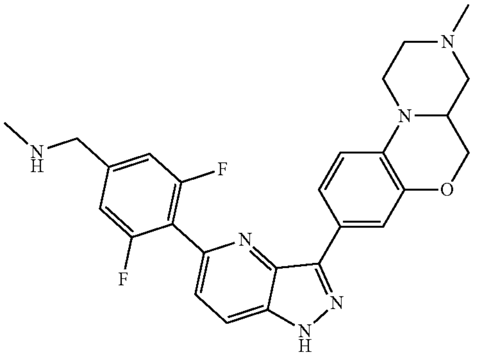 | 477.2 |

TABLE 1-continued
| Compound | Structure of compound | [M + H]$^+$ |
|---|---|---|
| 88 | 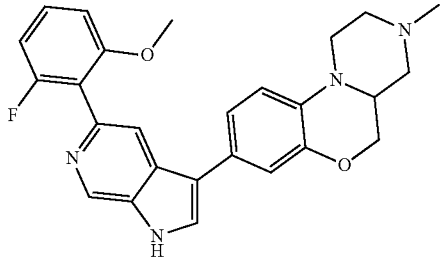 [SMILES: COc1cccc(F)c1-c1cc2c(-c3ccc4c(c3)OCC3CN(C)CCN43)c[nH]c2cn1] | 445.2 |
| 89 | 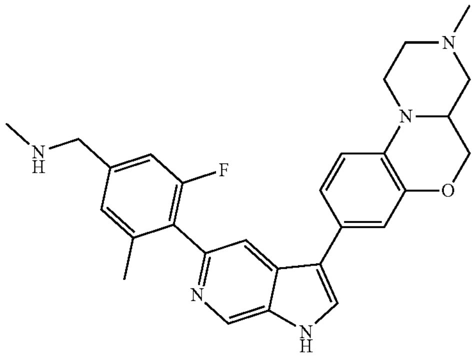 | 472.2 |
| 90 | 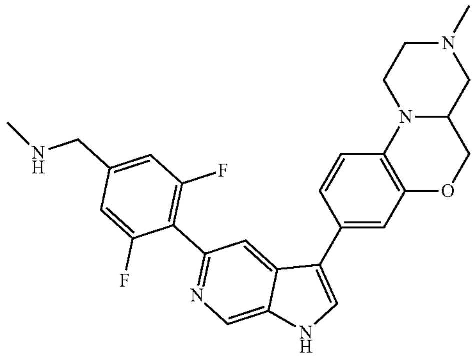 [SMILES: CNCc1cc(F)c(-c2cc3c(-c4ccc5c(c4)OCC4CN(C)CCN54)c[nH]c3cn2)c(F)c1] | 476.2 |
| 91 | 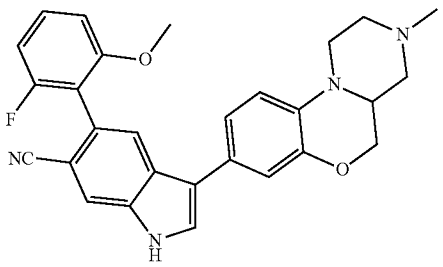 [SMILES: COc1cccc(F)c1-c1cc2c(-c3ccc4c(c3)OCC3CN(C)CCN43)c[nH]c2cc1C#N] | 469.2 |

TABLE 1-continued
| Compound | Structure of compound | [M + H]$^+$ |
| --- | --- | --- |
| 92 | 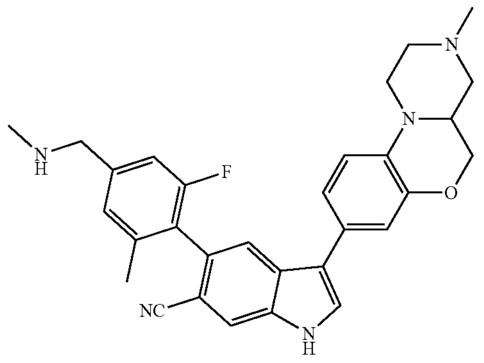 | 496.3 |
| 93 | 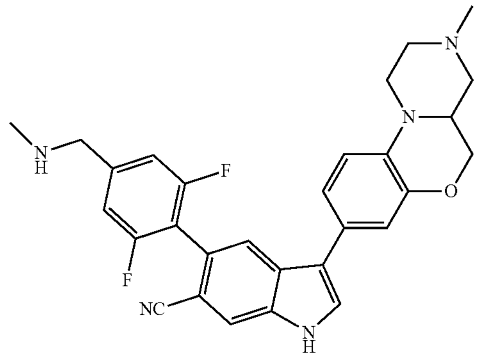 | 500.2 |
| 94 | 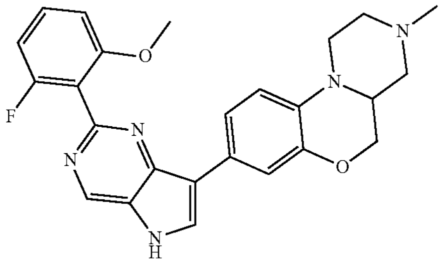 [SMILES: COc1cccc(F)c1-c1ncc2[nH]cc(-c3ccc4c(c3)OCC3CN(C)CCN43)c2n1] | 446.2 |
| 95 | 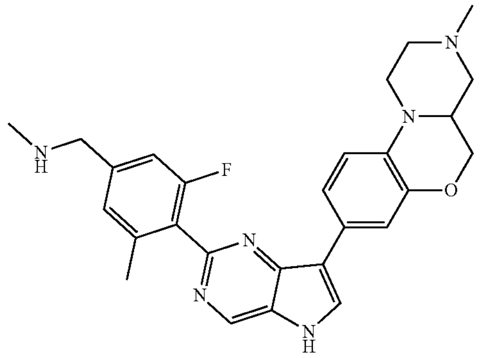 | 473.2 |

TABLE 1-continued
| Compound | Structure of compound | [M + H]+ |
| --- | --- | --- |
| 96 | 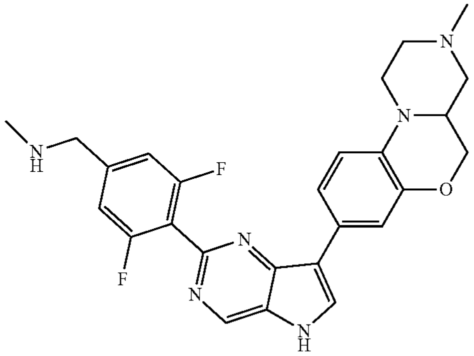 | 477.2 |
| 97 | 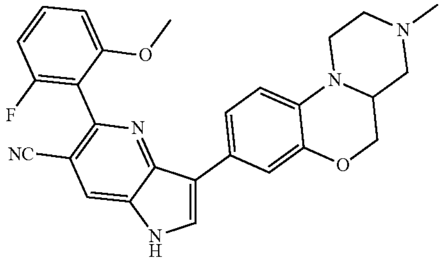 [SMILES: COc1cccc(F)c1-c1nc2c(-c3ccc4c(c3)OCC3CN(C)CCN43)c[nH]c2cc1C#N] | 470.2 |
| 98 | 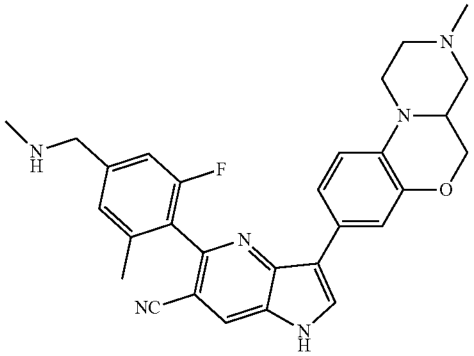 | 497.3 |
| 99 | 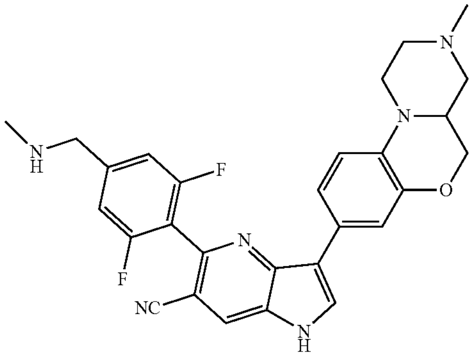 [SMILES: CNCc1cc(C)c(-c2nc3c(-c4ccc5c(c4)OCC4CN(C)CCN54)c[nH]c3cc2C#N)c(F)c1] | 501.2 |
| 100 | 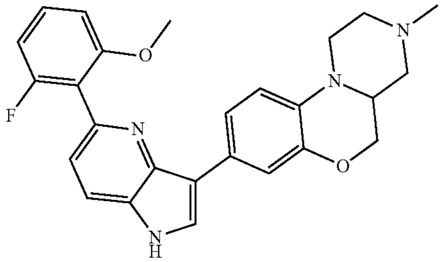 [SMILES: COc1cccc(F)c1-c1ccc2[nH]cc(-c3ccc4c(c3)OCC3CN(C)CCN43)c2n1] | 445.2 |

TABLE 1-continued
| Compound | Structure of compound | [M + H]+ |
| --- | --- | --- |
| 101 | 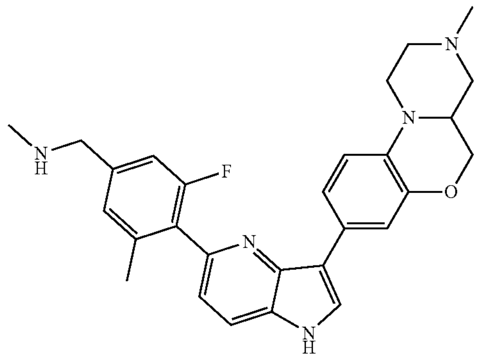 | 472.3 |
| 102 | 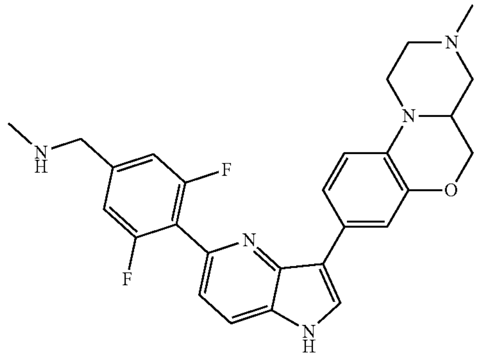 | 476.2 |
| 103 | 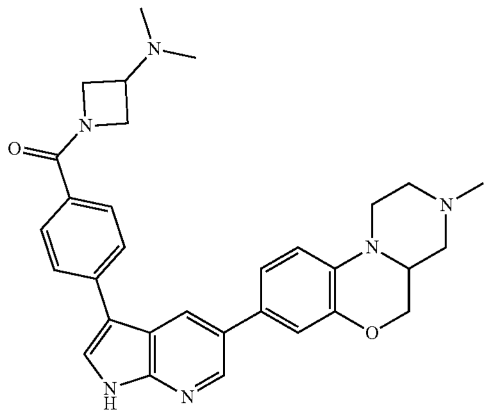 [SMILES: CN1CCN2c3ccc(-c4cnc5[nH]cc(-c6ccc(C(=O)N7CC(N(C)C)C7)cc6)c5c4)cc3OCC2C1] | 523.3 |
| 104 | 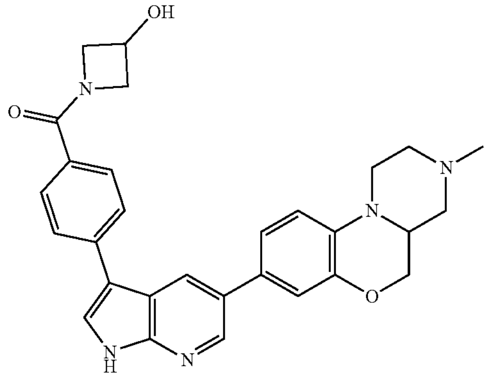 [SMILES: CN1CCN2c3ccc(-c4cnc5[nH]cc(-c6ccc(C(=O)N7CC(O)C7)cc6)c5c4)cc3OCC2C1] | 496.3 |

TABLE 1-continued
| Compound | Structure of compound | [M + H]+ |
|---|---|---|
| 105 | 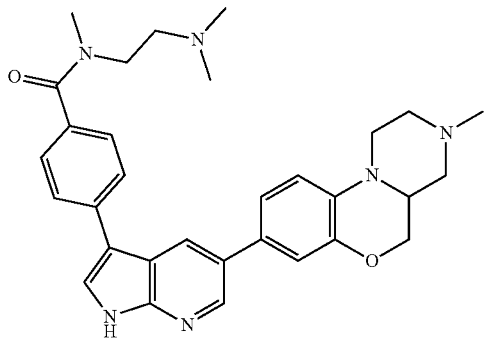 [SMILES: CN(C)CCN(C)C(=O)c1ccc(-c2c[nH]c3ncc(-c4ccc5c(c4)OCC4CN(C)CCN54)cc23)cc1] | 525.3 |
| 106 | 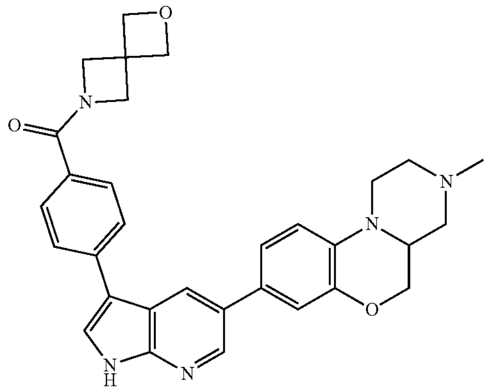 [SMILES: CN1CCN2c3ccc(-c4cnc5[nH]cc(-c6ccc(C(=O)N7CC8(COC8)C7)cc6)c5c4)cc3OCC2C1] | 522.3 |
| 107 | 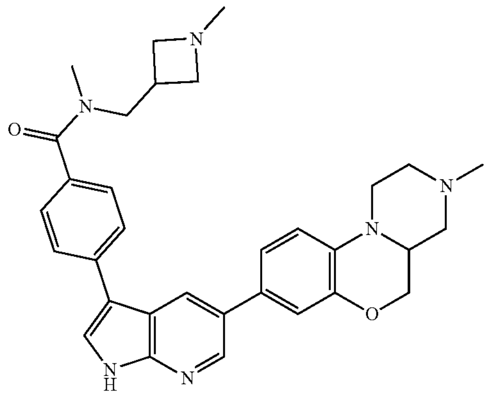 [SMILES: CN1CC(CN(C)C(=O)c2ccc(-c3c[nH]c4ncc(-c5ccc6c(c5)OCC5CN(C)CCN65)cc34)cc2)C1] | 537.3 |
| 108 | 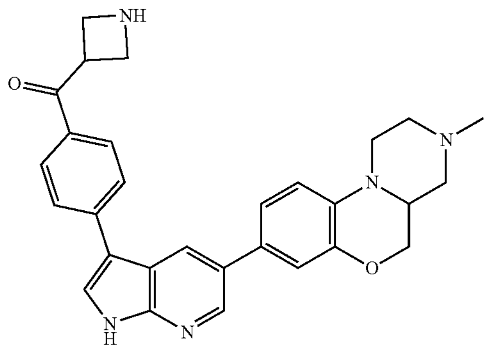 [SMILES: CN1CCN2c3ccc(-c4cnc5[nH]cc(-c6ccc(C(=O)C7CNC7)cc6)c5c4)cc3OCC2C1] | 480.3 |

TABLE 1-continued
| Compound | Structure of compound | [M + H]$^+$ |
|---|---|---|
| 109 | 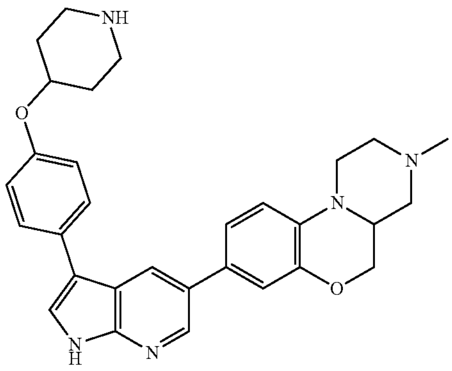 [SMILES: CN1CCN2c3ccc(-c4cnc5[nH]cc(-c6ccc(OC7CCNCC7)cc6)c5c4)cc3OCC2C1] | 496.3 |
| 110 | 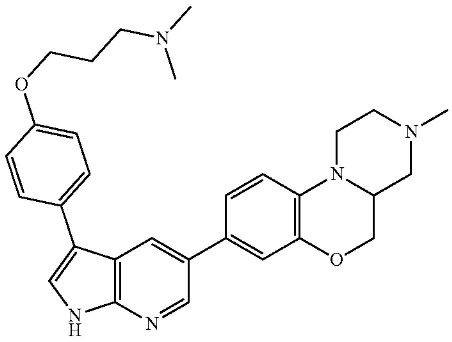 [SMILES: CN(C)CCCOc1ccc(-c2c[nH]c3ncc(-c4ccc5c(c4)OCC4CN(C)CCN54)cc23)cc1] | 498.3 |
| 111 | 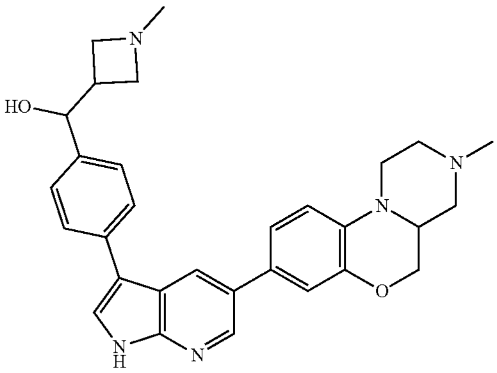 [SMILES: CN1CC(C(O)c2ccc(-c3c[nH]c4ncc(-c5ccc6c(c5)OCC5CN(C)CCN65)cc34)cc2)C1] | 496.3 |
| 112 | 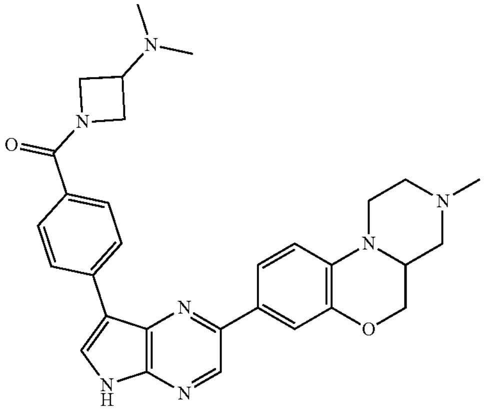 [SMILES: CN1CCN2c3ccc(-c4cnc5[nH]cc(-c6ccc(C(=O)N7CC(N(C)C)C7)cc6)c5n4)cc3OCC2C1] | 524.3 |

TABLE 1-continued
| Compound | Structure of compound | [M + H]+ |
| --- | --- | --- |
| 113 | 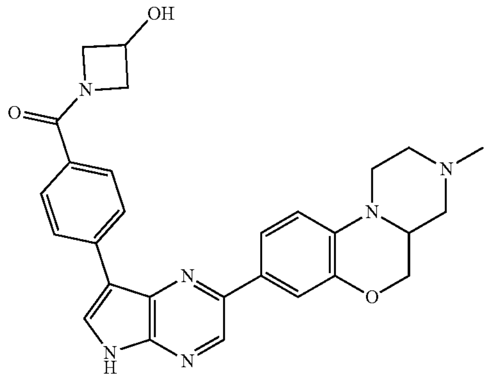 [SMILES: CN1CCN2c3ccc(-c4cnc5[nH]cc(-c6ccc(C(=O)N7CC(O)C7)cc6)c5n4)cc3OCC2C1] | 497.2 |
| 114 | 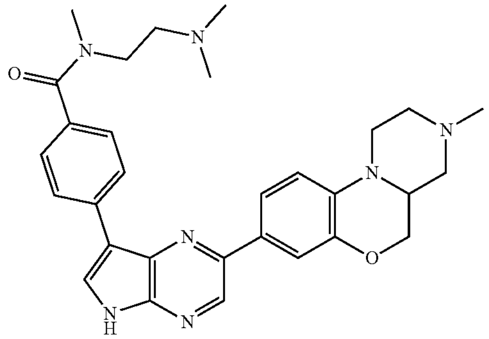 [SMILES: CN(C)CCN(C)C(=O)c1ccc(-c2c[nH]c3ncc(-c4ccc5c(c4)OCC4CN(C)CCN54)nc23)cc1] | 526.3 |
| 115 | 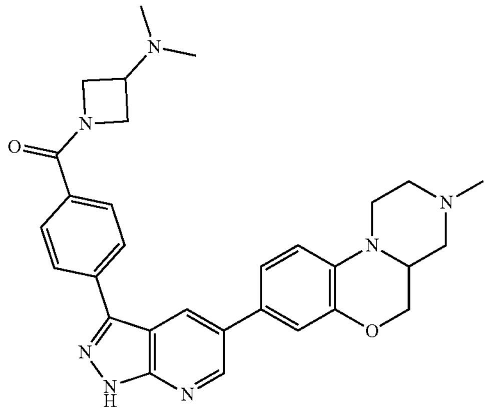 [SMILES: CN1CCN2c3ccc(-c4cnc5[nH]nc(-c6ccc(C(=O)N7CC(N(C)C)C7)cc6)c5c4)cc3OCC2C1] | 524.3 |
| 116 | 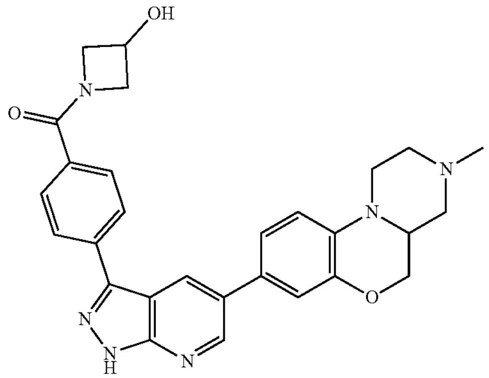 [SMILES: CN1CCN2c3ccc(-c4cnc5[nH]nc(-c6ccc(C(=O)N7CC(O)C7)cc6)c5c4)cc3OCC2C1] | 497.2 |

TABLE 1-continued
| Compound | Structure of compound | [M + H]$^+$ |
| --- | --- | --- |
| 117 | 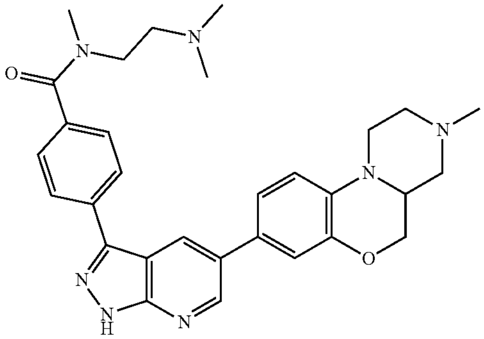 [SMILES: CN(C)CCN(C)C(=O)c1ccc(-c2n[nH]c3ncc(-c4ccc5c(c4)OCC4CN(C)CCN54)cc23)cc1] | 526.3 |
| 118 | 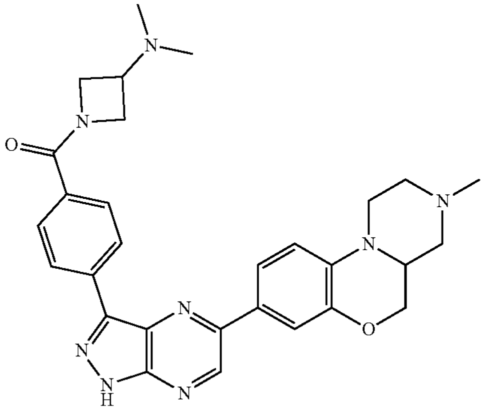 [SMILES: CN1CCN2c3ccc(-c4cnc5[nH]nc(-c6ccc(C(=O)N7CC(N(C)C)C7)cc6)c5n4)cc3OCC2C1] | 525.3 |
| 119 | 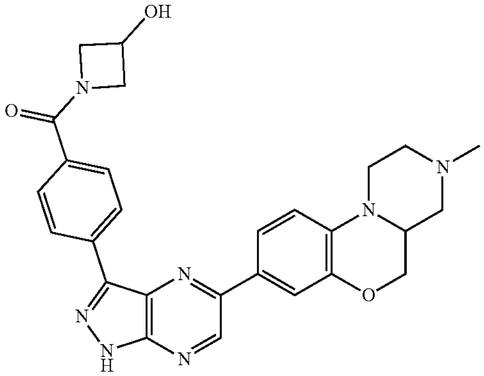 [SMILES: CN1CCN2c3ccc(-c4cnc5[nH]nc(-c6ccc(C(=O)N7CC(O)C7)cc6)c5n4)cc3OCC2C1] | 498.2 |
| 120 | 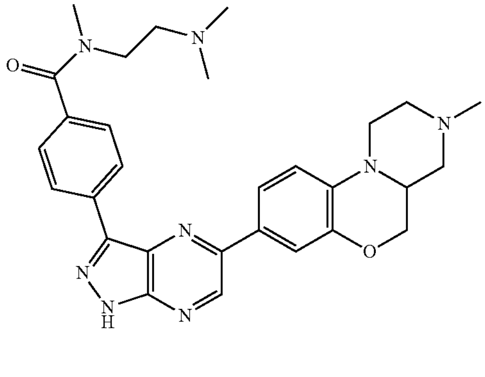 [SMILES: CN(C)CCN(C)C(=O)c1ccc(-c2n[nH]c3ncc(-c4ccc5c(c4)OCC4CN(C)CCN54)nc23)cc1] | 527.3 |

TABLE 1-continued
| Compound | Structure of compound | [M + H]$^+$ |
|---|---|---|
| 121 | 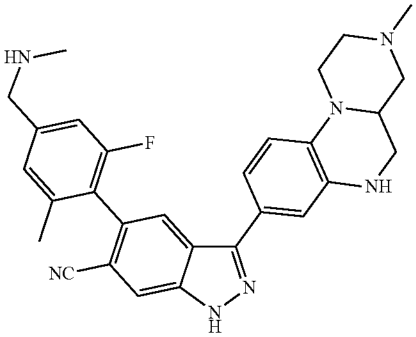 [SMILES: CNCc1cc(C)c(-c2cc3c(-c4ccc5c(c4)NCC4CN(C)CCN54)n[nH]c3cc2C#N)c(F)c1] | 496.3 |
| 122 | 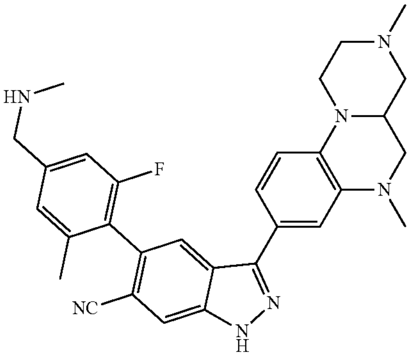 [SMILES: CNCc1cc(C)c(-c2cc3c(-c4ccc5c(c4)N(C)CC4CN(C)CCN54)n[nH]c3cc2C#N)c(F)c1] | 510.3 |
| 123 | 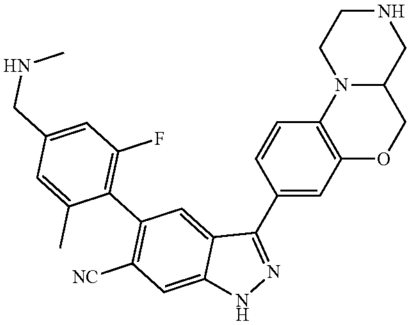 [SMILES: CNCc1cc(C)c(-c2cc3c(-c4ccc5c(c4)OCC4CNCCN54)n[nH]c3cc2C#N)c(F)c1] | 483.2 |
| 124 | 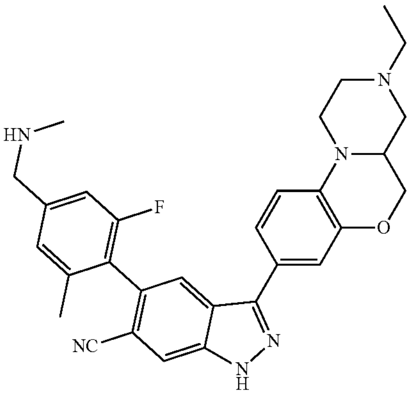 [SMILES: CCN1CCN2c3ccc(-c4n[nH]c5cc(C#N)c(-c6c(C)cc(CNC)cc6F)cc45)cc3OCC2C1] | 511.3 |

TABLE 1-continued
| Compound | Structure of compound | [M + H]+ |
| --- | --- | --- |
| 125 | 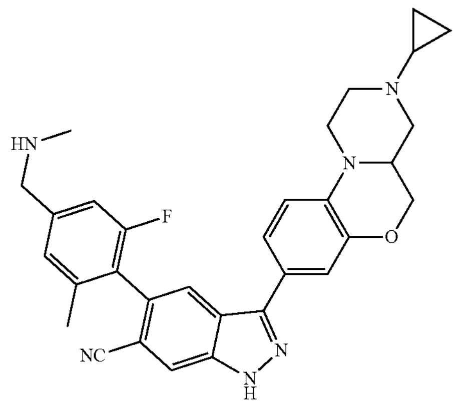 [SMILES: CNCc1cc(C)c(-c2cc3c(-c4ccc5c(c4)OCC4CN(C6CC6)CCN54)n[nH]c3cc2C#N)c(F)c1] | 523.3 |
| 126 | 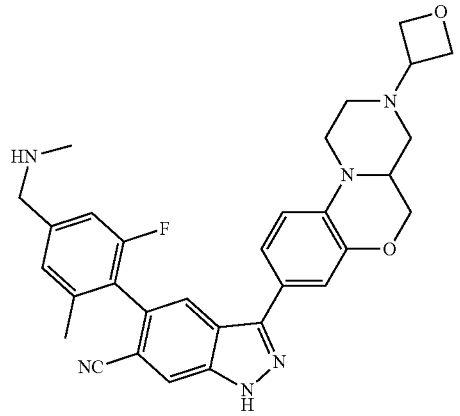 [SMILES: CNCc1cc(C)c(-c2cc3c(-c4ccc5c(c4)OCC4CN(C6COC6)CCN54)n[nH]c3cc2C#N)c(F)c1] | 539.3 |
| 127 | 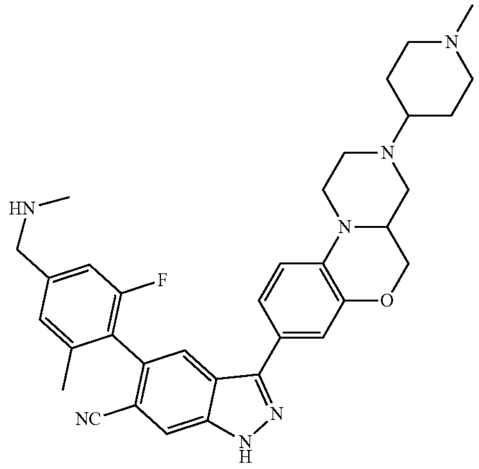 [SMILES: CNCc1cc(C)c(-c2cc3c(-c4ccc5c(c4)OCC4CN(C6CCN(C)CC6)CCN54)n[nH]c3cc2C#N)c(F)c1] | 580.3 |

TABLE 1-continued

| Compound | Structure of compound | [M + H]$^+$ |
|---|---|---|
| 128 | 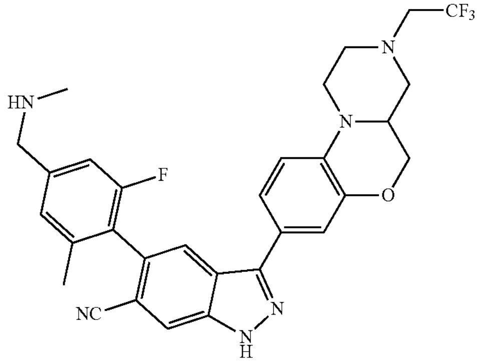 [SMILES: CNCc1cc(C)c(-c2cc3c(-c4ccc5c(c4)OCC4CN(CC(F)(F)F)CCN54)n[nH]c3cc2C#N)c(F)c1] | 565.3 |
| 129 | 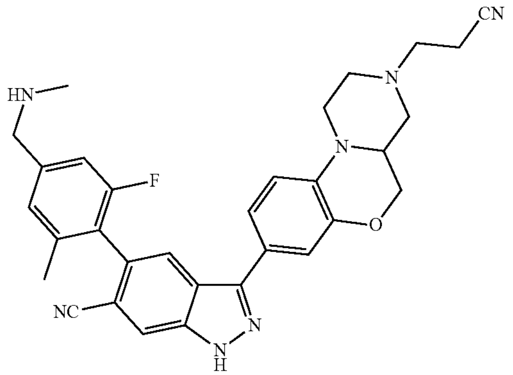 [SMILES: CNCc1cc(C)c(-c2cc3c(-c4ccc5c(c4)OCC4CN(CCC#N)CCN54)n[nH]c3cc2C#N)c(F)c1] | 536.3 |

Example 130: Assay of Inhibitory Effect of Compound Against Enzyme Activity of HPK1

The inhibitory effect of the compound against the enzyme activity of HPK1 was determined by using a lantha Screen method with PKC as a substrate. The process comprises the following specific steps: the HPK1 protein was incubated with the serially-diluted compound at 28° C. for 10 min followed by addition of fluoroescein-labeled PKC substrate and ATP to react for 90 min. After termination of the reaction, a Terbium-labeled antibody against phosphorylated PKC was added and incubated for 60 min. The energy transfer of Teribium and fluoroscein was monitored by detecting luminescence at 520 nm and 450 nm to quantify PKC as the level of phosphorylation of HPK1. Inhibition % and $IC_{50}$ of the compound were calculated compared to the control group.

TABLE 2

| Inhibitory effect of the compound disclosed herein against enzyme activity of HPK1 | | | | | |
|---|---|---|---|---|---|
| Compound | Inhibition rate (%) | Compound | Inhibition rate (%) | Compound | Inhibition rate (%) |
| 1 | +++ | 2 | +++ | 3 | ++ |
| 4 | ++ | 5 | ++ | 6 | +++ |
| 7 | + | 8 | +++ | 9 | +++ |
| 10 | +++ | 11 | ++ | 12 | +++ |
| 13 | + | 14 | +++ | 15 | +++ |
| 16 | +++ | 17 | +++ | 18 | +++ |
| 19 | +++ | 20 | +++ | 21 | +++ |
| 22 | +++ | 23 | +++ | 24 | +++ |
| 25 | +++ | 26 | +++ | 27 | +++ |

TABLE 2-continued

| Inhibitory effect of the compound disclosed herein against enzyme activity of HPK1 | | | | | |
|---|---|---|---|---|---|
| Compound | Inhibition rate (%) | Compound | Inhibition rate (%) | Compound | Inhibition rate (%) |
| 28 | +++ | 29 | +++ | 30 | +++ |
| 31 | ++ | 32 | +++ | 33 | +++ |
| 34 | ++ | 35 | +++ | 36 | +++ |
| 37 | +++ | 38 | +++ | 39 | +++ |
| 40 | ++ | 41 | +++ | 42 | +++ |
| 43 | +++ | 44 | +++ | 45 | +++ |
| 46 | +++ | 47 | +++ | 48 | +++ |
| 49 | +++ | 50 | +++ | 51 | +++ |
| 52 | +++ | 53 | +++ | 54 | ++ |
| 55 | +++ | 56 | +++ | 57 | +++ |
| 58 | +++ | 59 | +++ | 60 | +++ |
| 61 | +++ | 62 | ++ | 63 | +++ |
| 64 | +++ | 65 | ++ | 66 | ++ |
| 67 | ++ | 68 | +++ | 69 | +++ |
| 70 | +++ | 71 | +++ | 72 | +++ |
| 73 | ++ | 74 | ++ | 75 | ++ |
| 76 | ++ | 77 | +++ | 78 | +++ |
| 79 | ++ | 80 | ++ | 81 | ++ |
| 82 | ++ | 83 | +++ | 84 | +++ |
| 85 | ++ | 86 | ++ | 87 | ++ |
| 88 | +++ | 89 | +++ | 90 | +++ |
| 91 | +++ | 92 | +++ | 93 | +++ |
| 94 | ++ | 95 | +++ | 96 | ++ |
| 97 | ++ | 98 | +++ | 99 | +++ |
| 100 | +++ | 101 | +++ | 102 | +++ |
| 103 | +++ | 104 | ++ | 105 | +++ |
| 106 | +++ | 107 | +++ | 108 | ++ |
| 109 | +++ | 110 | +++ | 111 | +++ |
| 112 | +++ | 113 | +++ | 114 | +++ |
| 115 | +++ | 116 | ++ | 117 | +++ |
| 118 | +++ | 119 | ++ | 120 | +++ |

TABLE 2-continued

| Inhibitory effect of the compound disclosed herein against enzyme activity of HPK1 | | | | | |
|---|---|---|---|---|---|
| Compound | Inhibition rate (%) | Compound | Inhibition rate (%) | Compound | Inhibition rate (%) |
| 121 | +++ | 122 | +++ | 123 | +++ |
| 124 | +++ | 125 | +++ | 126 | +++ |
| 127 | +++ | 128 | +++ | 129 | +++ |
| 1-a | +++ | 1-b | +++ | | |

+ means that $IC_{50}$ is greater than or equal to 100 nM.
++ means that $IC_{50}$ is greater than 10 nM but less than 100 nM.
+++ means that $IC_{50}$ is less than or equal to 10 nM.

As can be seen from data in Table 2, the compound disclosed herein has an inhibitory effect against the enzyme activity of HPK1 with an $IC_{50}$ value less than or equal to 10 nM, and thus has a strong inhibitory effect against enzyme activity of HPK1.

Example 131: Assay of Inhibitory Effect of Compound Against hERG Channel Activity The HEK293 cell line stably expressed by the hERG potassium channel was adopted for detection using manual patch clamp. Firstly, the HEK293 cell line stably expressed by the hERG potassium channel was separated and laid on a cover glass before the patch clamp detection test, and the test detection was carried out after culture for 18 h. Then a capillary glass tube was drawn into a recording electrode, and the recording electrode was contacted onto the cells under an inverted microscope to form a whole-cell recording mode. After necessary compensation and recording of the membrane capacitance and series resistance, current recording was performed according to the set current stimulation protocol. After the hERG current stabilized, administration was started and the current detected in compound-free extracellular fluid for each cell served as its own control group, and multiple cells were repeatedly tested independently. The current acted for each drug concentration and the current of the blank control were standardized, then the inhibition rate corresponding to each drug concentration was calculated, and finally the half-inhibition concentration $IC_{50}$ value of each compound was calculated.

TABLE 3

| Inhibitory effect of the compound disclosed herein against hERG channel activity ($IC_{50}$) | |
|---|---|
| Compound | hERG channel inhibitory activity ($IC_{50}$, μM) |
| 6 | 17.8 |
| 16 | 23.6 |
| 18 | 11.8 |
| 35 | 31.8 |
| 43 | 17.4 |
| 67 | 51.2 |
| 73 | 41.2 |
| 112 | 35.6 |

As can be seen from data in Table 2, the compound disclosed herein has a weak inhibitory effect against hERG channel, with an inhibition activity $IC_{50}$ value greater than 10 μM, which indicates that the compound has better safety in the aspect of heart safety.

The invention claimed is:

1. A compound with a structure as shown as general formula (1), or isomers, crystalline forms, pharmaceutically acceptable salts, hydrates or solvates thereof:

(1)

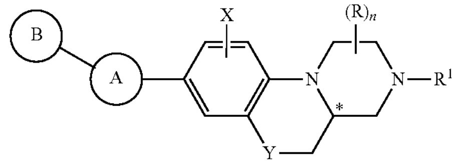

in formula (1):

"*" denotes a chiral center;

n is an integer of 0, 1, 2 or 3;

X is H, halogen, $C_{1-3}$ alkyl, $C_{1-3}$ haloalkyl or $C_{3-6}$ cycloalkyl;

Y is —O—, —NH— or —N($C_{1-3}$ alkyl)-;

when each R is linked to a different carbon atom, each R is independently H or $C_{1-3}$ alkyl; when two R are simultaneously linked to the same carbon atom, the two R may independently be H or $C_{1-3}$ alkyl or form a carbon group (C═O) with a carbon atom linked thereto;

$R^1$ is H, $C_{1-6}$ alkyl, $C_{3-6}$ cycloalkyl, heterocycloalkyl, hydroxy-substituted $C_{1-6}$ alkyl, halogen-substituted $C_{1-6}$ alkyl, $C_{1-6}$ alkoxy-substituted $C_{1-6}$ alkyl or cyano-substituted $C_{1-6}$ alkyl;

A is the following group:

and wherein "**" denotes a position linking to a group B;

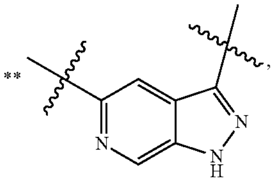

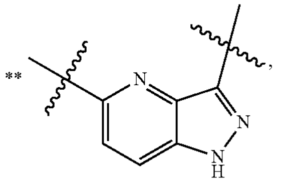

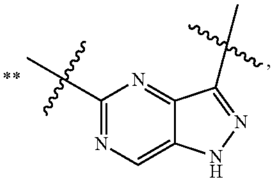

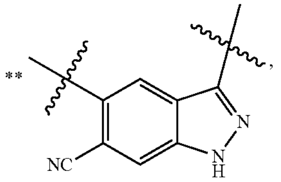

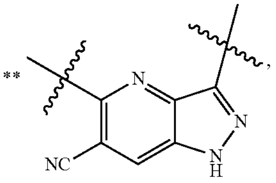

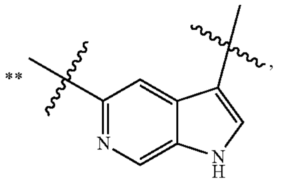

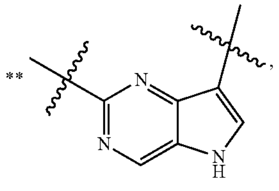

-continued

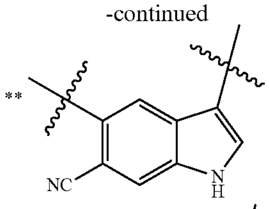

, or

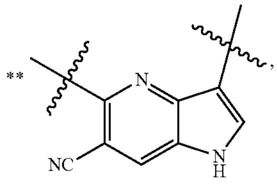

,

B is $C_{6-10}$ aryl or 5-10 membered heteroaryl, wherein the 5-10 membered heteroaryl consists of at least 1 carbon atom and 1-4 heteroatoms selected from the group consisting of N, O and S; wherein the N or S atom may be oxidized; wherein ring carbon atoms of the 5-10 membered heteroaryl may be optionally substituted with oxygen to form a carbonyl group (C═O); and the $C_{6-10}$ aryl and 5-10 membered heteroaryl are optionally substituted with 1-5 substituents independently selected from $R^2$;

$R^2$ is independently halogen, CN, $NO_2$, $C_{1-6}$ alkyl, $C_{2-6}$ alkenyl, $C_{2-6}$ alkynyl, $C_{1-6}$ haloalkyl, cyano-substituted $C_{1-6}$ alkyl, hydroxy-substituted $C_{1-6}$ alkyl, $C_{1-3}$ alkoxy-substituted $C_{1-6}$ alkyl, $C_{1-3}$ haloalkoxy-substituted $C_{1-6}$ alkyl, $C_{3-6}$ cycloalkyl, 4-7 membered heterocycloalkyl, 5-7 membered heteroaryl, $OR^3$, $SR^3$, $C(O)R^3$, $S(O)R^3$, $S(O)_2R^3$, $C(O)OR^3$, $OC(O)R^3$, $NR^4R^5$, $P(O)R^4R^5$, $C(O)NR^4R^5$, $OC(O)NR^4R^5$, —$C_{1-6}$ alkyl-$NR^4R^5$, —O—$C_{1-6}$ alkyl-$NR^4R^5$, —$C_{1-6}$ alkyl-$OR^3$, —O—$C_{1-6}$ alkyl-$R^3$, -hydroxy-substituted $C_{1-6}$ alkyl-$R^3$, —$NR^6C(O)R^3$, —$NR^6S(O)_2R^3$, —$NR^6CO$—$C_{1-3}$ alkyl-$R^3$ or —$NR^6CO$—$C_{1-3}$ alkyl-$NR^4R^5$;

or two adjacent $R^2$ substituents on ring B, together with atoms linked thereto, form a fused 4-7 membered heterocycloalkyl or $C_{3-7}$ cycloalkyl, wherein the fused 4-7 membered heterocycloalkyl contains at least 1 carbon atom and 1-4 heteroatoms selected from the group consisting of N, O and S; wherein the N or S atom may be oxidized; wherein ring carbon atoms of the fused 4-7 membered heterocycloalkyl may be optionally substituted with oxygen to form a carbonyl group (C═O); and the fused 4-7 membered heterocycloalkyl or the $C_{3-7}$ cycloalkyl is optionally substituted with 1-5 substituents independently selected from $R^7$;

each $R^3$ is independently H, $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, $C_{6-10}$ aryl, 5-7 membered heteroaryl, cyano-substituted $C_{1-6}$ alkyl, hydroxy-substituted $C_{1-6}$ alkyl, $C_{1-3}$ alkoxy-substituted $C_{1-6}$ alkyl or $C_{1-3}$ haloalkoxy-substituted $C_{1-6}$ alkyl;

each of $R^4$ and $R^5$ are independently H, $C_{1-6}$ alkyl, $C_{2-6}$ alkenyl, $C_{2-6}$ alkynyl, $C_{1-6}$ haloalkyl, $C_{3-6}$ cycloalkyl, cyano-substituted $C_{1-6}$ alkyl, hydroxy-substituted $C_{1-6}$ alkyl, $C_{1-3}$ alkoxy-substituted $C_{1-6}$ alkyl or $C_{1-3}$ haloalkoxy-substituted $C_{1-6}$ alkyl, $C_{6-10}$ aryl-substituted $C_{1-6}$ alkyl or 5-10 membered heteroaryl-substituted $C_{1-6}$ alkyl, or $R^4$ and $R^5$, together with an N atom, form 4-12 membered heterocycloalkyl, the 4-12 membered heterocycloalkyl optionally being substituted with 1-5 substituents independently selected from $R^7$;

each $R^6$ is H or $C_{1-3}$ alkyl;

each $R^7$ is OH, CN, $NH_2$, NHMe, $NMe_2$, $C_{1-6}$ alkyl, $C_{1-6}$ haloalkyl or $C_{1-6}$ alkoxy.

2. The compound, or the isomers, the crystalline forms, the pharmaceutically acceptable salts, the hydrates or the solvates thereof according to claim 1, wherein in general formula (1), X is H, F, Cl, Me, Et, $CF_3$, isopropyl or cyclopropyl.

3. The compound, or the isomers, the crystalline forms, the pharmaceutically acceptable salts, the hydrates or the solvates thereof according to claim 1, wherein in general formula (1), Y is —O—, —NH—, —N(Me)- or —N(Et)-.

4. The compound, or the isomers, the crystalline forms, the pharmaceutically acceptable salts, the hydrates or the solvates thereof according to claim 1, wherein in general formula (1), R is H or Me.

5. The compound, or the isomers, the crystalline forms, the pharmaceutically acceptable salts, the hydrates or the solvates thereof according to claim 1, wherein in general formula (1), $R^1$ is H, Me, Et

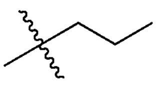 , 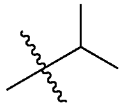 , 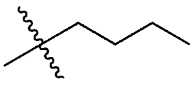 ,

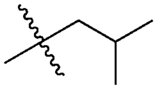 , 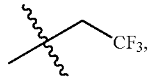 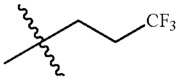 ,

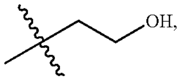 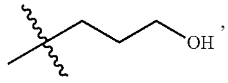 ,

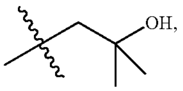 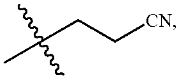

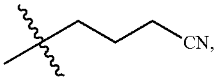 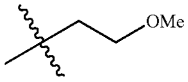 ,

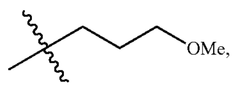 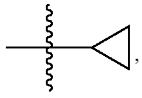 ,

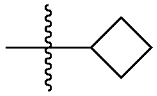 , 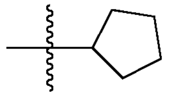 ,

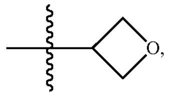 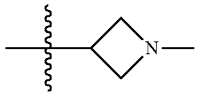 ,

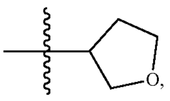 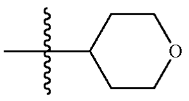 or

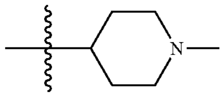 .

6. The compound, or the isomers, the crystalline forms, the pharmaceutically acceptable salts, the hydrates or the solvates thereof according to claim 1, wherein in general formula (1), B is

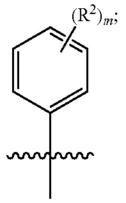
$R^2$ is independently H, $CH_3$, F, Cl, $OCH_3$, $CF_3$, CN, $CONH_2$,
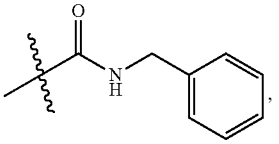
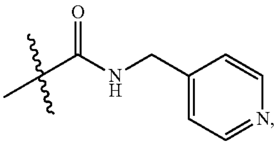
$NHSO_2CH_3$, $NHCOCH_3$, $PO(CH_3)_2$, $SO_2CH_3$, $SO_2NH_2$, $SO_2NHCH_3$, $CH_2NHCH_3$, $CH_2NHCH_2CH_3$,
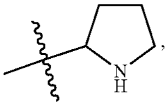
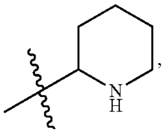
$CH(CH_3)NHCH_3$, $CH_2CN$, $CH_2OCH_3$,
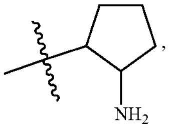
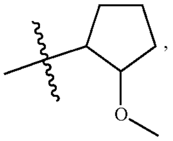
$NHCOCH_2N(CH_3)_2$,
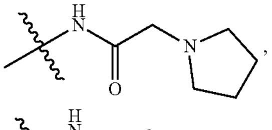
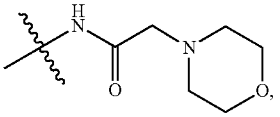
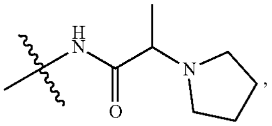
-continued
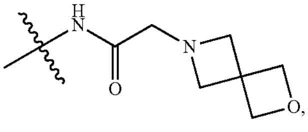
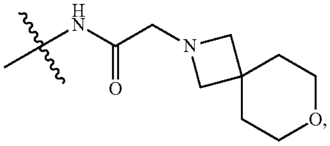
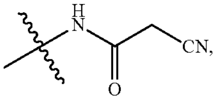
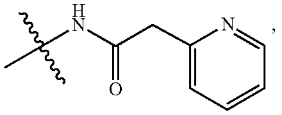
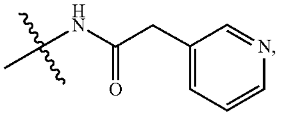
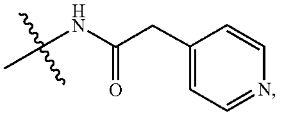
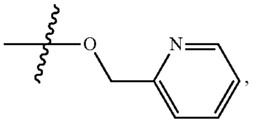
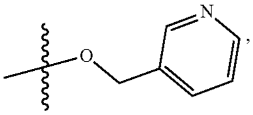
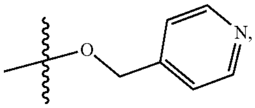
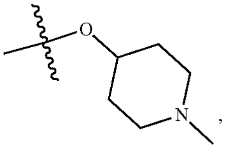
$OCON(CH_3)_2$,
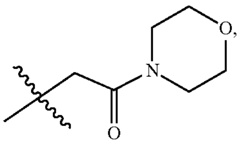
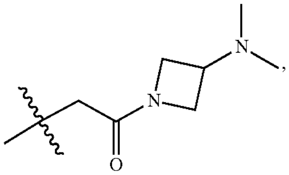

-continued
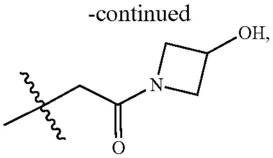
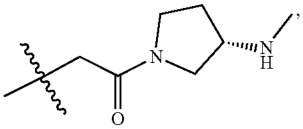
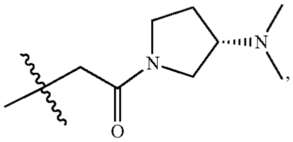
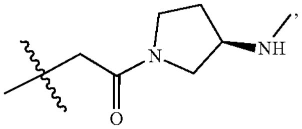
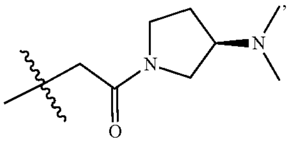
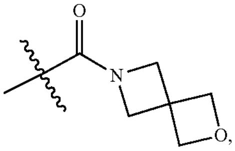
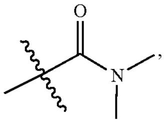
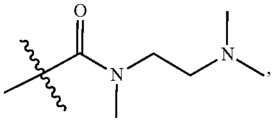
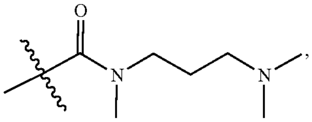
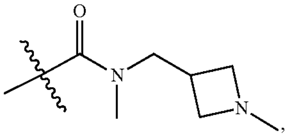
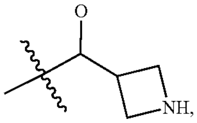
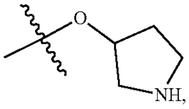
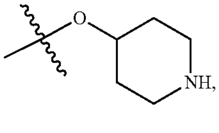
$OCH_2CH_2CH_2NH_2$, $OCH_2CH_2CH_2N(CH_3)_2$,
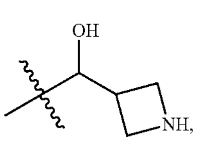 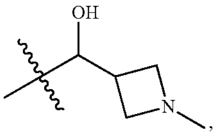
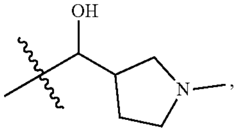 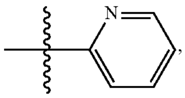
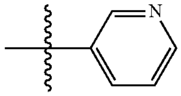 or 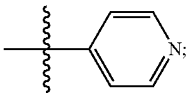
and m is an integer of 0, 1, 2 or 3.
7. The compound, or the isomers, the crystalline forms, the pharmaceutically acceptable salts, the hydrates or the solvates thereof according to claim 1, wherein in general formula (1), B is
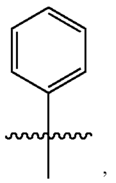, 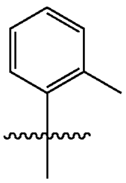, 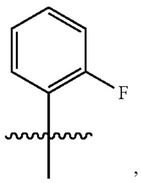,
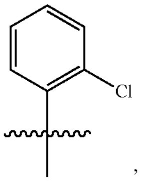, 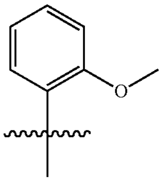, 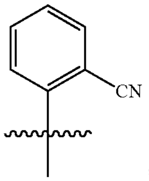,
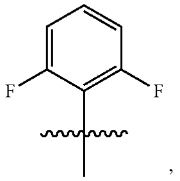, 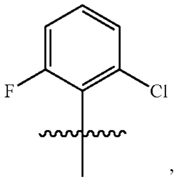, 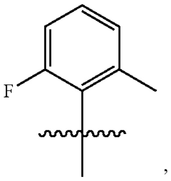,
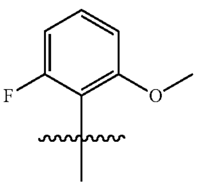, 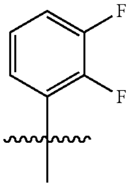, 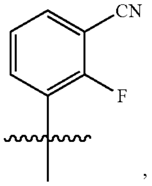,
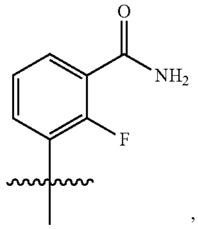, 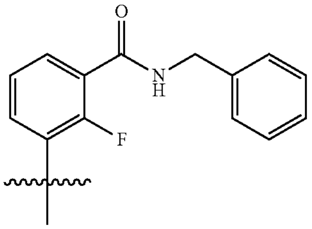, -continued
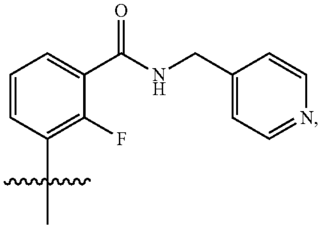
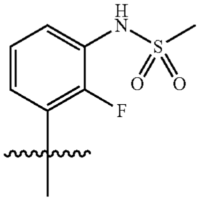 , 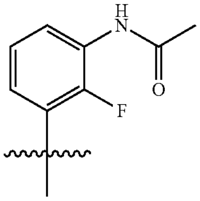 ,
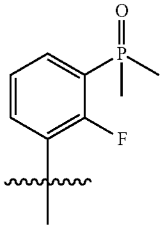 , 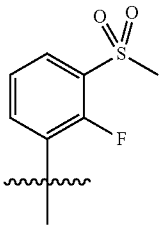 , 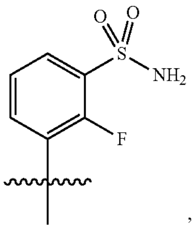 ,
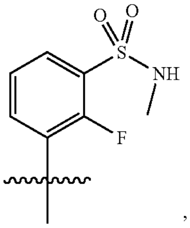 , 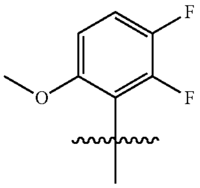 ,
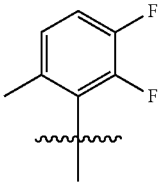 , 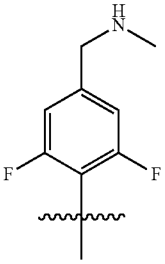 ,
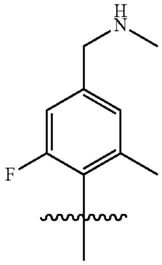 , 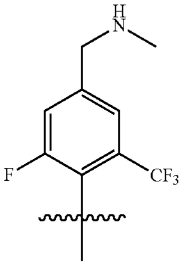 ,
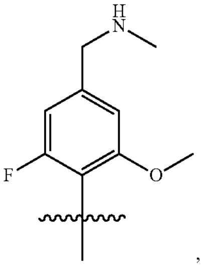 , 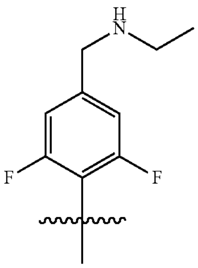 ,
-continued
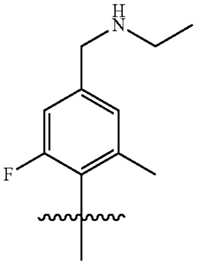 , 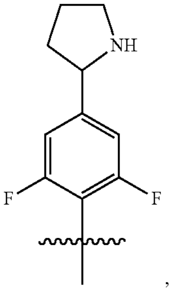 ,
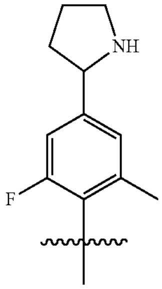 , 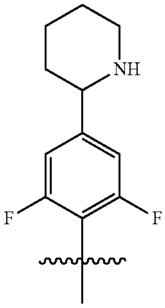 , 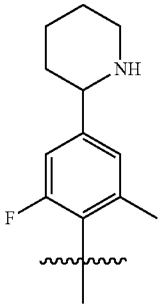 ,
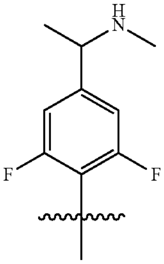 , 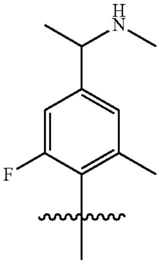 , 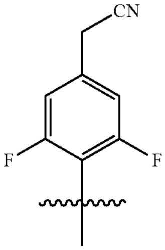 ,
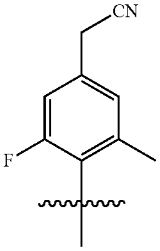 , 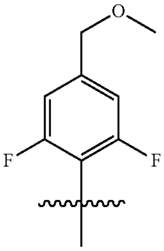 , 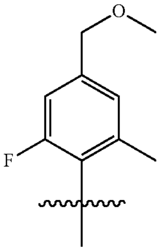 ,
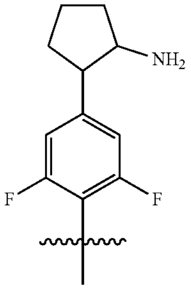 , 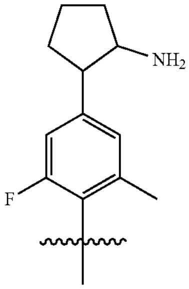 ,
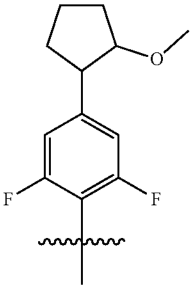 , 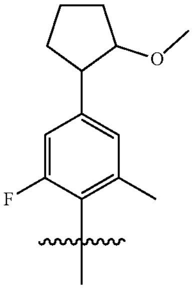 , -continued
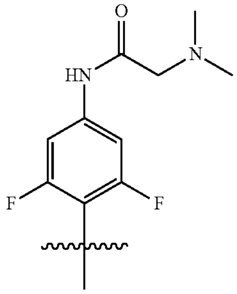
,
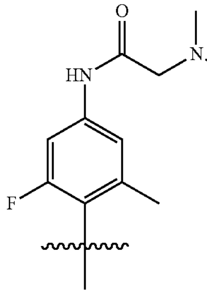
,
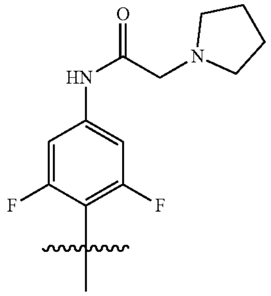
,
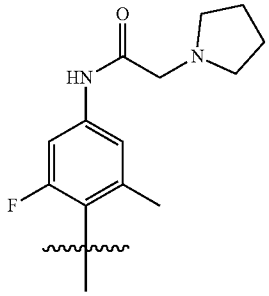
,
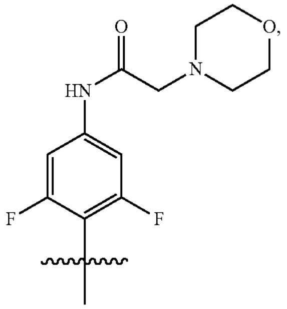
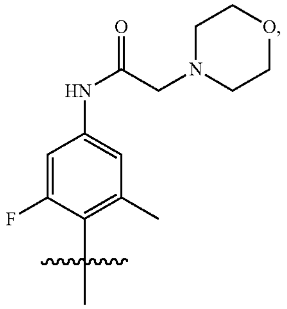
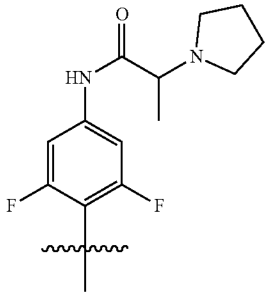
,
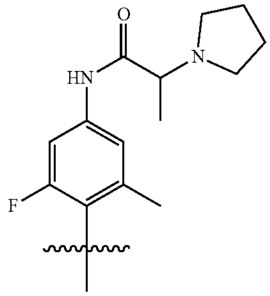
,
-continued
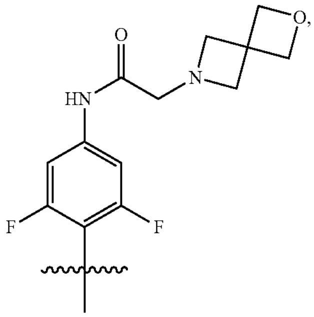
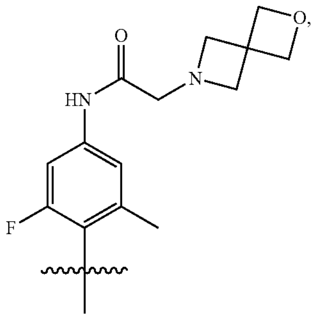
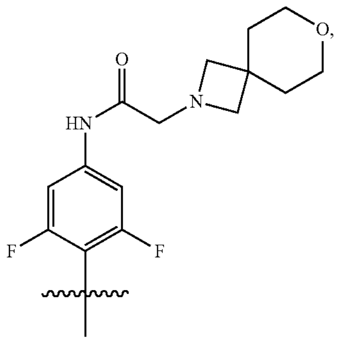
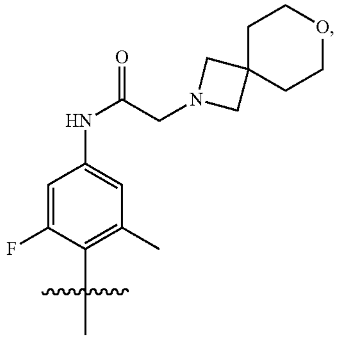
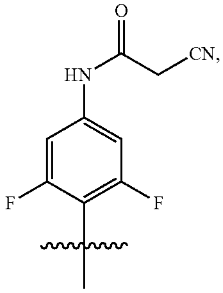
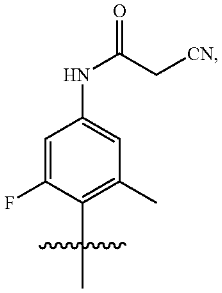

-continued
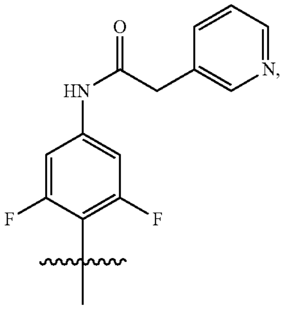
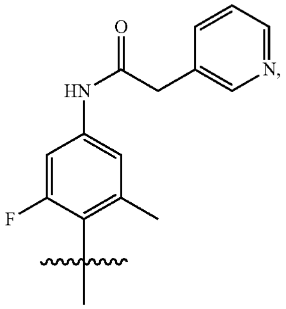
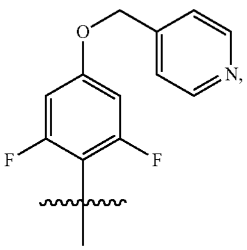
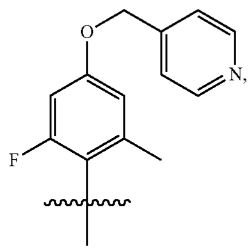
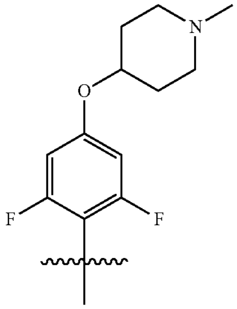
,
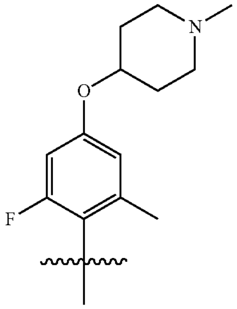
,
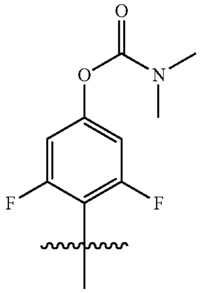
,
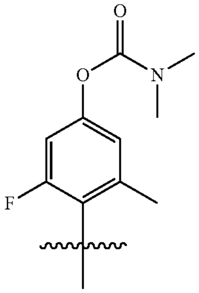
,
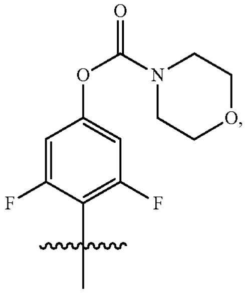
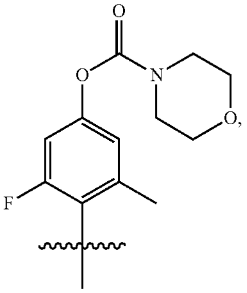
-continued
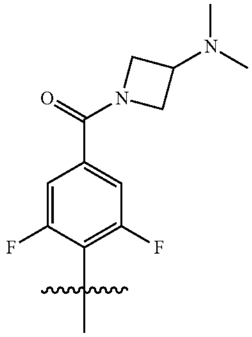
,
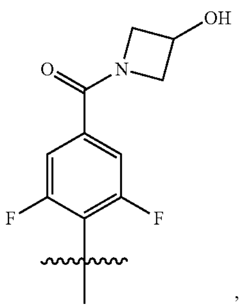
,
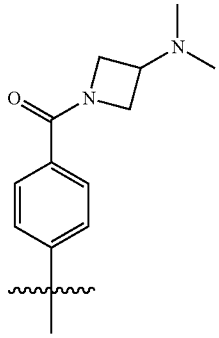
,
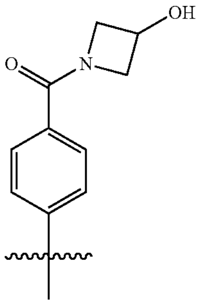
,
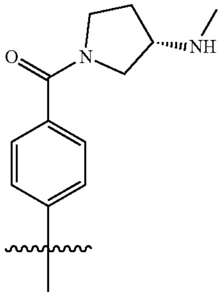
,
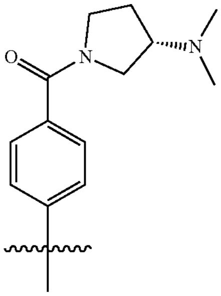
,
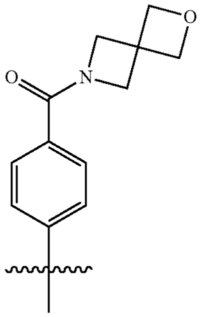
,
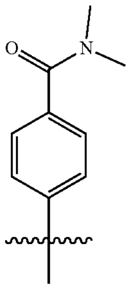
,
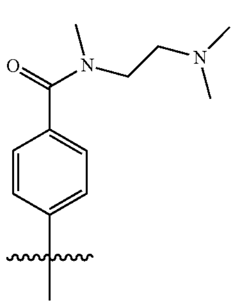
,
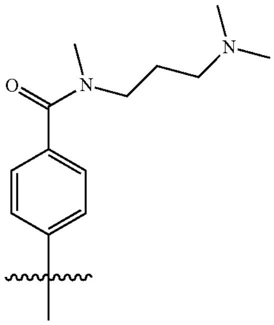
, -continued
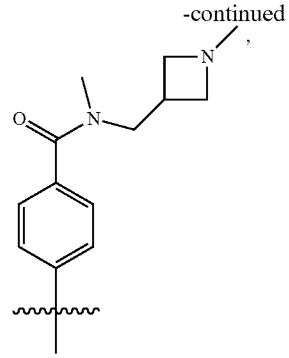
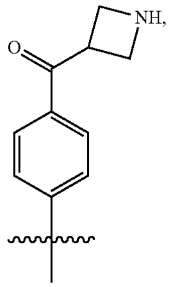
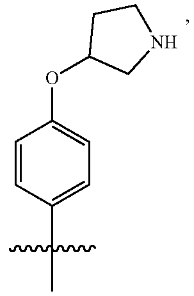
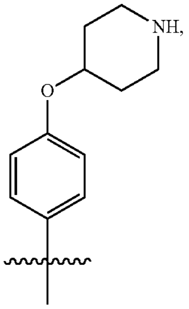
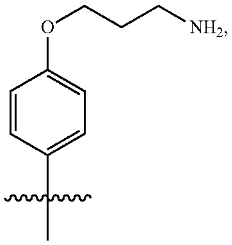
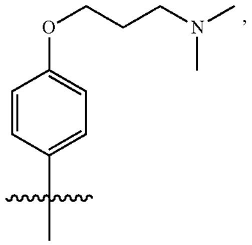
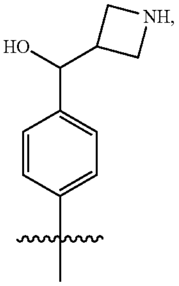
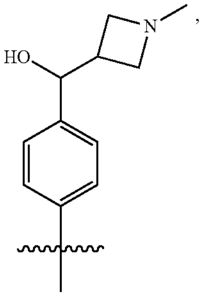
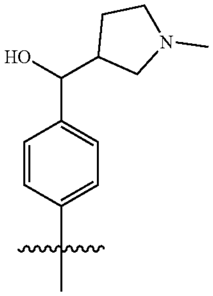
or
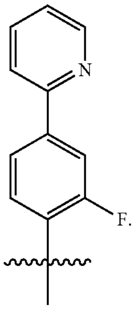
8. The compound, or the isomers, the crystalline forms, the pharmaceutically acceptable salts, the hydrates or the solvates thereof according to claim 1, wherein in general formula (1), B is
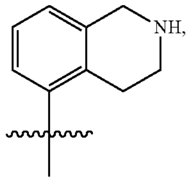
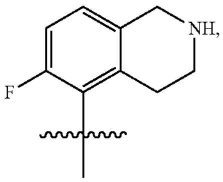
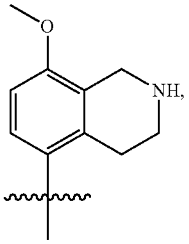
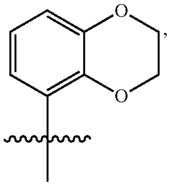
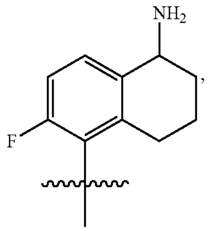
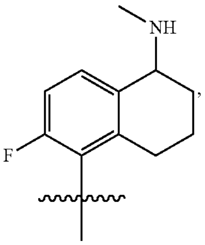
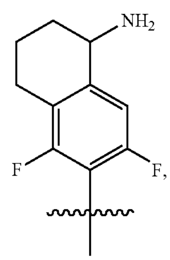
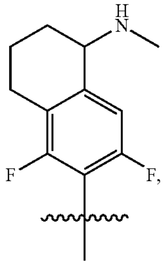
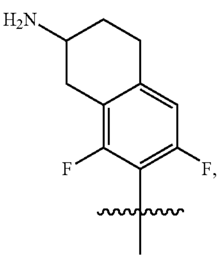
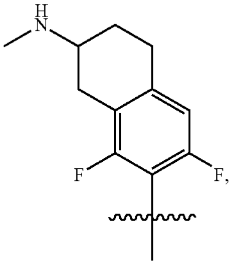
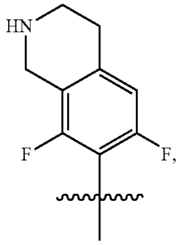
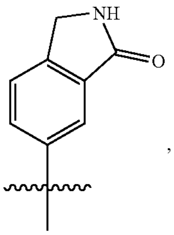
,
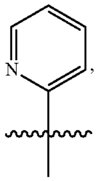
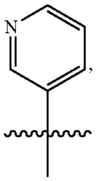
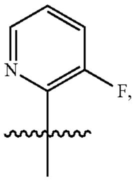
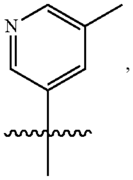
,
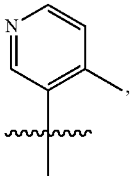

-continued
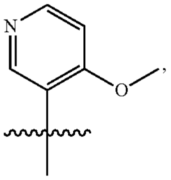
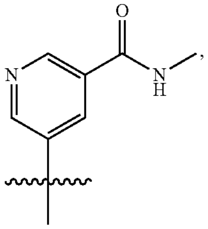
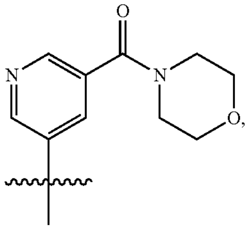
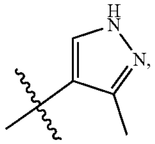
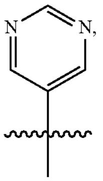
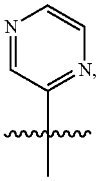
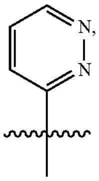
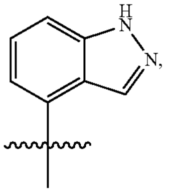
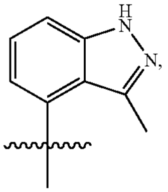
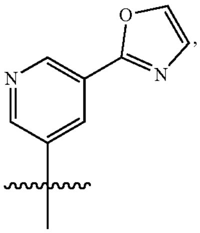
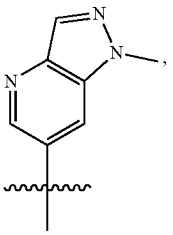
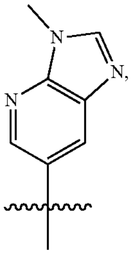
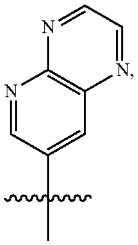
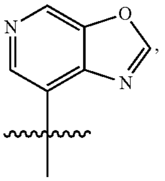
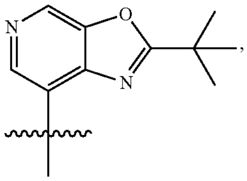
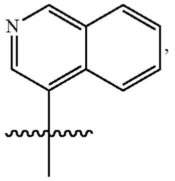
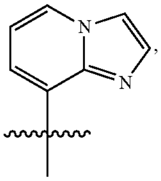
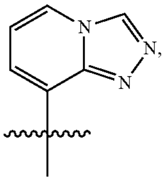
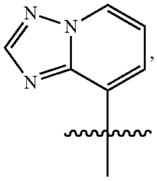
-continued
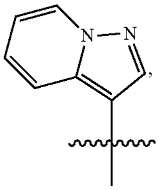
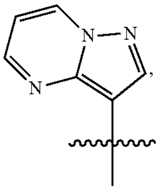
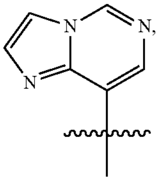
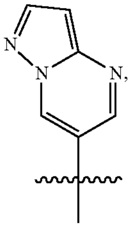
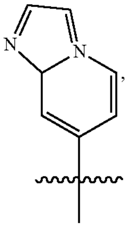
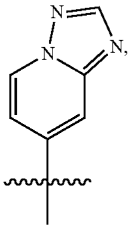
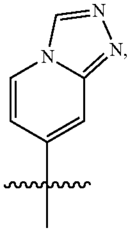
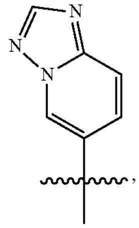
or
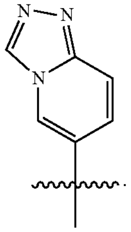
9. The compound, or the isomers, the crystalline forms, the pharmaceutically acceptable salts, the hydrates or the solvates thereof according to claim 1, wherein the compound has one of the following structures:
1
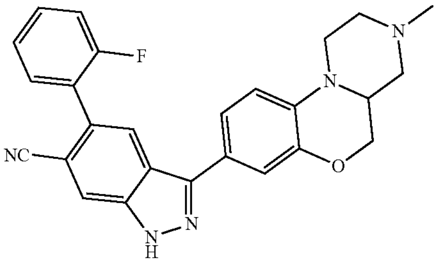
2
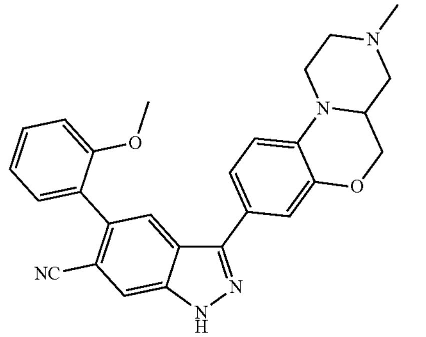

-continued
3
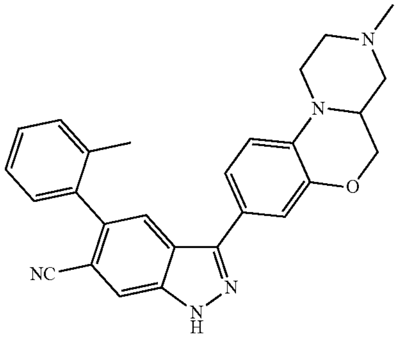
4
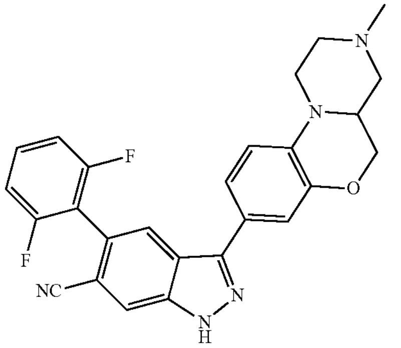
5
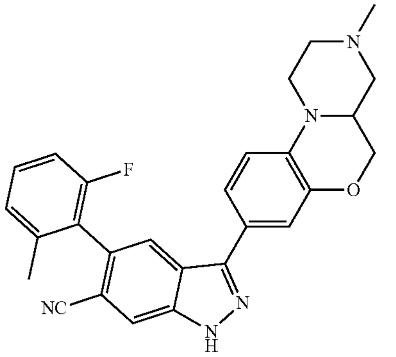
6
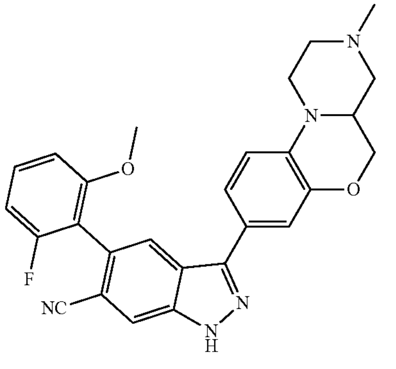
-continued
7
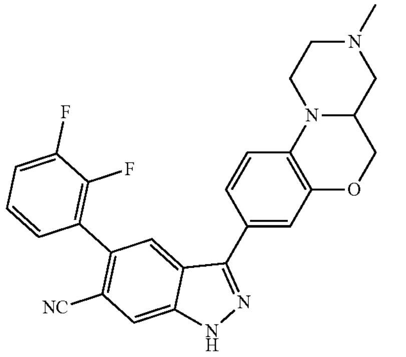
8
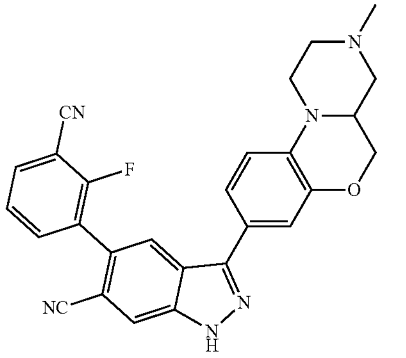
9
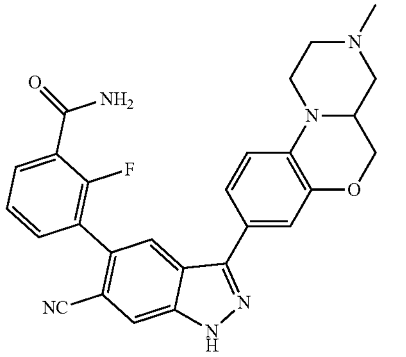
10
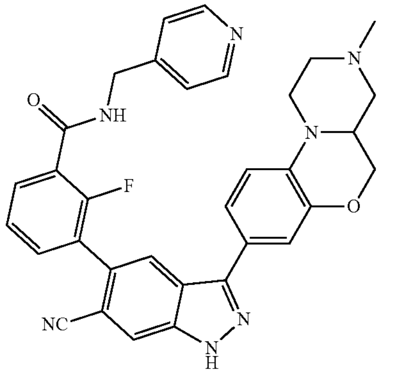

-continued
11
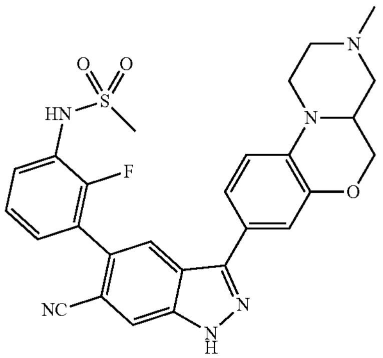
12
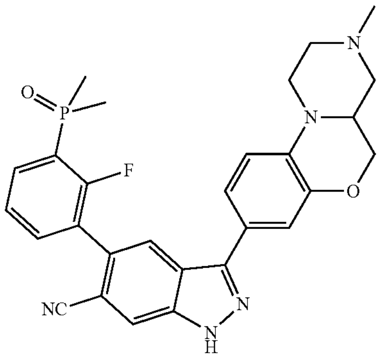
13
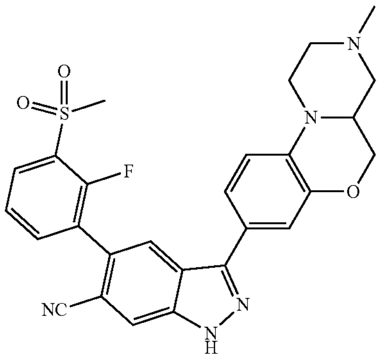
14
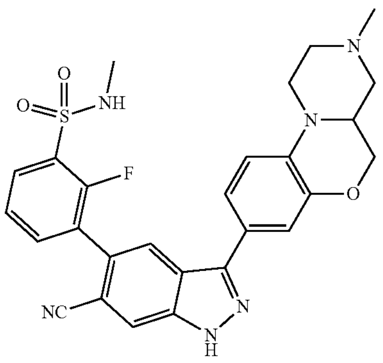
-continued
15
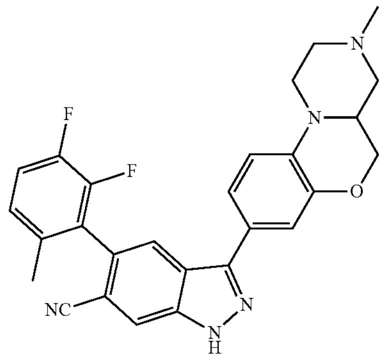
16
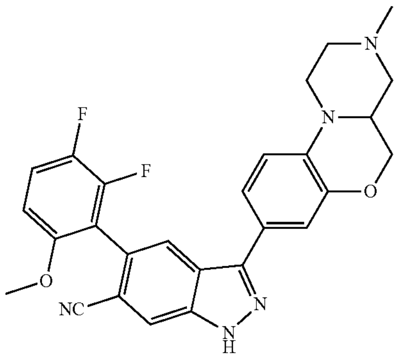
17
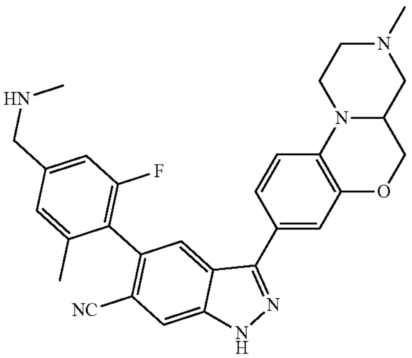
18
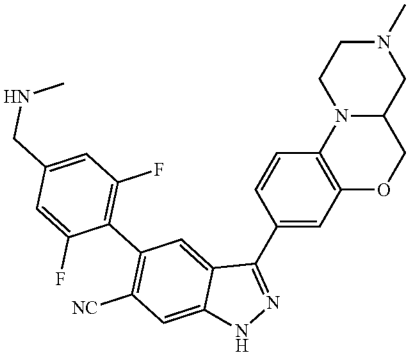

-continued
19
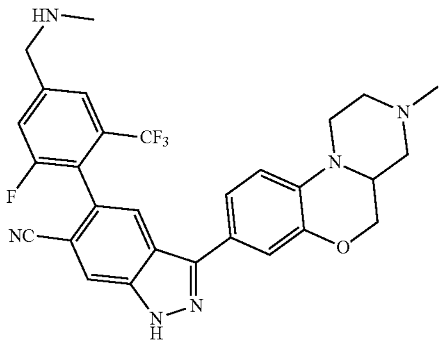
20
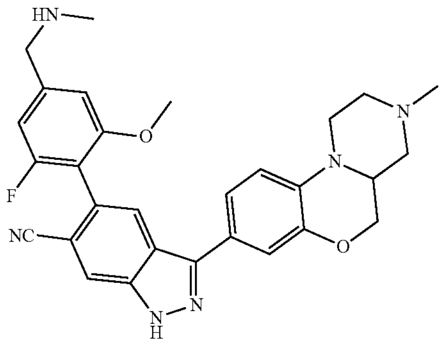
21
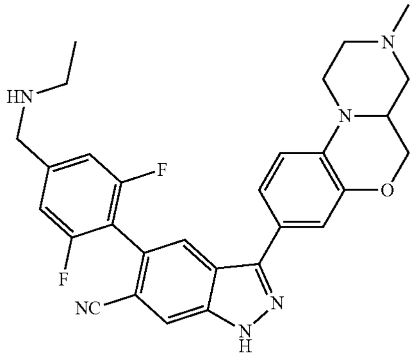
22
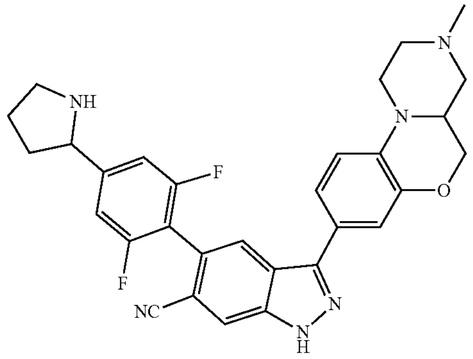
-continued
23
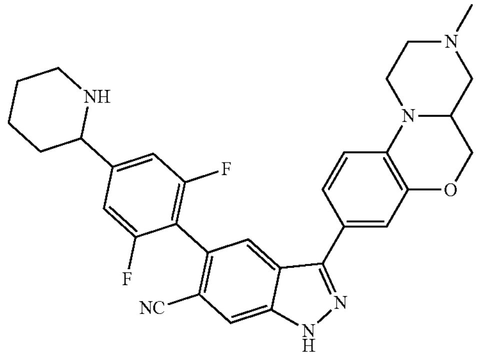
24
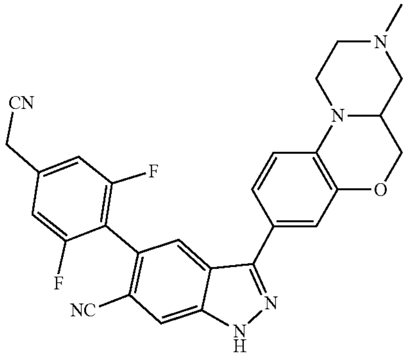
25
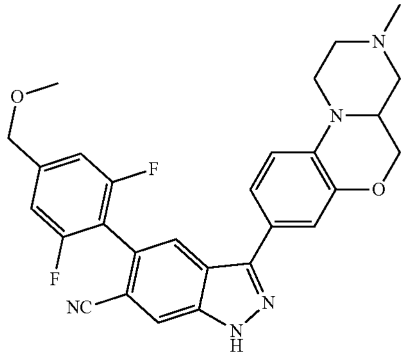
26
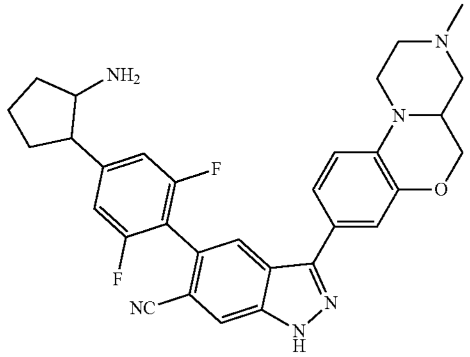

-continued
27
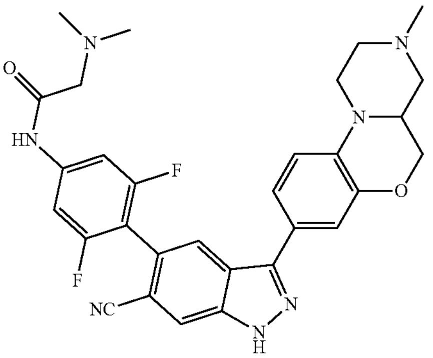
28
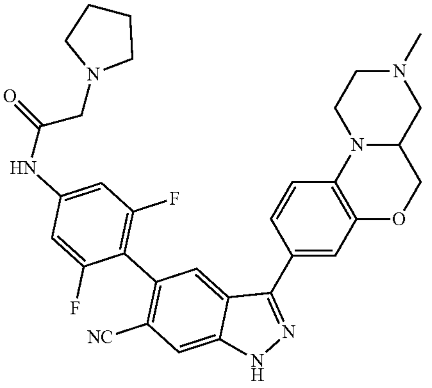
29
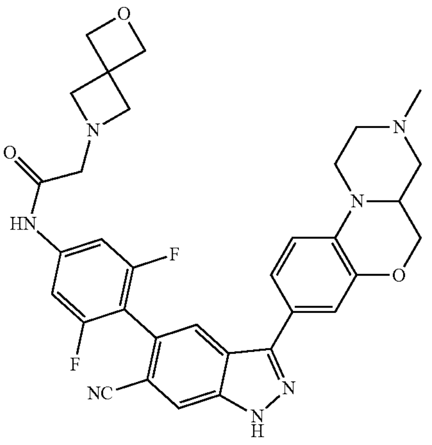
30
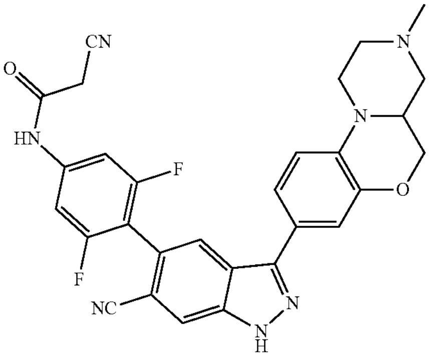
-continued
31
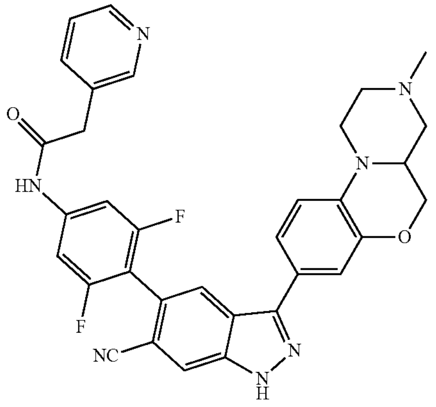
32
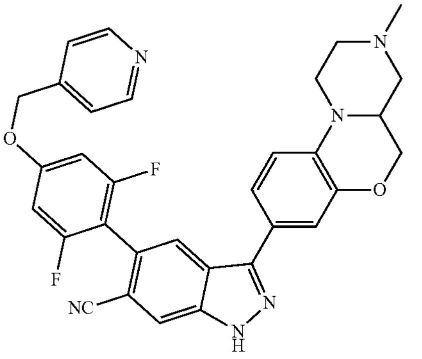
33
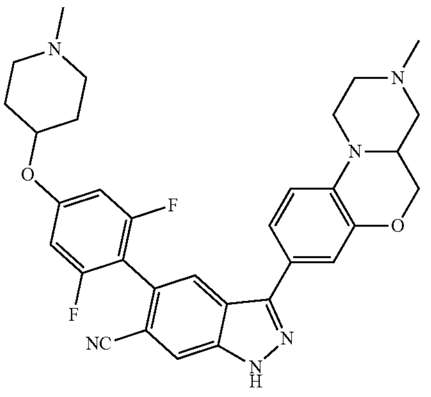
34
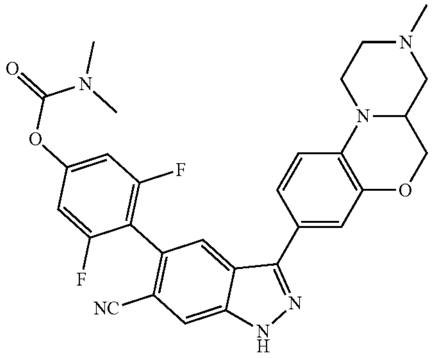

-continued
35
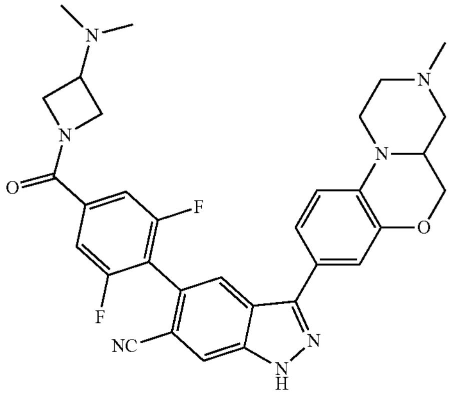
36
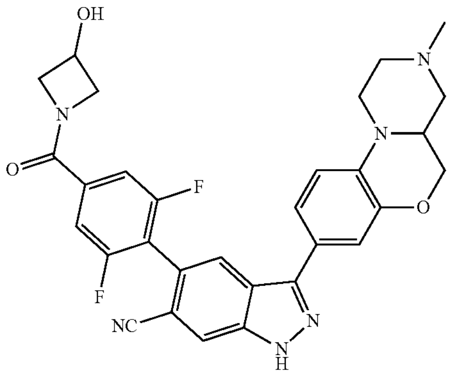
37
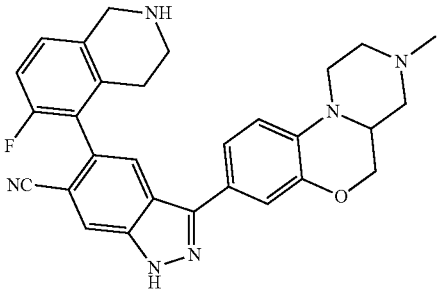
38
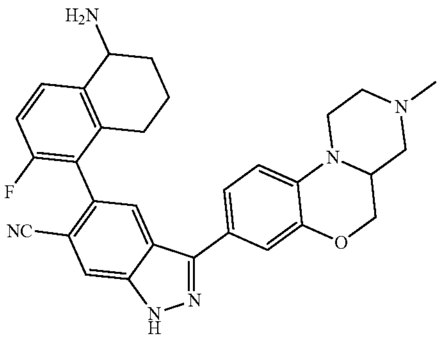
-continued
39
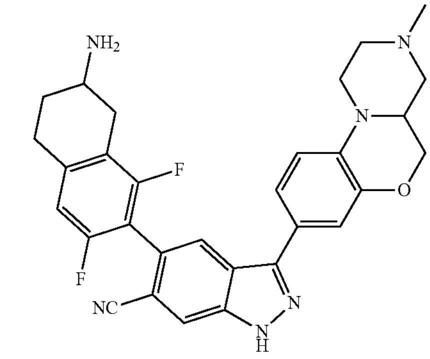
40
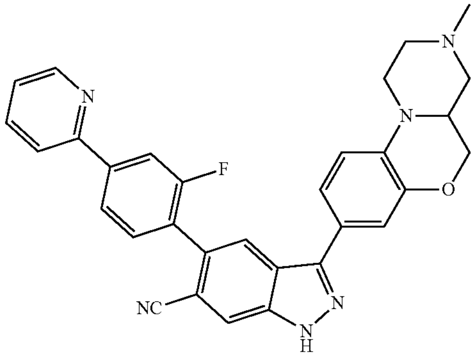
41
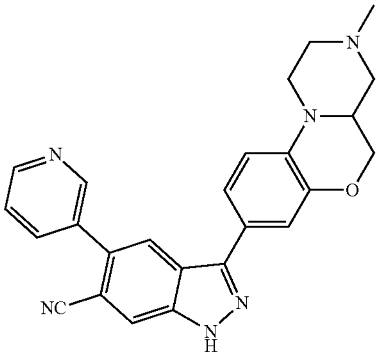
42
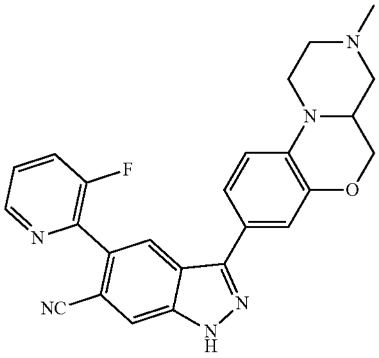

-continued
43
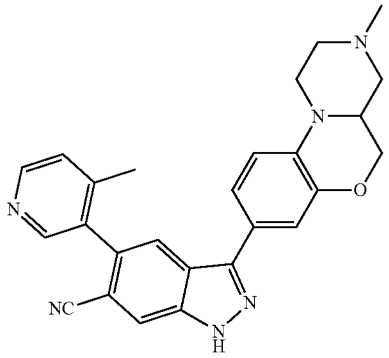
44
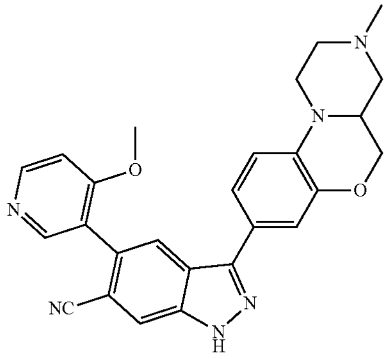
45
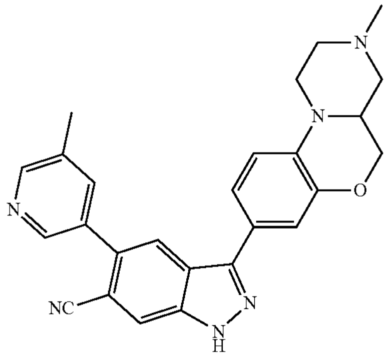
46
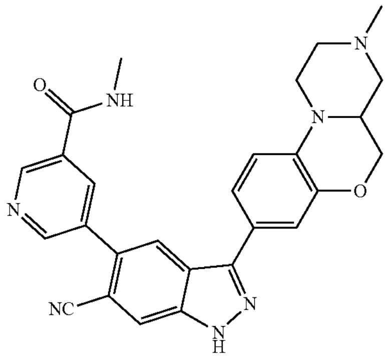
-continued
47
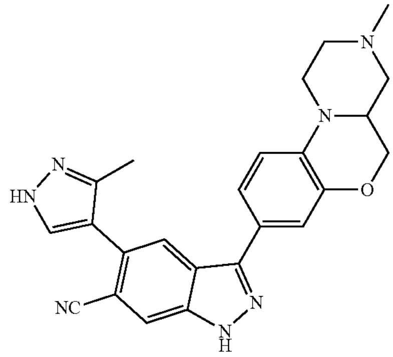
48
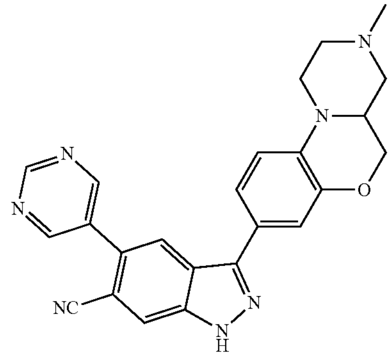
49
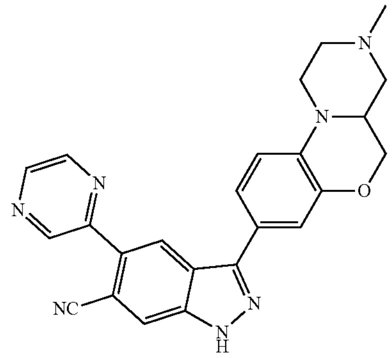
50
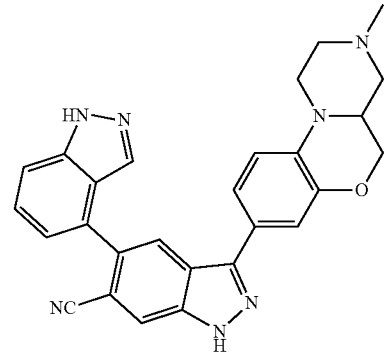

-continued
51
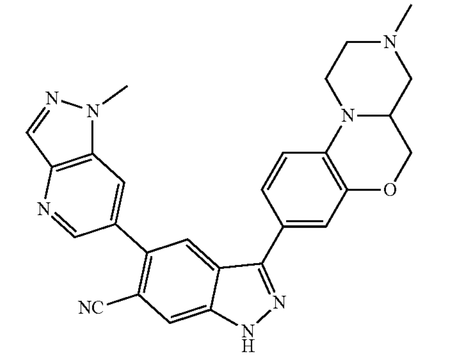
52
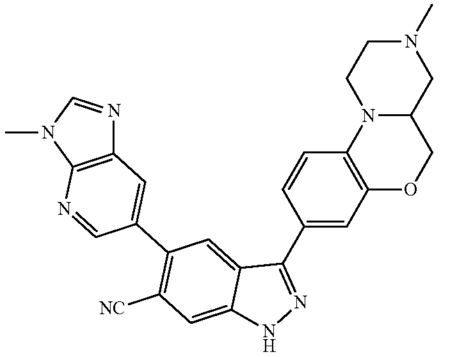
53
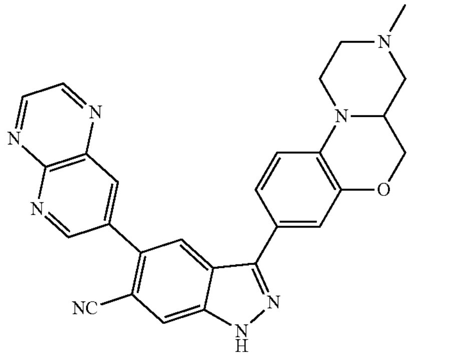
54
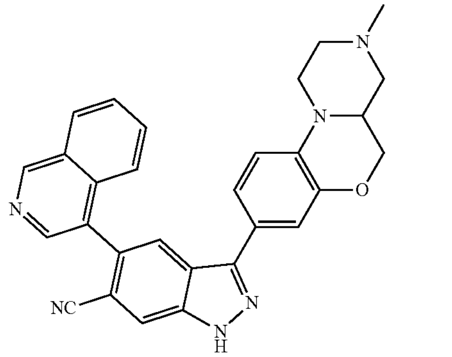
-continued
55
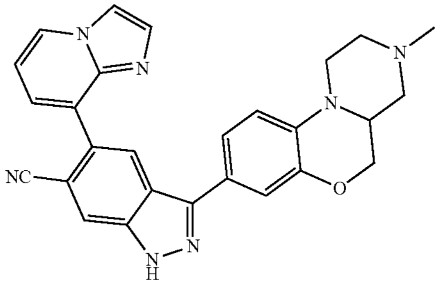
56
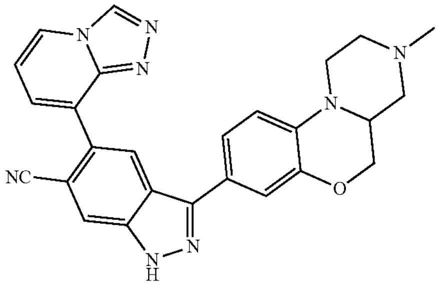
57
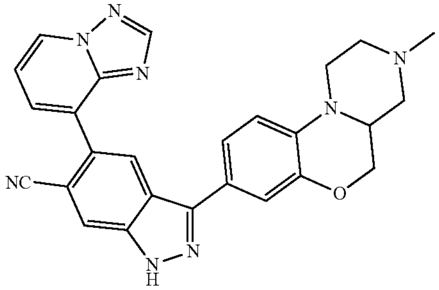
58
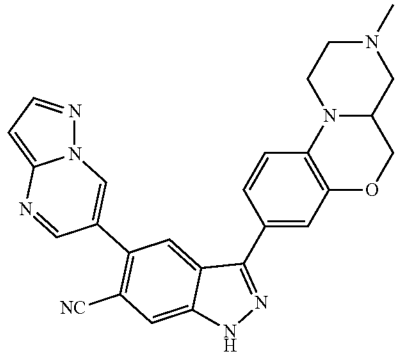
59
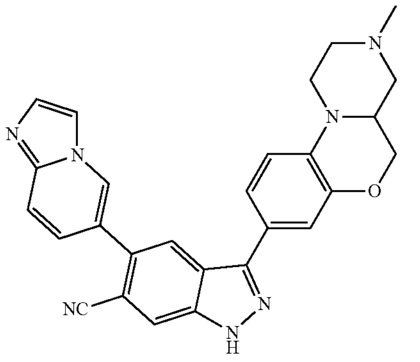

-continued
60
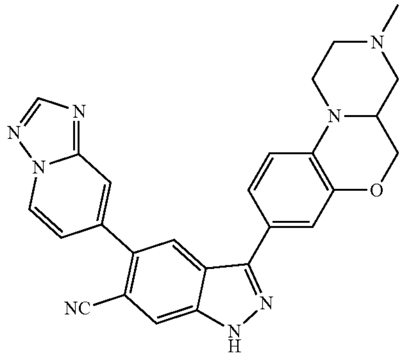
61
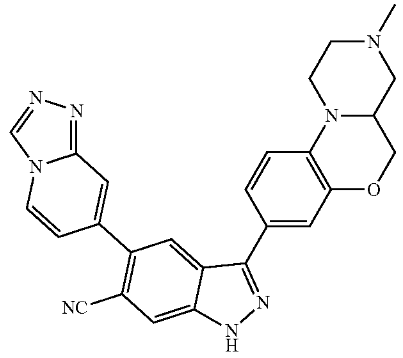
62
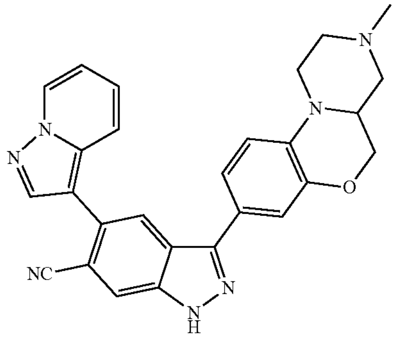
63
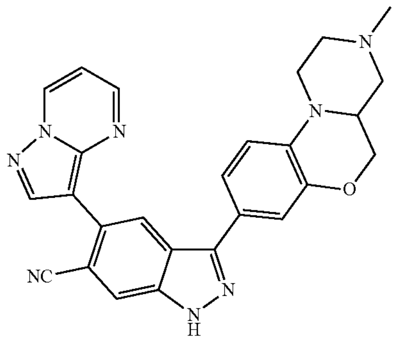
-continued
64
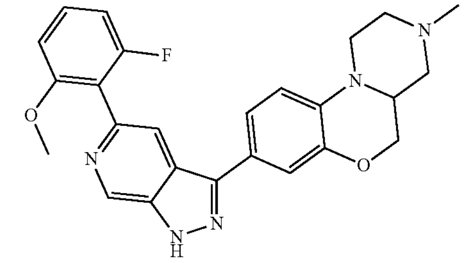
65
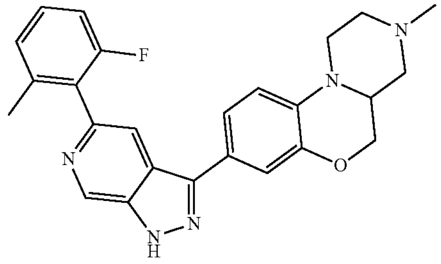
66
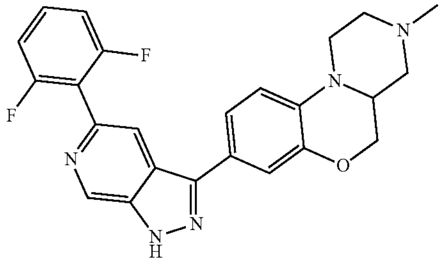
67
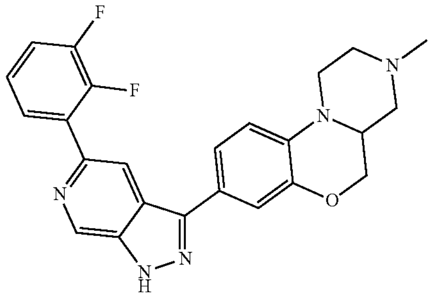
68
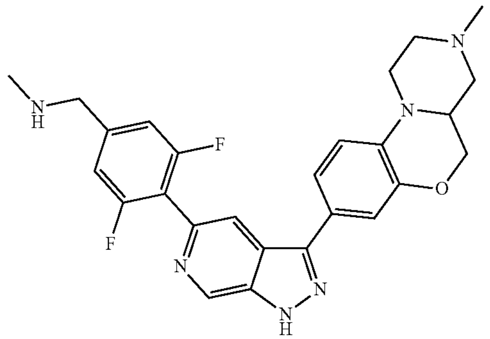

-continued
69
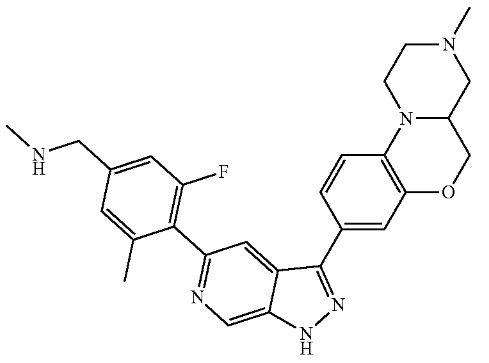
70
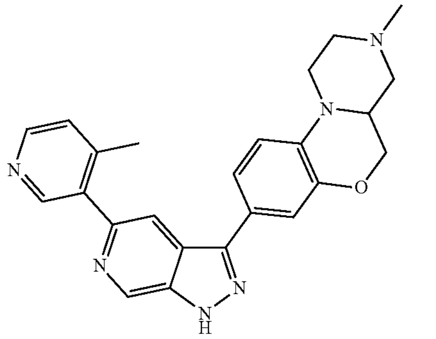
71
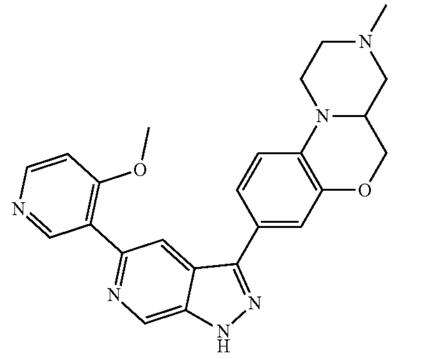
72
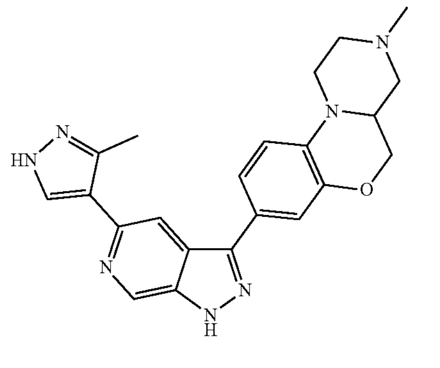
-continued
73
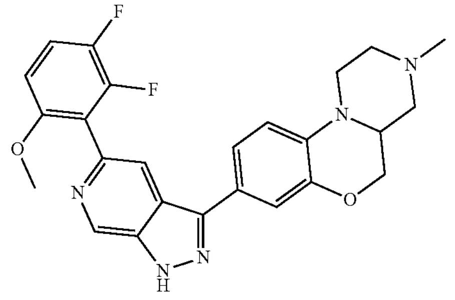
74
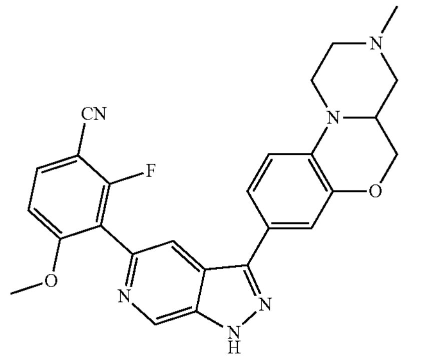
75
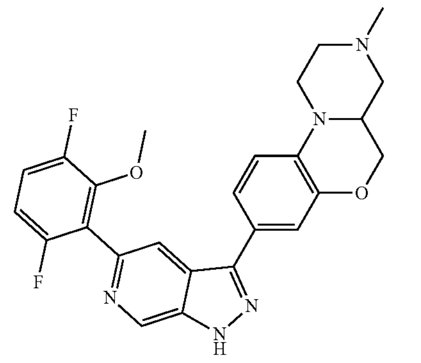
76
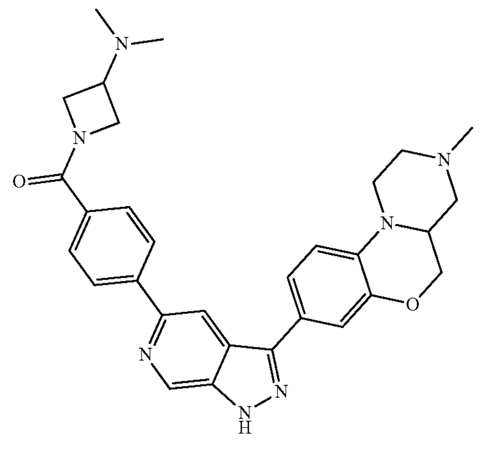

77
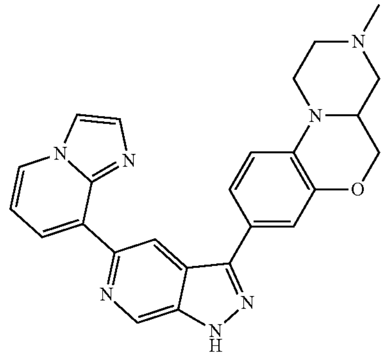
78
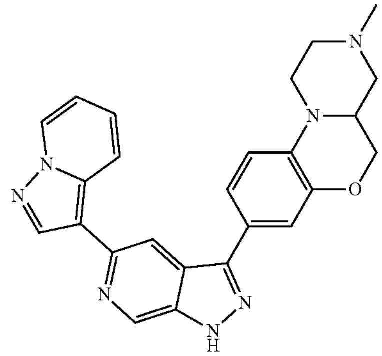
79
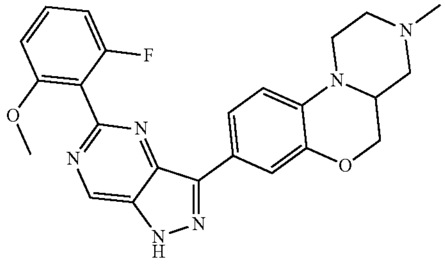
80
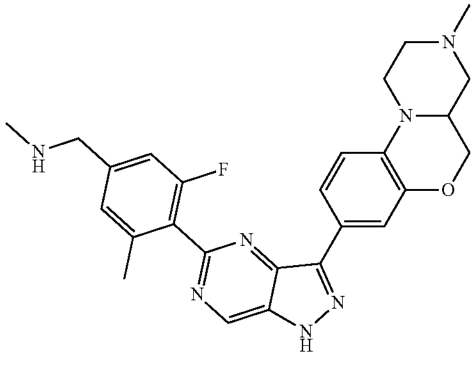
81
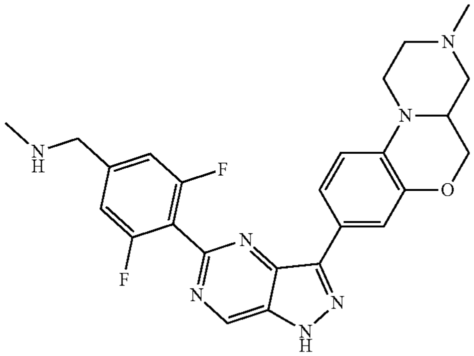
82
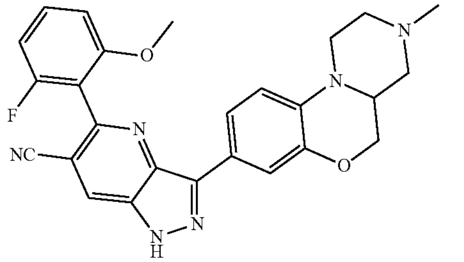
83
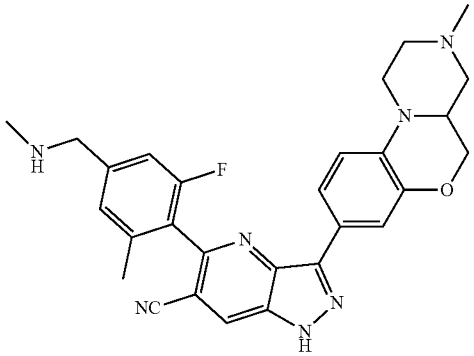
84
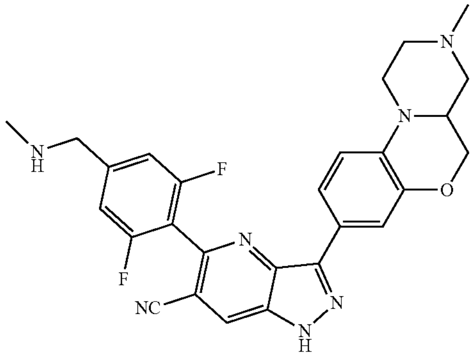
85
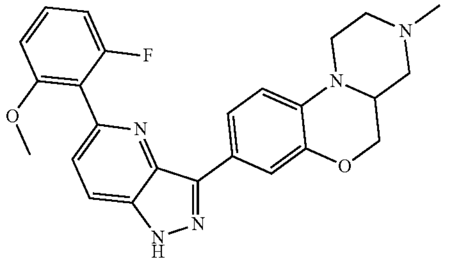

86
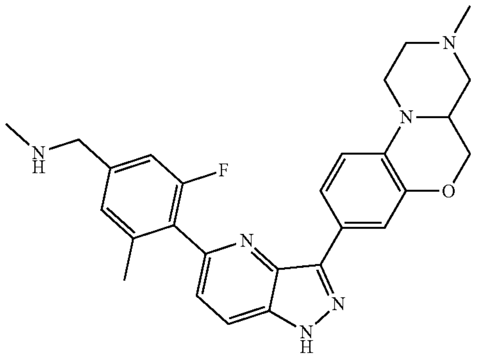
87
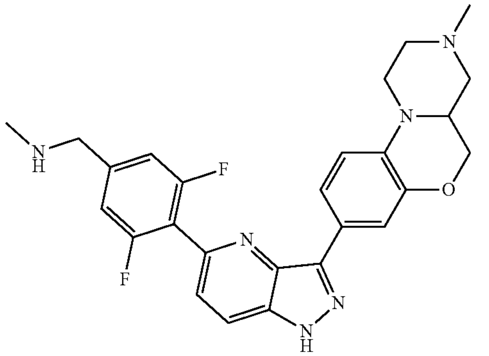
88
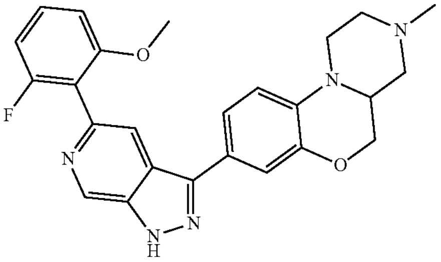
89
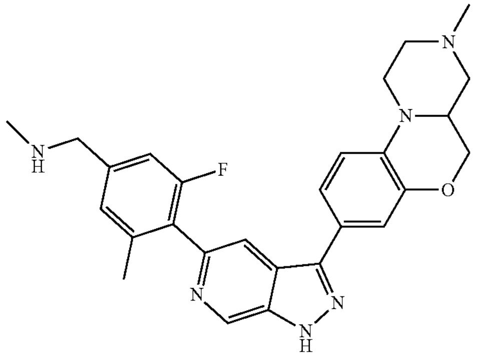
90
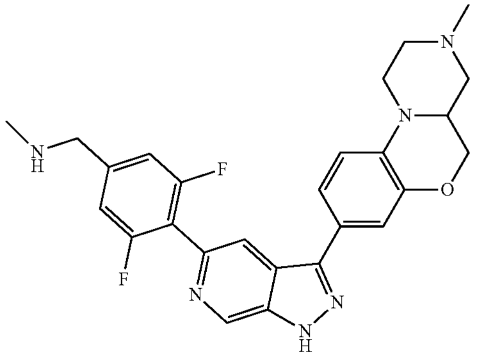
91
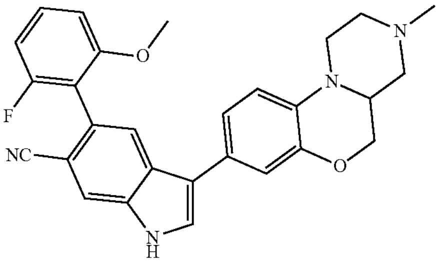
92
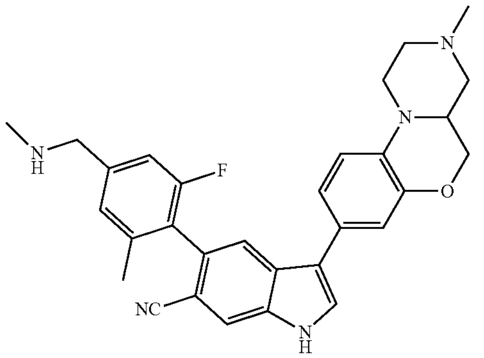
93
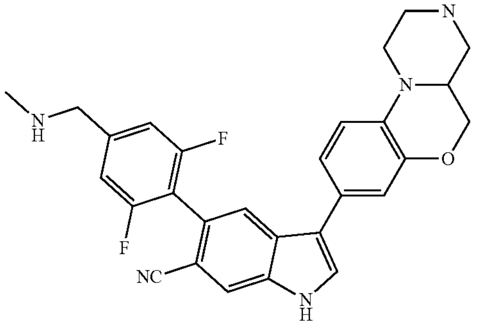
94
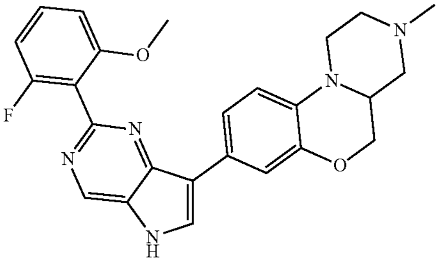

-continued
95
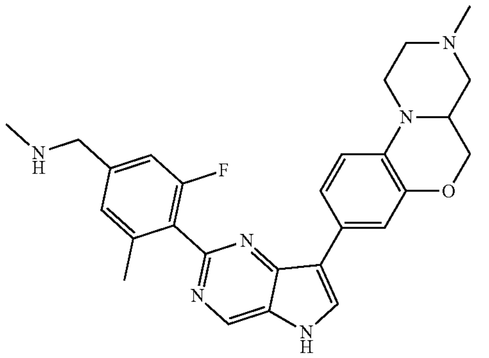
96
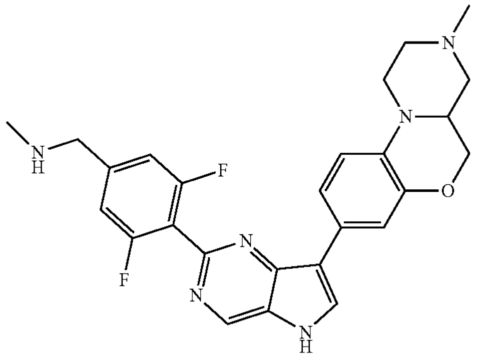
97
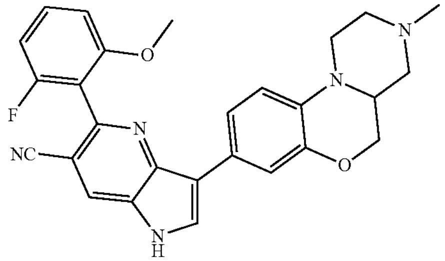
98
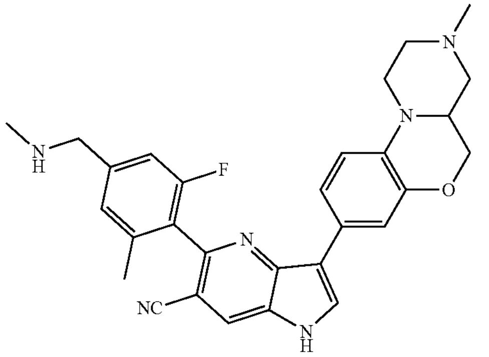
-continued
99
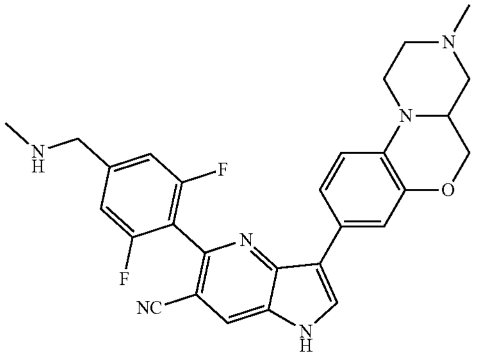
121
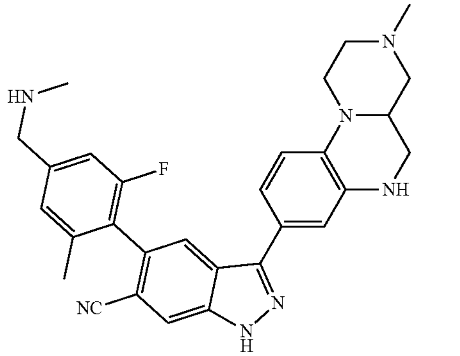
122
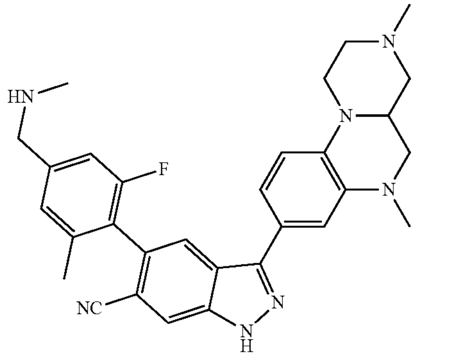
123
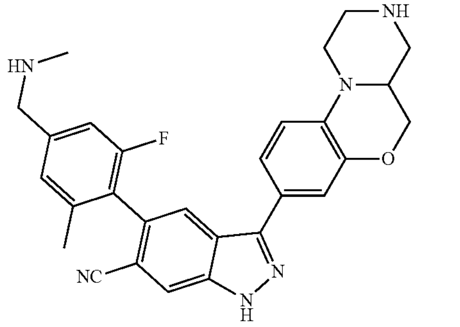

-continued
124
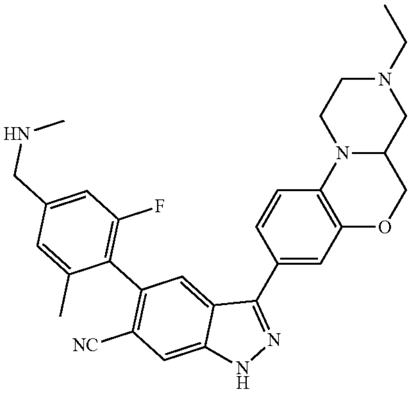
125
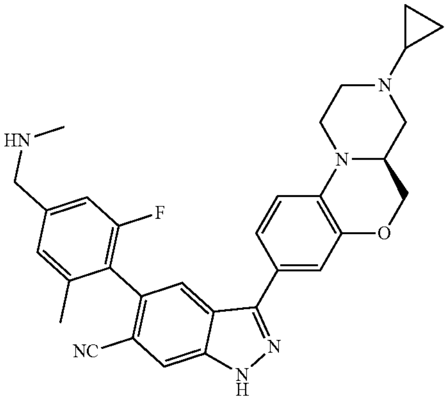
126
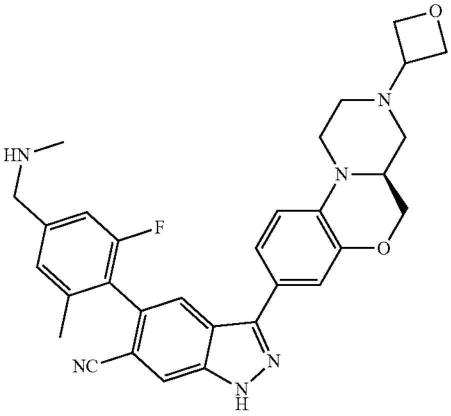
-continued
127
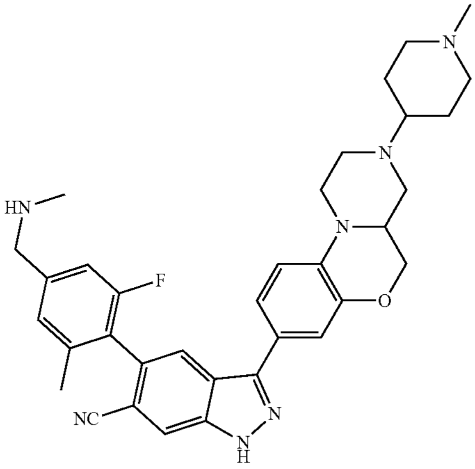
128
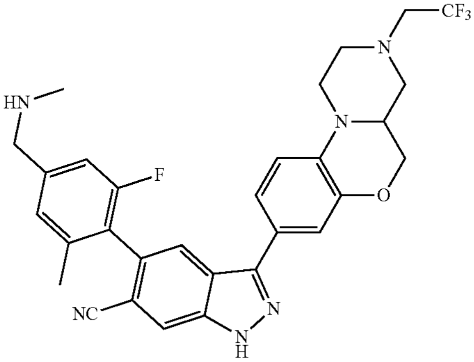
and
129
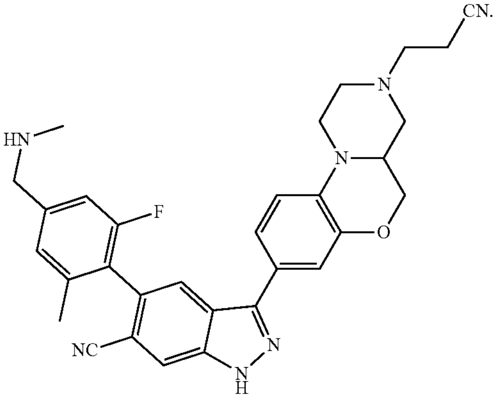
10. A pharmaceutical composition, comprising a pharmaceutically acceptable excipient or carrier, and the compound or the isomers, the crystalline forms, the pharmaceutically acceptable salts, the hydrates or the solvates thereof according to claim 1 as an active ingredient.
* * * * *